(12) United States Patent
Kolodych et al.

(10) Patent No.: US 11,975,075 B2
(45) Date of Patent: May 7, 2024

(54) BIOCONJUGATES WITH A CONTROLLED DEGREE OF CONJUGATION, THEIR PROCESS OF PREPARATION, AND THE REAGENTS FOR THEIR PREPARATION

(71) Applicants: CENTRE NATIONAL DE LA RECHERCHE SCIENTIFIQUE, Paris (FR); UNIVERSITÉ DE STRASBOURG, Strasbourg (FR); SYNDIVIA, Illkirch-Graffenstaden (FR)

(72) Inventors: Sergii Kolodych, Strasbourg (FR); Oleksandr Koniev, Strasbourg (FR); Alain Wagner, Strasbourg (FR); Igor Dovgan, Strasbourg (FR)

(73) Assignees: CENTRE NATIONAL DE LA RECHERCHE SCIENTIFIQUE, Paris (FR); UNIVERSITÉ DE STRASBOURG, Strasbourg (FR); SYNDIVIA, Strasbourg (FR)

( * ) Notice: Subject to any disclaimer, the term of this patent is extended or adjusted under 35 U.S.C. 154(b) by 870 days.

(21) Appl. No.: 16/628,315

(22) PCT Filed: Jul. 6, 2018

(86) PCT No.: PCT/EP2018/068428
§ 371 (c)(1),
(2) Date: Jan. 3, 2020

(87) PCT Pub. No.: WO2019/008164
PCT Pub. Date: Jan. 10, 2019

(65) Prior Publication Data
US 2020/0147232 A1    May 14, 2020

(30) Foreign Application Priority Data
Jul. 6, 2017  (EP) ..................... 17305879

(51) Int. Cl.
*A61K 47/68* (2017.01)
*A61K 47/54* (2017.01)

(52) U.S. Cl.
CPC ........ *A61K 47/6803* (2017.08); *A61K 47/545* (2017.08); *A61K 47/6851* (2017.08)

(58) Field of Classification Search
CPC ............ A61K 47/6803; A61K 47/6851; A61K 47/545

USPC ....................................... 424/181.1
See application file for complete search history.

(56) References Cited

U.S. PATENT DOCUMENTS

2017/0081300 A1*  3/2017  Taran ................... C07D 495/04

FOREIGN PATENT DOCUMENTS

| CN | 101657464 A | 2/2010 |
| CN | 105813655 A | 7/2016 |
| CN | 105848671 A | 8/2016 |

OTHER PUBLICATIONS

International Search Report, dated Sep. 21, 2018, from corresponding PCT application No. PCT/EP2018/068428.
European Search Report, dated Dec. 19, 2017, from corresponding EP application No. 17 30 5879.
Dovgan et al.; Acyl Fluorides: Fast, Efficient, and Versatile Lysine-Based Protein Conjugation via Plug-and-Play Strategy; Bioconjugate Chemistry; Apr. 26, 2017; pp. 1452-1457; vol. 28, No. 5.
Dovgan et al.; Supporting Information: Acyl Fluorides: Fast, Efficient, and Versatile Lysine-Based Protein Conjugation via Plug-and-Play Strategy; Bioconjugate Chemistry; May 17, 2017.
Sun et al.; Effects of Drug-Antibody Ratio on Pharmacokinetics, Biodistribution, Efficacy, and Tolerability of Antibody-Maytansinoid Conjugates; Bioconjugate Chemistry; Apr. 13, 2017; pp. 1371-1381; vol. 28, No. 5.
Sochaj et al.; Current methods for the synthesis of homogeneous antibody-drug conjugate; Biotechnology Advances; May 14, 2015; pp. 775-784; vol. 33, No. 6.
Yao et al.; Methods to Design and synthesize Antibody-Drug Conjugates (ADCs); International Journal of Molecular Sciences; Feb. 2, 2016; pp. 194; vol. 17, No. 2.
Strop et al.; Site-specific conjugation improves therapeutic index of antibody drug conjugates with high drug loading; Nature Biotechnology; Jul. 8, 2015; pp. 694-696; vol. 33, No. 7.

* cited by examiner

*Primary Examiner* — Kristin A Vajda
(74) *Attorney, Agent, or Firm* — NIXON & VANDERHYE, PC

(57) ABSTRACT

Disclosed is a process for preparation of heterogeneous monodisperse mixtures of protein conjugates with a defined degree of conjugation (1-8) obtained by using a tri-functional reagent allowing affinity concentration followed by subsequent simultaneous release-functionalization.

Figure 1:
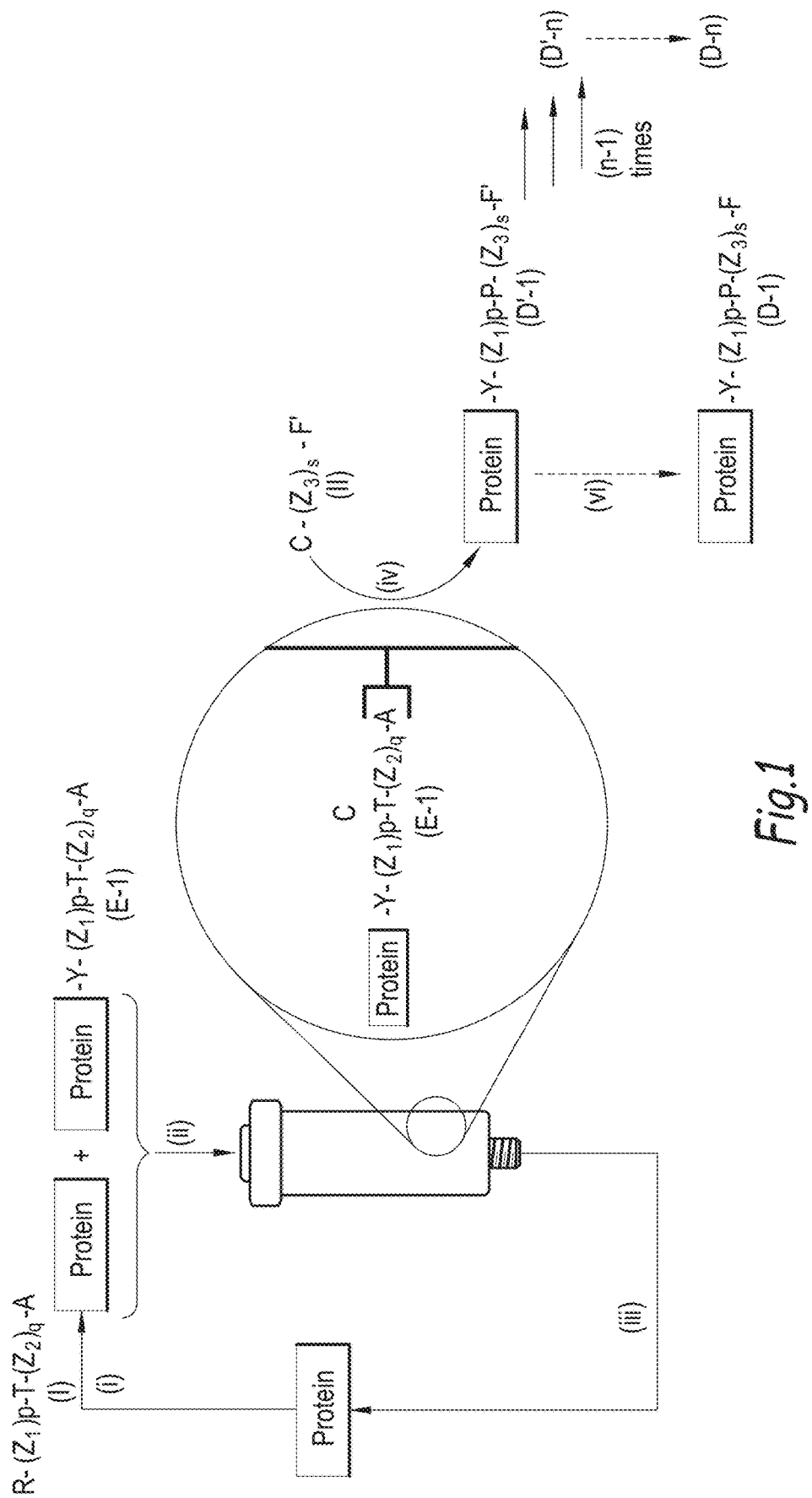

16 Claims, 3 Drawing Sheets
Specification includes a Sequence Listing.

BIOCONJUGATES WITH A CONTROLLED DEGREE OF CONJUGATION, THEIR PROCESS OF PREPARATION, AND THE REAGENTS FOR THEIR PREPARATION

The present invention concerns the field of bioconjugated agents, such as antibody conjugates where an antibody is conjugated to one or more functional entities (herein called "payload"), in particular antibody drug conjugates (ADCs).

ADCs have been attracting major attention, as it is one of fastest growing classes of oncology therapeutics. The approval of brentuximab vedotin and trastuzumab emtansine paved the way for ongoing clinical trials.

Indeed, many ADCs candidates are currently being under development with a significant number of ADCs in late clinical stage forecasted to be commercialized as mixtures of different species.

The ADCs currently developed are essentially mixtures of different species meaning that the drug-to-antibody ratio (DAR, also called degree of conjugation or DoC) follows a binominal distribution within the sample. In other words, the number of drugs conjugated to the antibody is neither controlled nor defined and only the average number of drugs is usually taken into account.

It has been reported that one of the main challenge in ADCs design is homogeneity of ADCs molecules. The two approved ADCs mentioned above and most of the ADCs under development are heterogeneous in that they have 0 to 8 drug molecules per antibody (and average DAR of 3-4) generally and it has been reported that this may have deleterious impact on the pharmacokinetics, pharmacodynamics, in vivo performance/efficiency and/or therapeutic window (side effect) of the conjugated drug (Bioconjugate Chemistry 2017, 28, 1371-1381). Dovgan et al report a plug-and-play process (Bioconjugate Chemistry, 2017, vol. 28, pages 1452-1457). However, the method used by the authors is a plug-and-play process, which, although uses click chemistry for payload attachment, yields heterogeneous mixtures of conjugates having different DoC. Therefore, more efforts have now been developed in this filed in order to better control the degree of conjugation and/or site of conjugation of ADCs (Nature biotechnology, vol. 33, 7, 694-696, 2015).

Methods have been developed for DAR controlling, but, most of the time, this requires monoclonal antibody reengineering, use of specific enzymes, or complete reduction of disulfide bonds followed by rebridging thereof. The methods developed so far are expensive, complex and limited in terms of versatility and degree of conjugation. It is therefore desired to provide an efficient method to lead to ADCs with controlled degree of conjugation.

According to the invention, a rapid, easy, most efficient and effective process purely based on chemical reactions has been developed, which can lead to:
- DNA or RNA conjugated antibodies;
- Multi-specific antibodies;
- Multi-functional antibodies;
- Multi-functionalizable antibodies to be used in conjugation;
- Possibility to be used in any biological entities composed of amino acids (peptides and proteins);
- Possibility to choose any degree of conjugation; and/or
- Possibility to choose the site of attachment (e.g. cysteine, lysine, tyrosine, phenylalanine, arginine residues of the protein).

According to the first object, the present invention concerns a mixture of regioisomeric DAR-specific protein conjugates of formula (D-n):

Protein-(G)$_n$  (D-n)

Wherein
n represents the total degree of conjugation (DoC) and is an integer comprised between 1 and 8;
Protein is a naturally occurring or synthetic protein, or a fragment thereof;
(G) refers to conjugate fragment(s), identical or different that is/are grafted to Protein at the same or different sites of attachment,
provided that each fragment (G) has a respective degree of conjugation i comprised between 1 and 8, where $\Sigma(i)=n$;
And where each fragment (G) is of the following formula:

—Y—(Z$_1$)$_p$—P—(Z$_3$)$_s$—F  (G)

Provided that each of Y, Z$_1$, P, Z$_3$, F, n, p and s are the same or different for each (G) and in case n is higher than 1, (G) fragments in (D-n) can be same or different;
Said mixture being characterized in that, for a given conjugate fragment (G):
there is a defined respective Degree of Conjugation (DoC) i;
the mixture comprises conjugate(s) having said fragment (G), such that at least 90% of said conjugate(s) have the defined respective DoC i;
p and s are independently 0 or 1;
Z$_1$ and Z$_3$ are optional spacer units independently selected from the group consisting of a C6-C12 arylene; a linear or branched, saturated or unsaturated, C$_1$-C$_{60}$ alkylene group optionally interrupted and/or terminated by one or more chemical groups selected from —O—, —S—, —S(O)—, —SO2-, —O—P(O)(OH)—O—, —C(O)—, —NH—, —C(O)NH—, —NHC(O)—, —C(O)NR$_4$—, —NR$_4$C(O)—, heteroarylene, arylene, mono or bicyclic (C3-C10)cycloalkylene, glycosyl, an —O—(CH$_2$—CH$_2$—O—)$_r$—, —NH—(CH$_2$—CH$_2$—O—)$_r$—, —(—O—CH$_2$—CH$_2$—)$_r$ or —(CH$_2$—CH$_2$—O—)$_r$— groups; and an amino acid or peptide residue, where the rings may be optionally fused;
In particular Z$_1$ and Z$_3$ are optional spacer units independently selected from the group consisting of a C6-C12 arylene; a linear or branched, saturated or unsaturated, C$_1$-C$_{60}$ alkylene group optionally interrupted and/or terminated by one or more chemical groups selected from —O—, —S—, —S(O)—, —SO2-, —O—P(O)(OH)—O—, —C(O)—, —NH—, —C(O)NH—, —NHC(O)—, —C(O)NR$_4$—, —NR$_4$C(O)—, heteroarylene, arylene, glycosyl, an —O—(CH$_2$—CH$_2$—O—)$_r$—, —NH—(CH$_2$—CH$_2$—O—)$_r$—, —(—O—CH$_2$—CH$_2$—)$_r$ or —(CH$_2$—CH$_2$—O—)$_r$— groups; and an amino acid or peptide residue;
in which r is an integer ranging from 1 to 24, and
where R$_4$ is a solubility unit selected from the group consisting of C1-C6 alkylene, where one or more H is/are substituted by any of the following fragments:

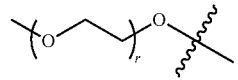

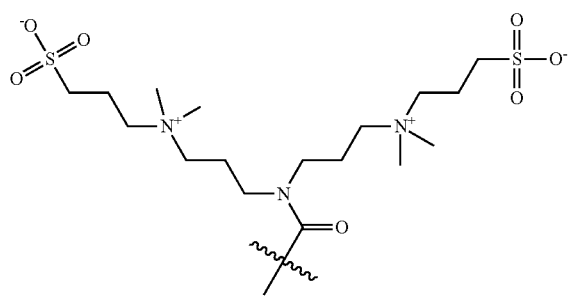
P is a trans-tagged unit resulting from the reaction of two complementary trans-tagging functions T and C, P being preferably selected from:
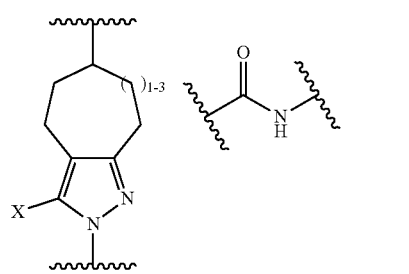
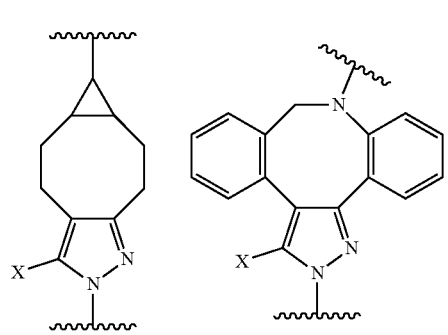
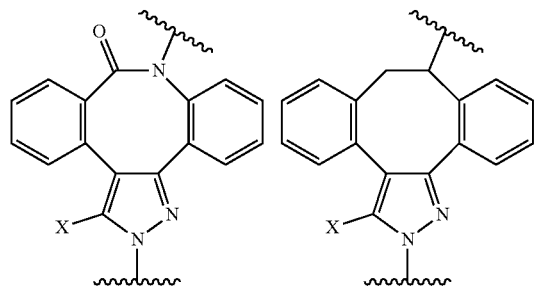
In particular from:
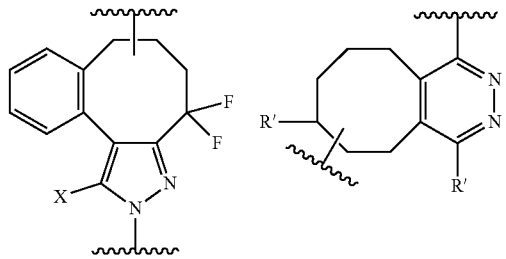
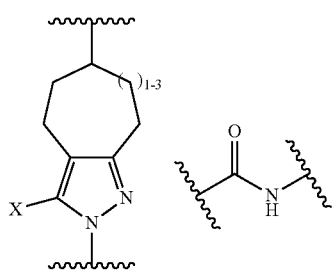
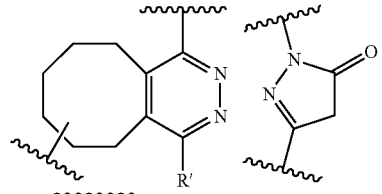
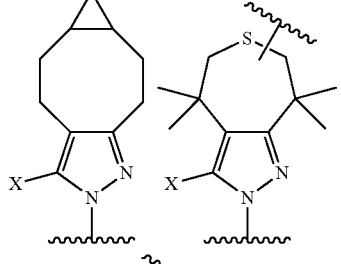
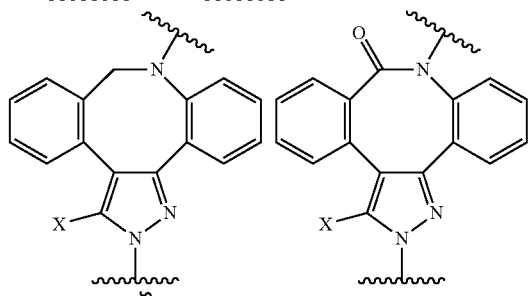
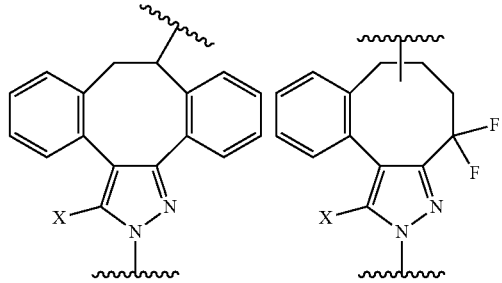

F is a functional agent, in particular selected from drugs such as antineoplastic agents; oligonucleotides; antibodies; or detection agents;

X is H or a halogen atom (F, Cl, Br, I);

Y is a chemical residue resulting from the reaction of R with amino acid residues present in Protein under aqueous conditions, preferably selected from the group consisting in:

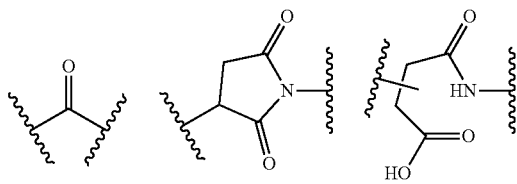

in particular in:

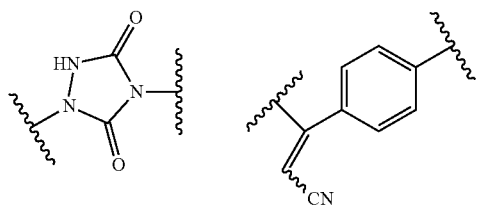

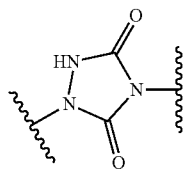

According to an embodiment, the mixture of the invention comprises protein conjugates of formula (D-n) having all the same conjugate fragment (G), with the same DoC, where said conjugates may differ by the site of attachment on the Protein.

According to an embodiment, the mixture of the invention comprises protein conjugates of formula (D-n) having different conjugate fragments (G), where each conjugate fragment has a given i DoC, where said conjugates may further differ by the site of attachment on the Protein.

One feature of the mixture of the invention is that the mixture is essentially monodisperse with respect to the DoC of each conjugate fragment. It is therefore a uniform mixture in terms of the total degree of conjugation n and in terms of the respective degree of conjugation i for each conjugate fragment. According to an embodiment, for a given conjugate fragment or for all conjugate fragments, at least 90%, typically at least 95%, more particularly at least 97% of the species/mixture have said degree of conjugation i/n.

The conjugates of formula (D-n) are:
Structurally heterogeneous in that for each conjugate fragment (G), the conjugates may be regioisomers and/or the conjugate fragments (G) may be the same or different, provided that for each conjugate fragment (G), the DoC is controlled and defined; and
Have a defined protein/payload ratio (DAR or DoC), herein referred to "DAR-specific".

In the sense of the invention, the term "regioisomers" refers to isomeric protein-drug conjugates, where the protein backbone remains unchanged, but the substituents on the protein may be attached to different sites on the protein.

The term "heterogeneous" according to the invention refers to protein conjugates, where the conjugate fragments may be attached to different locations of the protein. This term does not mean that the DoC for a conjugate fragment can vary.

The heterogeneity in the sense of the invention above had not been accessible via any site-specific conjugation process so far.

Without being bound by any theory, it is expected that the heterogeneity in the sense of the invention may be an important feature to overcome some of the drug resistance mechanisms (as in the organism becomes resistant to only one of the many structural/regional variants). Moreover, heterogeneity in the sense of the invention prevents the formation of hydrophobic clusters on the surface of the protein and therefore has a positive effect on the pharmacokinetics of the conjugates (Nature biotechnology, vol. 33, 7, 694-696, 2015).

According to an embodiment of F, the drugs are selected from cytotoxic drugs and antineoplasic agents.
Suitable drugs include in particular:
dolastatins such as MMAE, MMAF, MMAD
maytansins such as DM1 and DM4
antracyclins such as doxorubicin, nemorubicin and PNU-159682
calicheamicins
duocarymycins such as CC-1065 and duocarmycin A
pyrrolobenzodiazepines
pyrrolobenzodiazepine dimers
indolino-benzodiazepines
indolino-benzodiazepine dimers
amanitins such as α-amanitin, β-amanitin, γ-amanitin, ε-amanitin
exotoxins such as diphtheria toxin, shiga toxin, or subunits thereof;
in particular:
dolastatins such as MMAE, MMAF, MMAD
maytansins such as DM1 and DM4
antracyclins such as doxorubicin, nemorubicin and PNU-159682
calicheamicins
duocarymycins such as CC-1065 and duocarmycin A
pyrrolobenzodiazepines
pyrrolobenzodiazepine dimers
indolino-benzodiazepines
indolino-benzodiazepine dimers amanitins such as α-amanitin, β-amanitin, γ-amanitin, ε-amanitin Suitable oligonucleotides for F include silencing RNA, microRNA, antisense oligonucleotides, DNA, or RNA oligomers. Typically they are between 10 and 5000 nucleotides in length, more particularly, between 20 and 200.

Suitable detection agents for F include imaging agents, biological markers, tracing agents, such as fluorophores, dyes, radioactive tracers.

According to an embodiment, Protein may be any synthetic or naturally occurring compound comprising one or more aminoacid, such as peptide or a protein. Typically, Protein is a monoclonal antibody, such as human, humanized, mouse or chimeric antibodies. Typical antibodies include trastuzumab, bevacizumab, cetuximab, panitumumab, ipilimumab, rituximab, alemtuzumab, ofatumumab, gemtuzumab, brentuximab, ibritumomab, tositumomab, pertuzumab, adecatumumab, IGN101, INA01 labetuzumab, hua33, pemtumomab, oregovomab, minretumomab (CC49), cG250, J591, MOv-18, farletuzumab (MORAb-003), 3F8, ch14,18, KW-2871, hu3S193, IgN311, IM-2C6, CDP-791, etaracizumab, volociximab, nimotuzumab, MM-121, AMG 102, METMAB, SCH 900105, AVE1642, IMC-A12, MK-0646, R1507, CP 751871, KB004, III A4, mapatumumab, HGS-ETR2, CS-1008, denosumab, sibrotuzumab, F19, 8106, pinatuzumab, lifastuzumab, glembatumumab, coltuximab, lorvotuzumab, indatuximab, anti-PSMA, MLN-0264, ABT-414, milatuzumab, ramucirumab, abagovomab, abituzumab, adecatumumab, afutuzumab, altumomab pentetate, amatuximab, anatumomab, anetumab, apolizumab, arcitumomab, ascrinvacumab, atezolizumab, bavituximab, bectumomab, belimumab, bivatuzumab, brontictuzumab, cantuzumab, capromab, catumaxomab, citatuzumab, cixutumumab, clivatuzumab, codrituzumab, conatumumab, dacetuzumab, dallotuzumab, daratumumab, demcizumab, denintuzumab, depatuxizumab, derlotuximab, detumomab, dinutuximab, drozitumab, duligotumab, durvalumab, dusigitumab, ecromeximab, edrecolomab, elgemtumab, emactuzumab, enavatuzumab emibetuzumab, enfortumab, enoblituzumab, ensituximab, epratuzumab, ertumaxomab, etaracizumab, farletuzumab, ficlatuzumab, figitumumab, flanvotumab, futuximab, galiximab, ganitumab, icrucumab, igovomab, imalumab, imgatuzumab, indusatumab, inebilizumab, intetumumab, iratumumab, isatuximab, lexatuzumab, lilotomab, lintuzumab, lirilumab, lucatumumab, lumretuzumab, margetuximab, matuzumab, mirvetuximab, mitumomab, mogamulizumab, moxetumomab, nacolomab, naptumomab, narnatumab, necitumumab, nesvacumab, nimotuzumab, nivolumab, nofetumomab, obinutuzumab, ocaratuzumab, ofatumumab, olaratumab, onartuzumab, ontuxizumab, oportuzumab, oregovomab, otlertuzumab, pankomab, parsatuzumab, pasotuxizumab, patritumab, pembrolizumab, pemtumomab, pidilizumab, pintumomab, polatuzumab, pritumumab, quilizumab, racotumomab, ramucirumab, rilotumumab, robatumumab, sacituzumab, samalizumab, satumomab, seribantumab, siltuximab, sofituzumab, tacatuzumab, taplitumomab, tarextumab, tenatumomab, teprotumumab, tetulomab, ticilimumab, tigatuzumab, tositumomab, tovetumab, tremelimumab, tucotuzumab, ublituximab, ulocuplumab, urelumab, utomilumab, vadastuximab, vandortuzumab, vanticutumab, vanucizumab, varlilumab, veltuzumab, vesencumab, volociximab, vorsetuzumab votumumab, zalutumumab, zatuxima, combination and derivatives thereof, as well as other monoclonal antibodies targeting CAI 25, CAI 5-3, CAI 9-9, L6, Lewis Y, Lewis X, alpha fetoprotein, CA 242, placental alkaline phosphatase, prostate specific antigen, prostate specific membrane antigen, prostatic acid phosphatase, epidermal growth factor, MAGE-I, MAGE-2, MAGE-3, MAGE-4, transferrin receptor, p97, MUCI, CEA, gplOO, MARTI, IL-2 receptor, CD20, CD52, CD33, CD22, human chorionic gonadotropin, CD38, CD40, mucin, P21, MPG, and Neu oncogene product.

The sites of attachment of the conjugate fragment of the Protein typically include amino acids residues, such as lysine, arginine, cysteine, tyrosine, phenylalanine, tryptophan, histidine, serine, threonine that are present in various locations within the Protein structure.

Typically, the Y group is attached at an amino group of the Protein, i.e. on lysine residues and/or N-termini.

According to an embodiment, the DoC may be chosen from 1, 2, 3, 4, 5, 6, 7 and 8. Typically, the DoC of each conjugate fragment is 1, 2, 3, 4 or 5.

In one embodiment, the mixture comprises conjugates having a DoC of 1. In an embodiment, the mixture of protein conjugates comprises at least 90% of the protein conjugates having the formula (D-1):

$$\text{Protein-Y—}(Z_1)_p\text{—P—}(Z_3)_s\text{—F} \quad (D-1)$$

wherein Protein, and each Y, $Z_1$, P, $Z_3$, F, p and s are defined as above, the conjugate fragment being grafted on the same site of attachment of Protein.

Representative compounds for compounds (D-1) are:

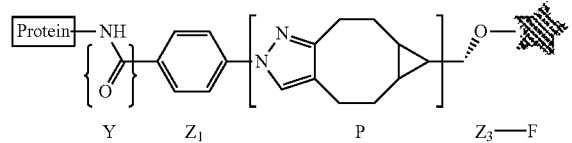

Where  represents —$Z_3$—F as defined above;

And Y is attached to an —NH— group of Protein, such as in the following compounds (D-1) and/or (D'-1):

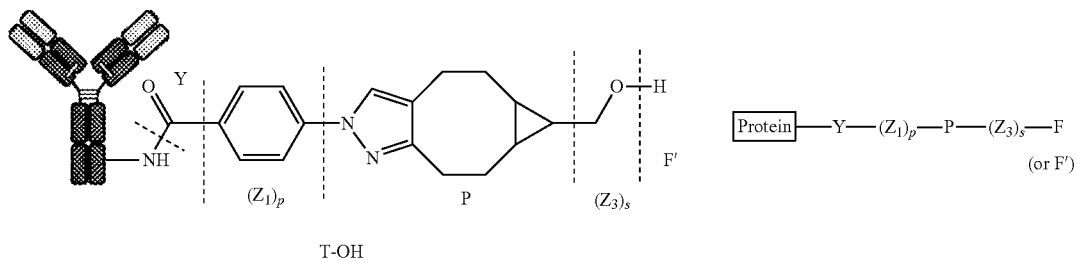

T-OH

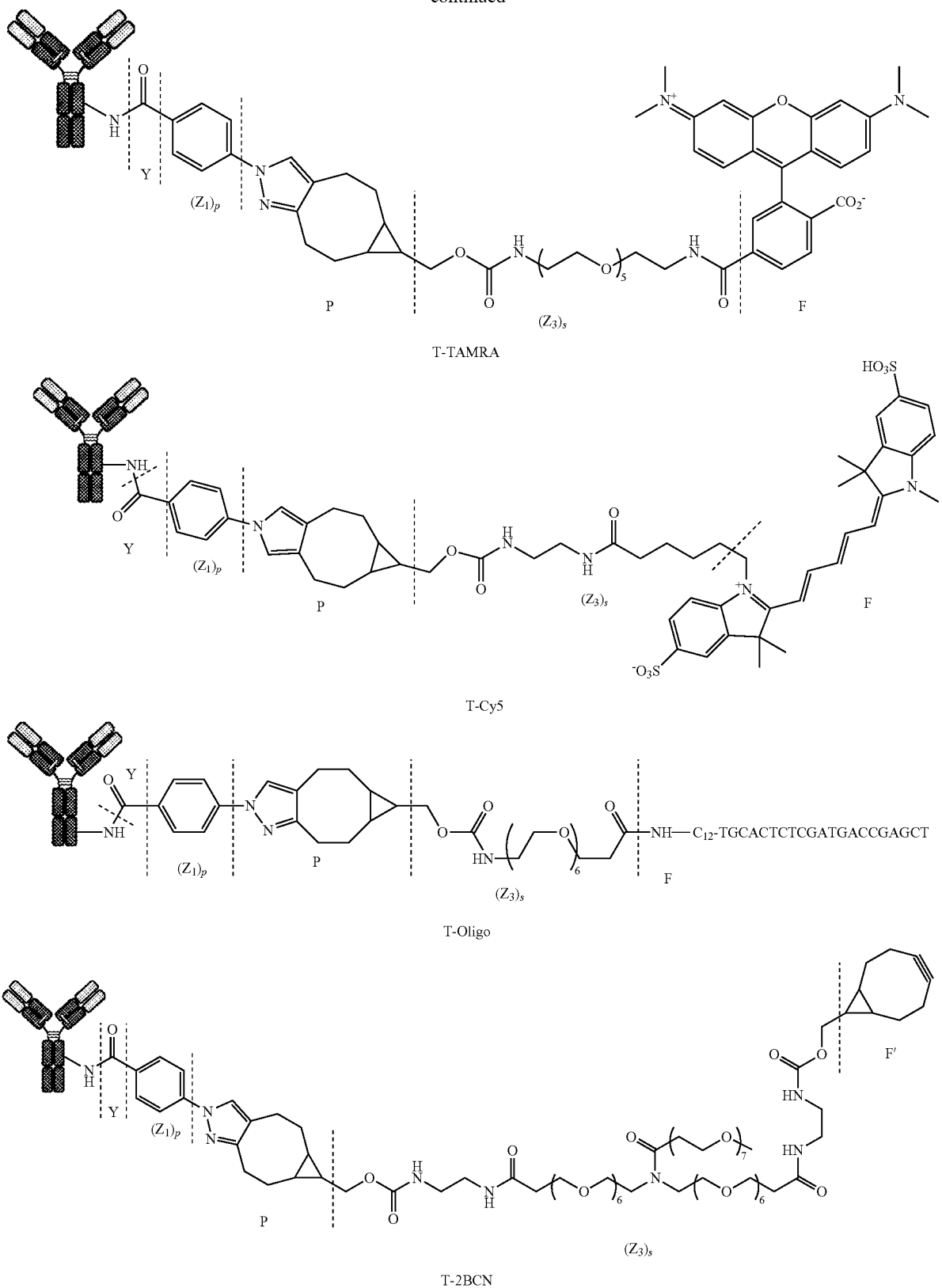
Further illustrative compounds of formula (D-1) and/or (D'-1) are disclosed in the experimental part below: examples 6, 7, 8, 12, 13, 14, 15, 16, 17, 18, 19, 20, 21, 22, 23, 24, 25, 26, 27, 28, 29, 30, 31, 32, 33, 34, 35, 36.

A further object is the process of preparation of the mixture of protein conjugates (D-n). Said process may comprise the steps of:

i) reacting Protein with a reagent of formula (I)

$$R-(Z_1)_p\text{-}T\text{-}(Z_2)_q\text{-}A \qquad (I)$$

wherein:
Protein is defined as above;
R is a chemical function reactive towards amino acid residues present in Protein under aqueous conditions;
$Z_1$ and $Z_2$ are optional spacer units independently selected from the group consisting of a C6-C12 arylene; a linear or branched, saturated or unsaturated, $C_1$-$C_{60}$ alkylene group optionally interrupted and/or terminated by one or more chemical groups selected from —O—, —S—, —S(O)—, —SO2-, —O—P(O)(OH)—O—, —C(O)—, —NH—, —C(O)NH—, —NHC(O)—, —C(O)NR$_4$—, —NR$_4$C(O)—, heteroarylene, arylene, glycosyl, an —O—(CH$_2$—CH$_2$—O—)$_r$—, —NH—(CH$_2$—CH$_2$O—)$_r$—, —(—O—CH$_2$—CH$_2$)$_r$— or —(CH$_2$—CH$_2$—O—)$_r$— groups, and an amino acid or peptide residue;
in which r is an integer ranging from 1 to 24, and
where R$_4$ is a solubility unit selected from the group consisting of C1-C6 alkylene, where one or more H is/are substituted by any of the following fragments:

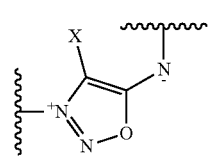

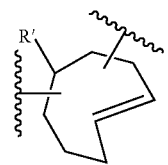

p and q are independently 0 or 1;
A is an affinity unit appropriate for immobilization of the compound of formula (I) on an affinity solid phase;
T is a trans-tagging unit preferably selected from the group consisting in:

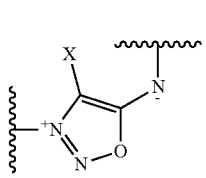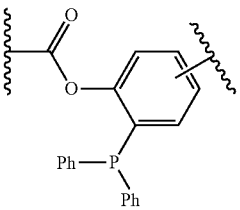

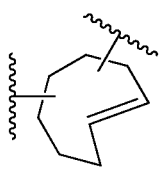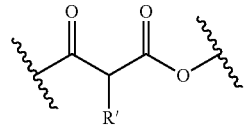

In particular in:

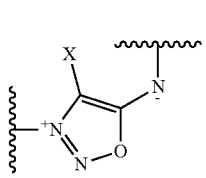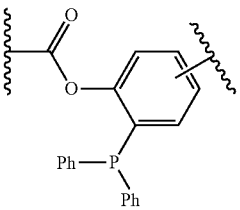

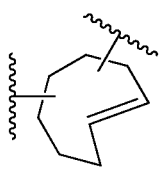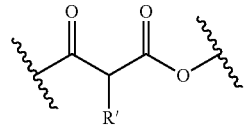

wherein X is selected from H, F, Cl, Br, I, and R' is selected from —H, saturated or unsaturated, $C_1$-$C_{60}$ alkyl group optionally interrupted by one or more chemical groups selected from —O—, —S—, —S(O)—, —SO2-, —O—P(O)(OH)—O—, —C(O)—, —NH—, —C(O)NH—, —NHC(O)—, —C(O)NR$_4$—, —NR$_4$C(O)—, heteroarylene, arylene, glycosyl, an —O—(CH$_2$—CH$_2$—O—)$_r$ or —NH—(CH$_2$—CH$_2$—O—)$_r$ groups in which r is an integer ranging from 1 to 24; and an amino acid or peptide residue,
at low conversion to yield a conjugate of formula (E-1):

$$\text{Protein-Y}-(Z_1)_p\text{-}T\text{-}(Z_2)_q\text{-}A \qquad (E\text{-}1)$$

where Protein, Y, $Z_1$, T, $Z_2$, A, p and q are defined as above;
ii) loading the conjugates of formula (E-1) on an affinity column (B) comprising said affinity solid phase;
iii) optionally recycling Protein which has not reacted in step i) into step i);
iv) subjecting the affinity column (B) loaded with the conjugates of formula (E-1) to a trans-tagging reaction with a trans-tagging reagent of formula (II):

$$C-(Z_3)_s-F' \qquad (II)$$

wherein
C is a bio-orthogonal chemical function exclusively reactive towards the T function in the reactional mixture,
s and $Z_3$ are defined as above; and
F' is H or the F group or any bio-orthogonal function, such as
an azide group;
an optionally substituted 1,2,4,5-tetrazine;
an optionally substituted trans-cyclooctene
a C7-C9 cycloalkynyl derivative optionally interrupted by one or more chemical groups selected from —O—, —S—, —S(O)—, —SO2-, —O—P(O)(OH)—O—, —C(O)—, —NH—, —C(O)NH—; and/or optionally fused with a C3 to C6 cycloalkyl or phenyl;
a hydrazine group;
an aldehyde group;
an —O—NH$_2$ group
a OH group;
a COOH group;
a thiol group
an arylpropiolonitrile group;
a benzocyclooctynyl or dibenzocyclooctynyl derivative, optionally interrupted by one or more chemical groups selected from —O—, —S—, —S(O)—, —SO2-, —O—P(O)(OH)—O—, —C(O)—, —N—, —NH—, —C(O)NH—, and/or optionally substituted by one or more halogen atoms, =O; typically from the group consisting in:

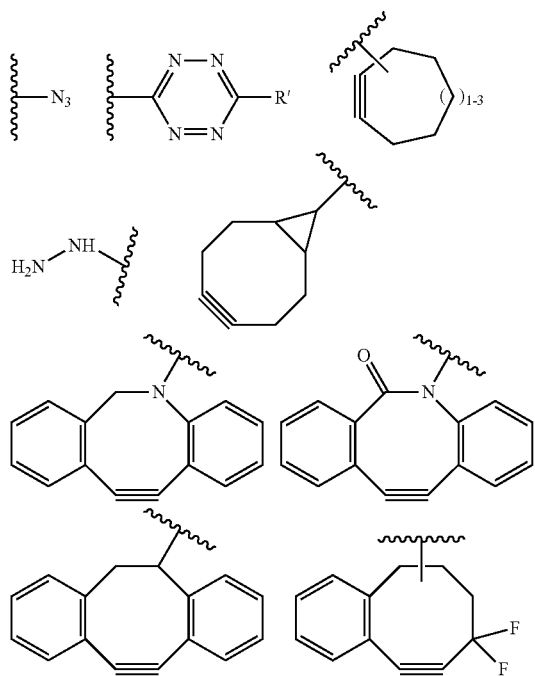

where R' is selected from —H, saturated or unsaturated, C$_1$-C$_{60}$ alkyl group optionally interrupted by one or more chemical groups selected from —O—, —S—, —S(O)—, —SO2-, —O—P(O)(OH)—O—, —C(O)—, —NH—, —C(O)NH—, —NHC(O)—, —C(O)NR$_4$—, —NR$_4$C(O)—, heteroarylene, arylene, glycosyl, an —O—(CH$_2$—CH$_2$—O—)$_r$ or —NH—(CH$_2$—CH$_2$—O—)$_r$ groups in which r is an integer ranging from 1 to 24; and an amino acid or peptide residue, where R$_4$ is defined as above,
in particular:
F' is the F group or any bio-orthogonal function, such as
  an azide group;
  an optionally substituted 1,2,4,5-tetrazine;
  an optionally substituted trans-cyclooctene
  a C7-C9 cycloalkynyl derivative optionally interrupted by one or more chemical groups selected from —O—, —S—, —S(O)—, —SO2-, —O—P(O)(OH)—O—, —C(O)—, —NH—, —C(O)NH—; and/or optionally fused with a C3 to C6 cycloalkyl;
  a hydrazine group;
  an aldehyde group;
  an —O—NH$_2$ group
  a thiol group
  an arylpropiolonitrile group;
  a benzocyclooctynyl or dibenzocyclooctynyl derivative, optionally interrupted by one or more chemical groups selected from —O—, —S—, —S(O)—, —SO2-, —O—P(O)(OH)—O—, —C(O)—, —N—, —NH—, —C(O)NH—, and/or optionally substituted by one or more halogen atoms, =O; typically from the group consisting in:

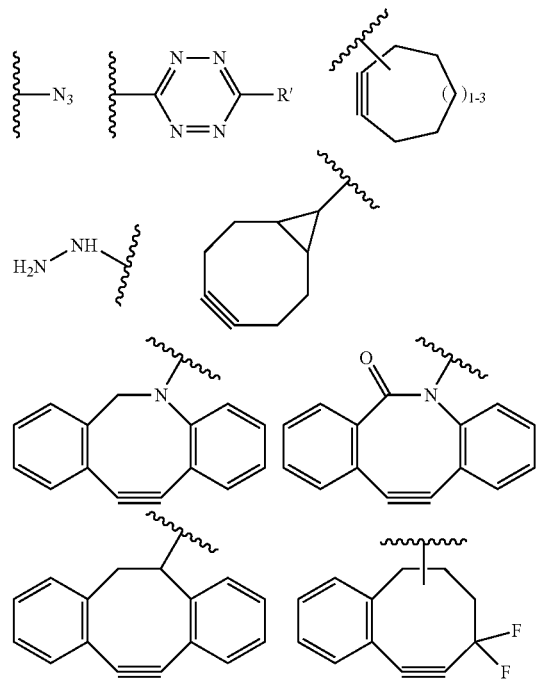

where R' is selected from —H, saturated or unsaturated, C$_1$-C$_{60}$ alkyl group optionally interrupted by one or more chemical groups selected from —O—, —S—, —S(O)—, —SO2-, —O—P(O)(OH)—O—, —C(O)—, —NH—, —C(O)NH—, —NHC(O)—, —C(O)NR$_4$—, —NR$_4$C(O)—, heteroarylene, arylene, glycosyl, an —O—(CH$_2$—CH$_2$—O—)$_r$ or —NH—(CH$_2$—CH$_2$—O—)$_r$ groups in which r is an integer ranging from 1 to 24; and an amino acid or peptide residue, where R$_4$ is defined as above.

So as to simultaneously form and release from the affinity column the conjugate of formula (D'-1):

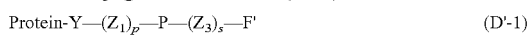

Protein-Y—(Z$_1$)$_p$—P—(Z$_3$)$_s$—F'     (D'-1)

wherein Protein, Y, Z$_1$, p, s, F' and Z$_3$ are defined as above;
  v) optionally repeating steps i) to iv) above with same or different compounds (I) and/or (II) so as to achieve a mixture comprising protein conjugates (D'-n) having a DoC of n:

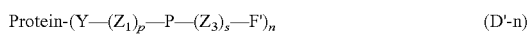

Protein-(Y—(Z$_1$)$_p$—P—(Z$_3$)$_s$—F')$_n$     (D'-n)

Wherein Y, Z$_1$, P, Z$_3$, F' p, s may be the same of different for each grafted conjugate chain;
  vi) optionally conducting where F' is different from the desired F group, a post-functionalization of the compound of formula (D'-n) by substituting and/or derivatizing in compound (D'-n) the group F' with the desired F group of formula (D-n).

According to an embodiment, Z$_1$ is a phenyl group.
According to an embodiment, R is chosen from the group consisting in:

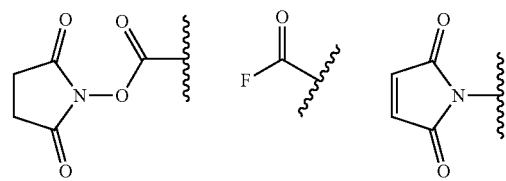

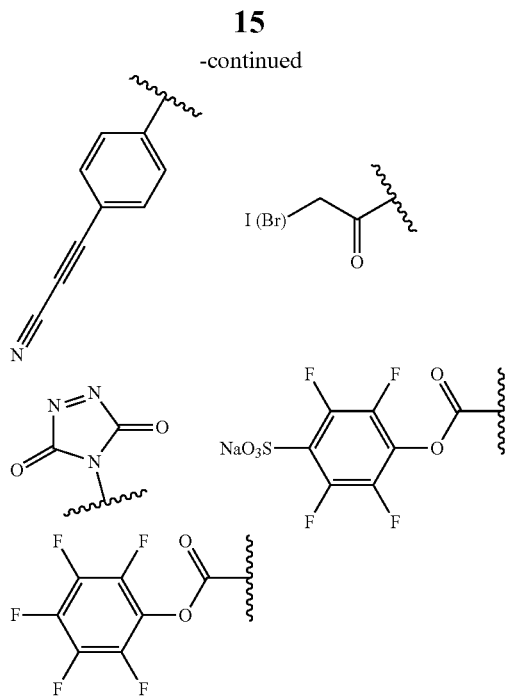

Typically, step i) is advantageously conducted at low conversion, meaning that a conversion of less than 40%, typically, less than 30%, particularly less than about 20% of Protein is reacted. This may be typically achieved by reacting an excess of Protein respective to the reagent of formula (II).

According to an embodiment, C is selected is selected from the group consisting in:
- an azide group;
- an optionally substituted 1,2,4,5-tetrazine;
- an optionally substituted trans-cyclooctene
- a C7-C9 cycloalkynyl derivative optionally interrupted by one or more chemical groups selected from —O—, —S—, —S(O)—, —SO2-, —O—P(O)(OH)—O—, —C(O)—, —NH—, —C(O)NH—; and/or optionally fused with a $C_3$ to $C_6$ cycloalkyl;
- an —NH—NH$_2$;
- a benzocyclooctynyl or dibenzocyclooctynyl derivative, optionally interrupted by one or more chemical groups selected from —O—, —S—, —S(O)—, —SO2-, —O—P(O)(OH)—O—, —C(O)—, —N—, —NH—, —C(O)NH—, and/or optionally substituted by one or more halogen atoms, =O;

typically from the group consisting in:

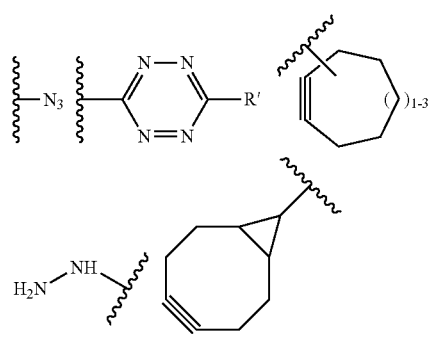

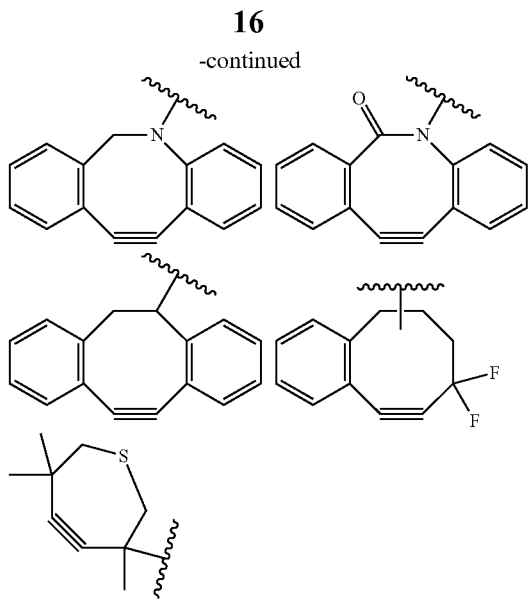

in particular in:

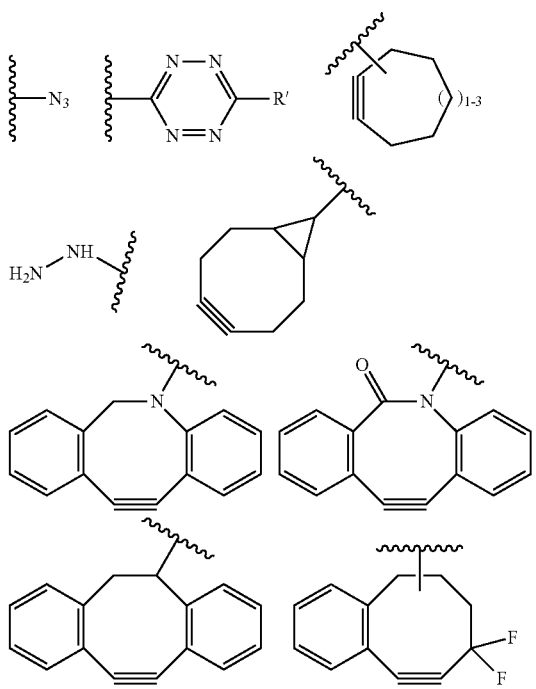

where R' is selected from —H, saturated or unsaturated, $C_1$-$C_{60}$ alkyl group optionally interrupted by one or more chemical groups selected from —O—, —S—, —S(O)—, —SO2-, —O—P(O)(OH)—O—, —C(O)—, —NH—, —C(O)NH—, —NHC(O)—, —C(O)NR$_4$—, —NR$_4$C(O)—, heteroarylene, arylene, glycosyl, an —O—(CH$_2$—CH$_2$—O—)$_r$ or —NH—(CH$_2$—CH$_2$—O—)$_r$ groups in which r is an integer ranging from 1 to 24; and an amino acid or peptide residue, where R$_4$ is defined as above.

According to an embodiment, Z$_2$ is a C1-C6 alkyl chain interrupted and/or terminated by one or more chemical groups selected from —O—, —C(O)—, —NH—, —(—O—CH$_2$—CH$_2$)$_r$ or —(CH$_2$—CH$_2$—O—)$_r$— groups, in which r is an integer ranging from 1 to 24

A is an affinity function suitable for binding a specific non-covalent interaction with a complementary affinity function, appropriate for solid phase immobilization.

Typically, A can be a biotin or a DTB (D-desthiobiotin).

The affinity solid phase of the column comprises but is not limited to streptavidin or avidin functions, typically streptavidin functions.

According to an embodiment, $Z_3$ is a C1-C6 alkyl chain interrupted and/or terminated by one or more chemical groups selected from —O—, —C(O)—, —NH—, —(—O—CH$_2$—CH$_2$)$_r$ or —(CH$_2$—CH$_2$—O—)$_r$— groups, in which r is an integer ranging from 1 to 24.

According to an embodiment, steps i), ii) and iii), in particular step i) may be repeated several times with the obtained mixture comprising the compound (E-1) and with Protein, to increase the rate of conversion, typically from 5 to 50 times.

It is also understood that the trans-tagging reaction of step iv) may be carried out with a compound of formula (E-1) with a compound of formula (D'-1) as a trans-tagging reagent. Therefore, according to an embodiment the compound of formula (II) may be a compound of formula (D'-1).

The Protein that has not reacted can be recycled in this repeated step i).

In step ii), the term "trans-tagging" as used herein refers to a reaction comprising a simultaneous functionalization and release of the reacted species.

More precisely, the term "trans-tagging" as used herein refers to a bioorthogonal substitution reaction comprising a simultaneous coupling and release of the molecular fragments (schematically, A–B+C=A–C+B; wherein occurs a substitution of B by C, i.e. simultaneous coupling of A with C and release of B). More precisely, compound (E-1) reacts with compound (II) so as to form compound (D-1), which is released from the solid phase. This is made possible by the presence in compound (E-1) and (II) of the two functions T and C respectively present in compound (E-1) and (II) and that are reactive towards each other in a selective way.

More precisely, compound (E-1) reacts with compound (II) so as to form compound (D-1), which is released from the solid phase. This is made possible by the presence in compound (E-1) and (II) of the two functions T and C respectively present in compound (E-1) and (II) and that are reactive towards each other in a selective way. In particular, they are bio-orthogonal and are not reactive towards Protein.

According to an embodiment, T is

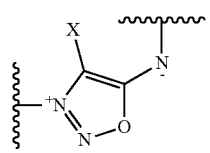

where X is H, and C is

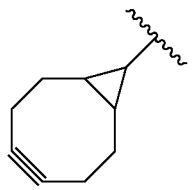 [SMILES: *C1C2CCC#CCCC12]

The following reactions illustrate representative trans-tagging reactions. In the schemes below, the reactions are given for compounds of formula (E-I) and (II) where p=q=s=0 and Y is absent for illustrative purposes:

a) Staudinger trans-tagging

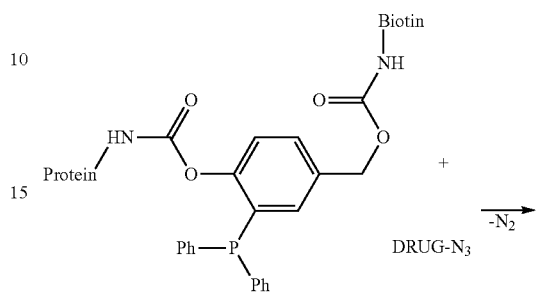

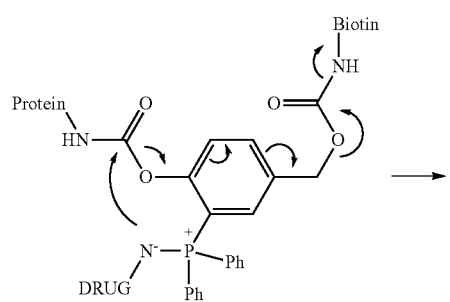

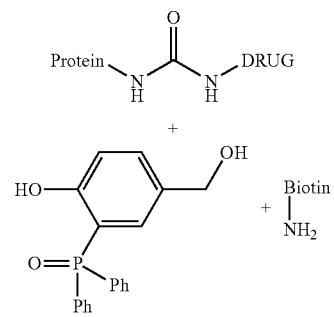

b) Tetrazine trans-tagging

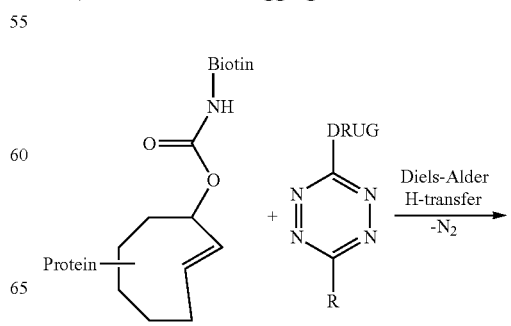

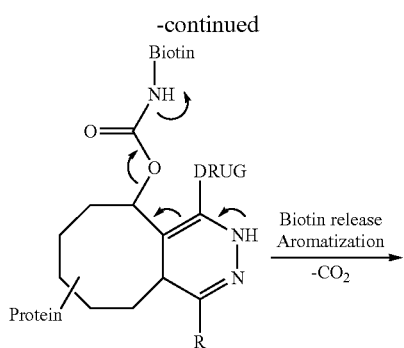
c) Iminosydnone trans-tagging
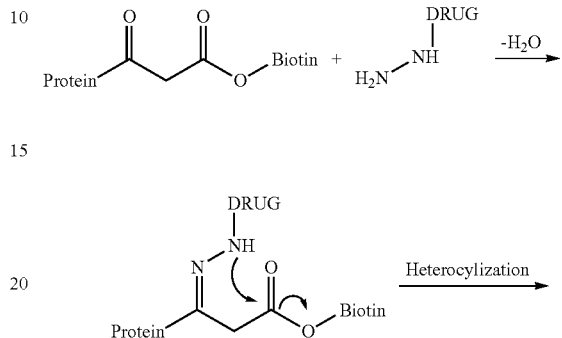
d) Hydrazine trans-tagging
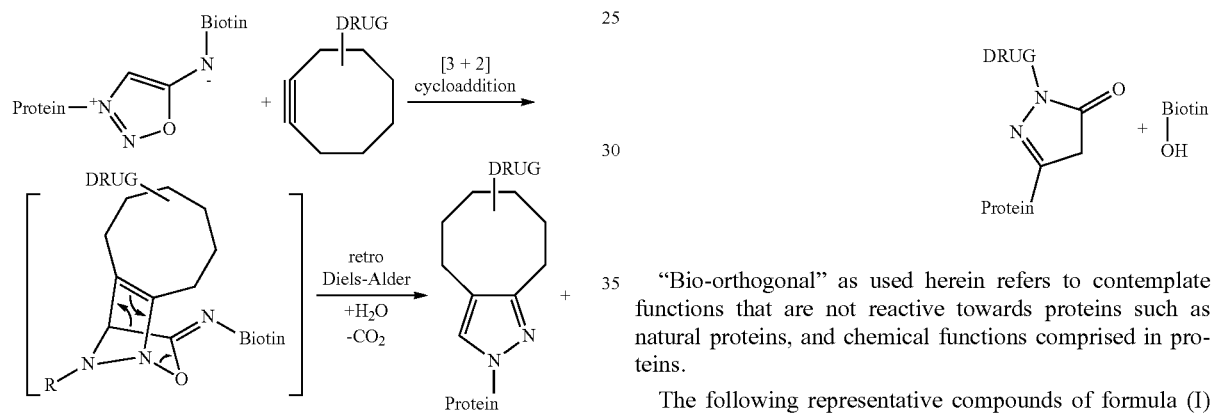
"Bio-orthogonal" as used herein refers to contemplate functions that are not reactive towards proteins such as natural proteins, and chemical functions comprised in proteins.
The following representative compounds of formula (I) may be cited:
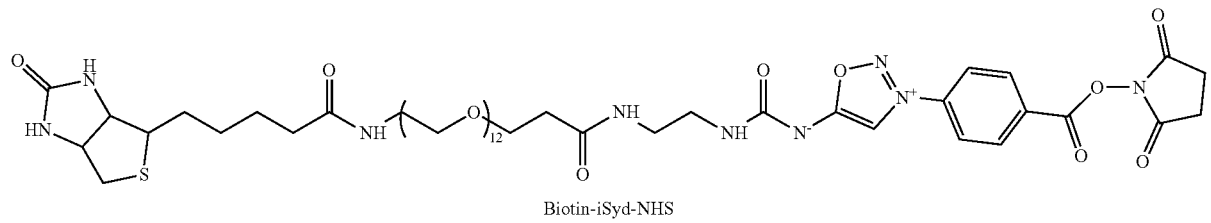
Biotin-iSyd-NHS
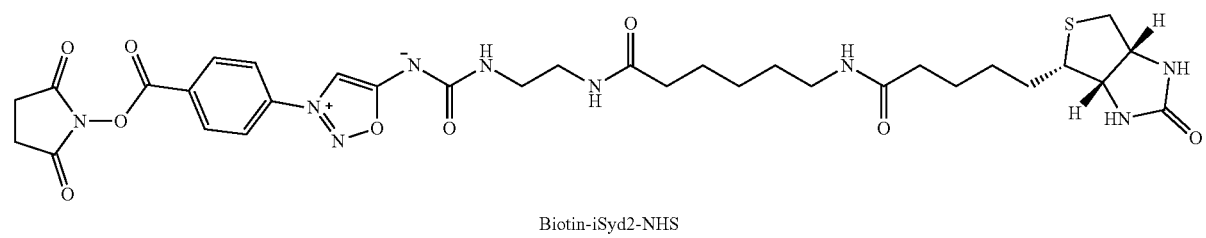
Biotin-iSyd2-NHS

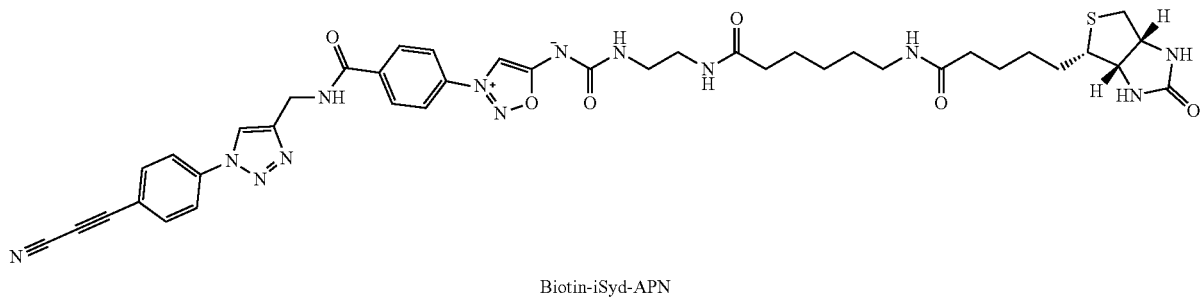
Biotin-iSyd-APN
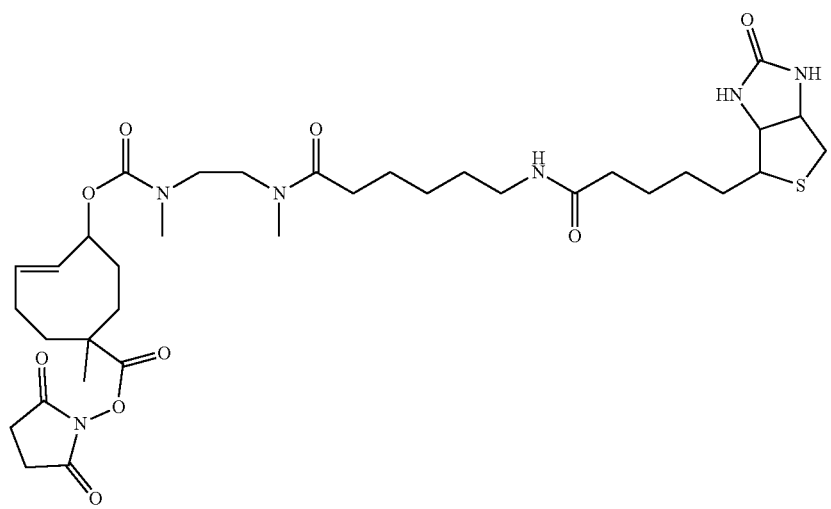
Biotin-TCO-NHS
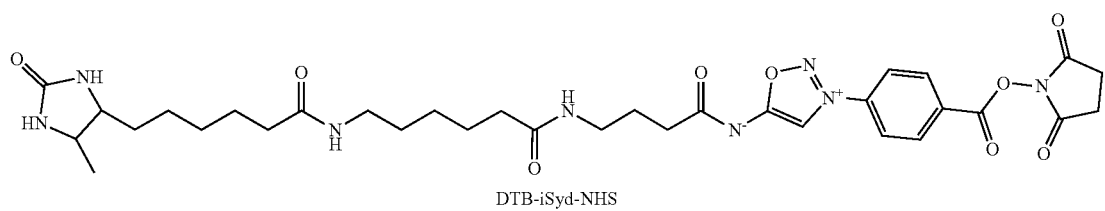
DTB-iSyd-NHS
Illustrative reagents (II) used in step iv) are:
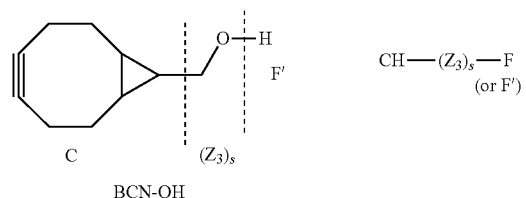
BCN-OH -continued
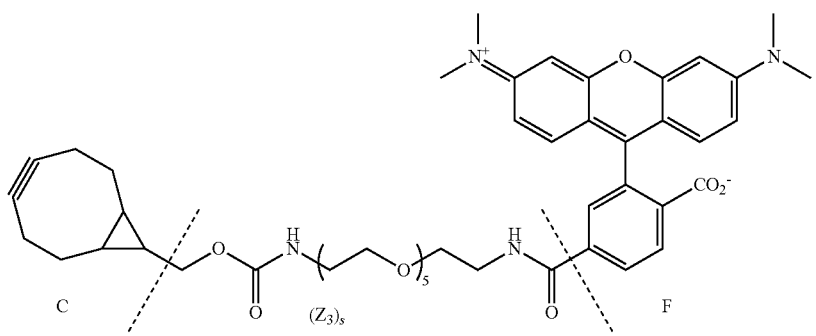
BCN-TAMRA
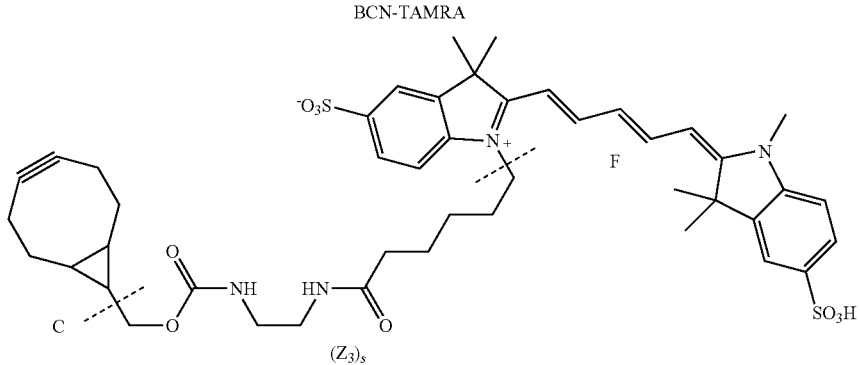
BCN-Cy5
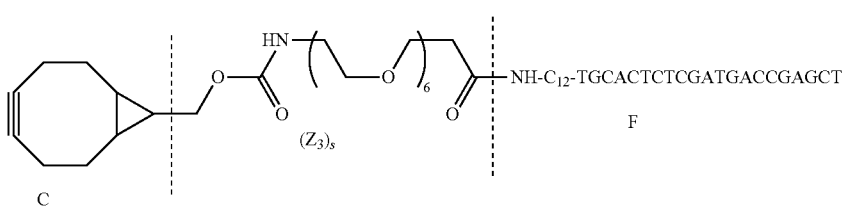
BCN-Oligo
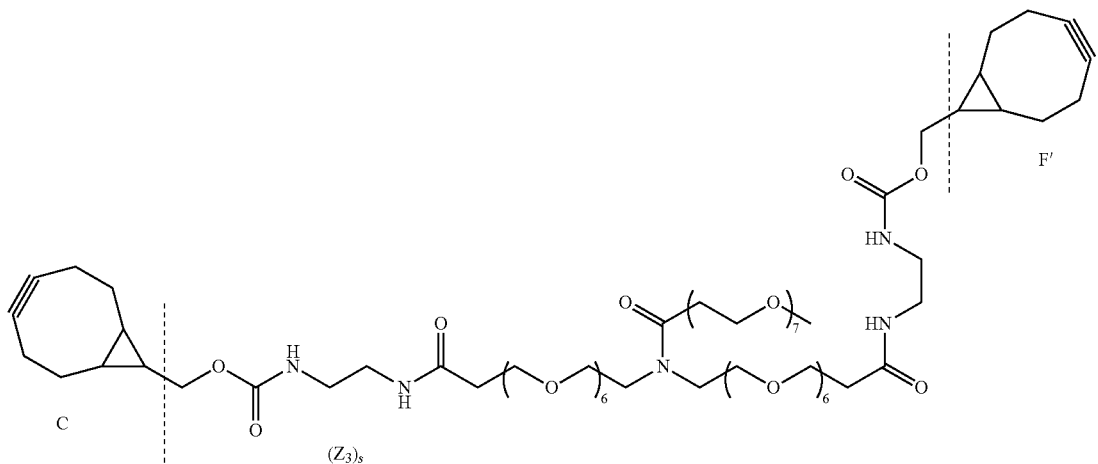
2BCN As well as the following compounds of formula (II):

TMTH, DBCO-PEG, DBCO-MMAF, BCN-MMAE, BCN-MMAF, di-BCN, DBCO-MMAE, DBCO—COOH, Me-Tz-Cy5, BCN-TAMRA, BCN-doxorubicin, compound 17, whose formula are depicted in the experimental part below.

In step v), the process can be repeated one or more times with same or different compounds (I) and/or (II).

Different protein conjugates (D-n) with different conjugate fragments (G) can be generated and introduced into the mixture by running the process of the invention with different reagents of formula (I) and/or (II), provided that compounds (I) and (II) respectively comprise complementary T and C groups.

If the same reagents (I) and (II) are used, respectively for each cycle the mixture will contain protein conjugates (D-n) having the same conjugate fragment (G) as defined above.

If the process is repeated (n-1) times starting with the compound of formula (D'-(n-1)) with the same compounds (I) and (II), respectively, for each cycle, this will result in the protein conjugate (D'-n):

Protein-(Y—($Z_1$)$_p$—P—($Z_3$)$_s$—F')$_n$     (D'-n)

Wherein Y, $Z_1$, P, $Z_3$, F' p, s are respectively the same;

Said protein conjugate having all the same conjugate fragment (G) with a DoC of n.

The process should be ran altogether n times with the same reagents (I) and (II) to achieve protein conjugates having the conjugate fragment (G) with a DoC of n.

As an illustration:

The heterogeneous monodisperse mixtures of protein conjugates having a conjugate fragment with DoC=2 can be generated by applying the process of the invention one more time to the protein conjugates (D-1) with the same reagents (I) and (II).

Similarly, the heterogeneous monodisperse mixtures of protein conjugates with DoC=3 can be generated by applying the process of the invention to (D-2), and the heterogeneous monodisperse mixtures of protein conjugates with DoC=4 can be generated by applying the process of the invention to (D-3), with the same reagents (I) and (II).

In step vi), post-functionalization (ie) chemical derivatization or substitution of the F' groups can be conducted, if appropriate. This may be typically achieved by reacting the compound (D'-n) with the appropriate reagents allowing to transform and/or substitute F' into F. The reagents and experimental conditions may be generally adapted from the known procedures, such as those disclosed in Larock, Wiley and Sons, Inc (Comprehensive organic transformations: A guide to functional group preparations). Additionally, protecting groups may be introduced/substituted by application or adaptation of the groups/procedures disclosed in McOmie "Protective groups in organic chemistry. Plenum Press, 1973 or "Greene's Protective groups in organic synthesis (Greene et al., Wiley and Sons Inc., 2006).

Illustrative trans-tagging and post-functionalization reactions are illustrated below:

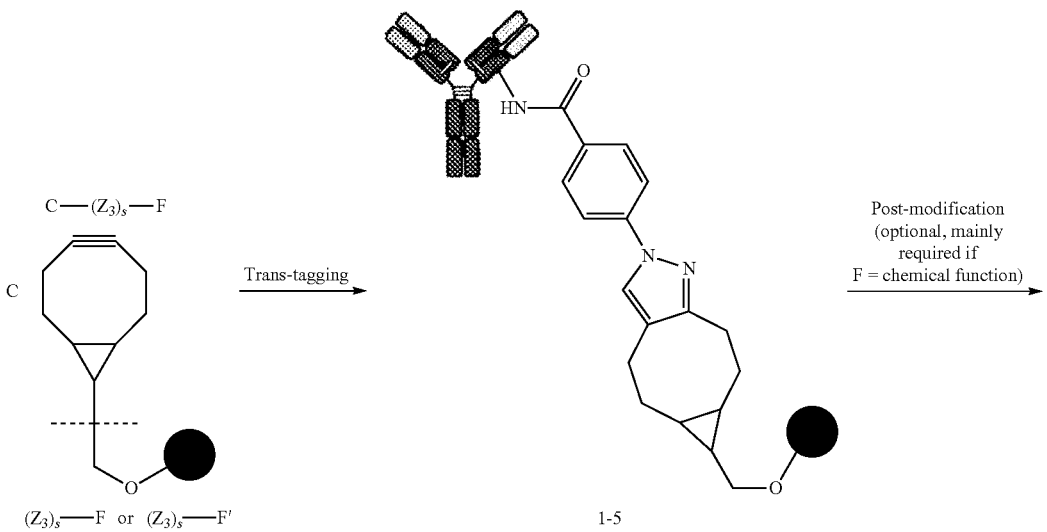

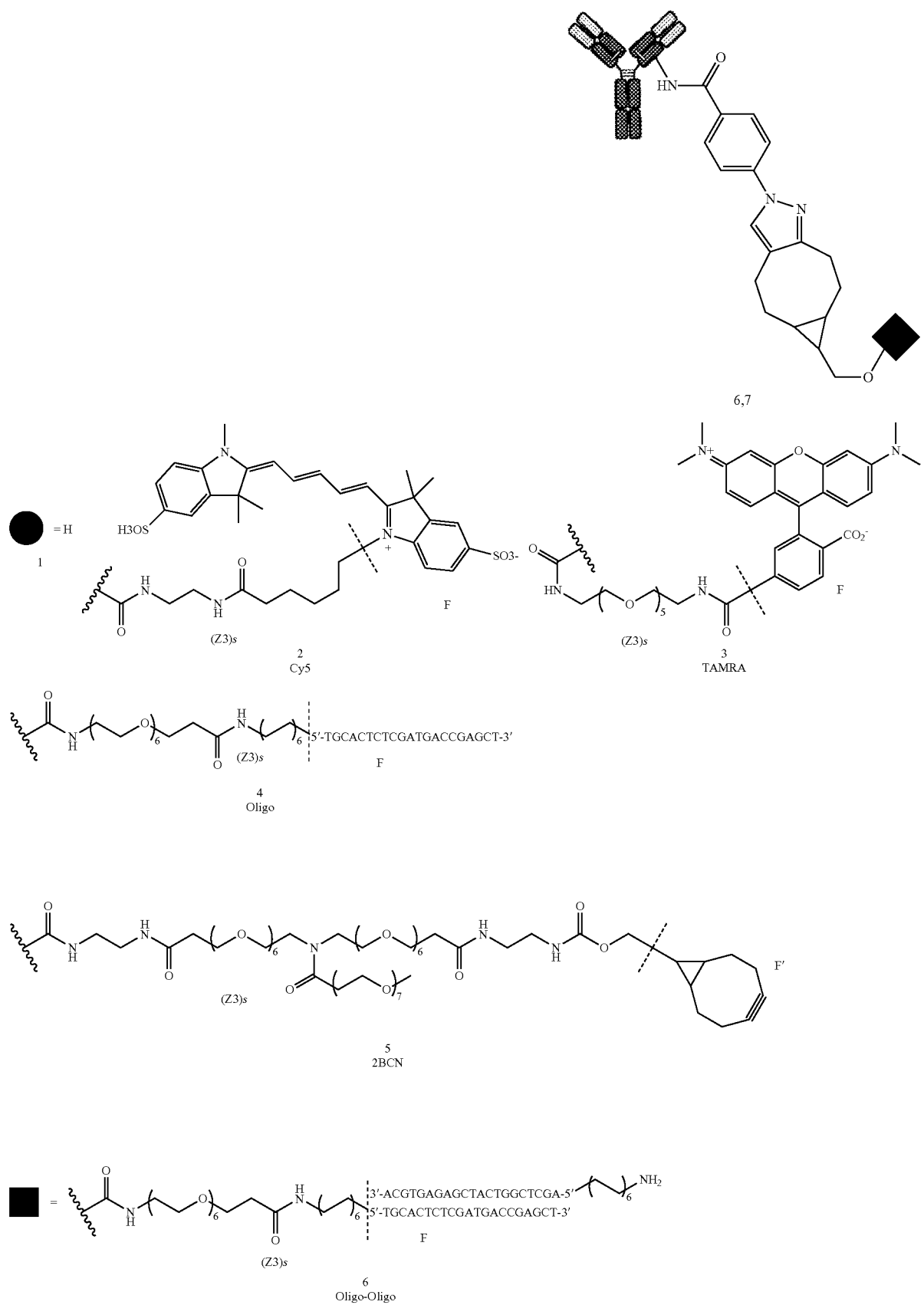

-continued

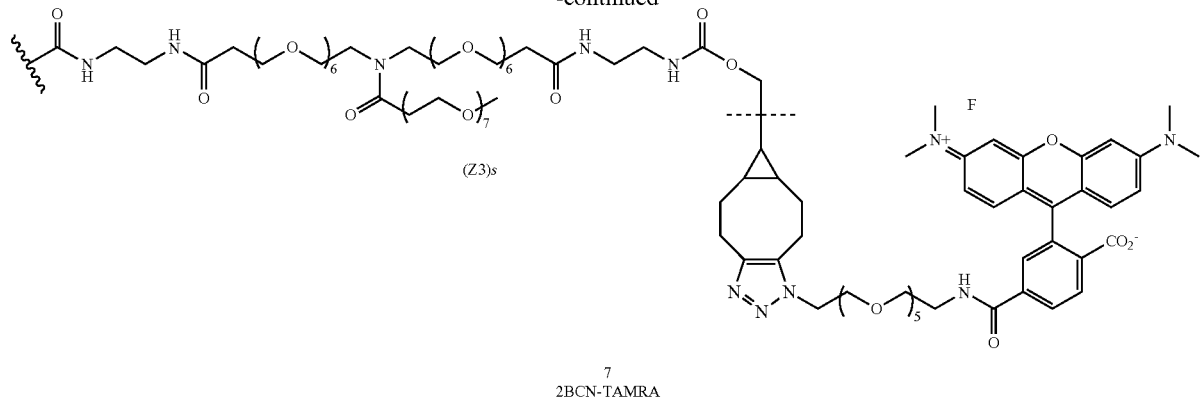

7
2BCN-TAMRA

A further object of the invention is the tri-functional reagent having the following formula (I):

$$R-(Z_1)_p\text{-}T\text{-}(Z_2)_q\text{-}A \qquad (I)$$

wherein:
$Z_1$, $Z_2$, T, A, R, p and q are defined as above.
A representative compound of formula (I) is:

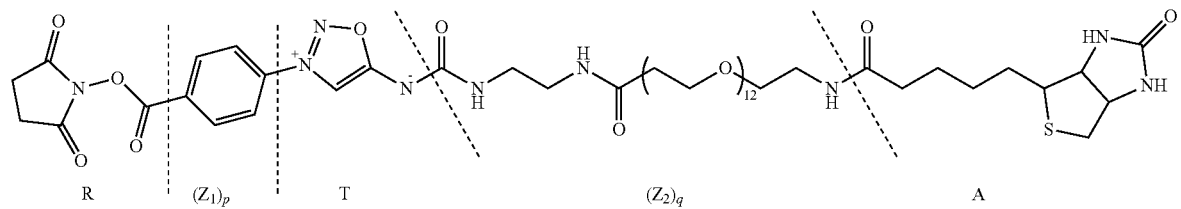

A further object of the invention is a kit comprising a compound of formula (I) of the invention, with a compound of formula (II) of the invention, and an optional affinity column as defined above.

A further object of the invention is the compound of formula (E-1):

$$\text{Protein-Y}-(Z_1)_p\text{-}T\text{-}(Z_2)_q\text{-}A \qquad (E\text{-}1)$$

where Protein, Y, $Z_1$, T, $Z_2$, A, p and q are defined as above.
Representative compounds of formula (E-1) are:

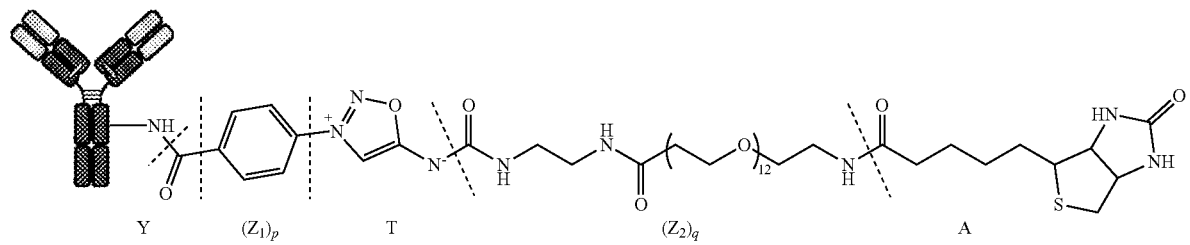

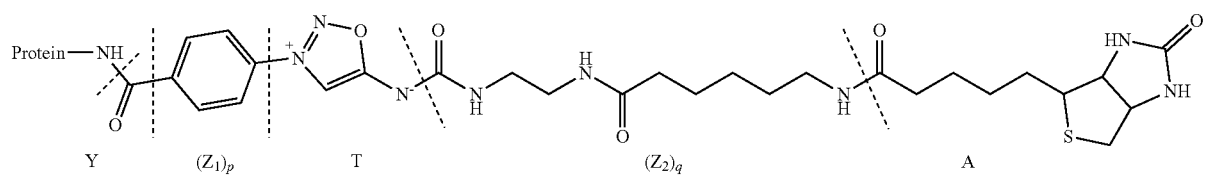

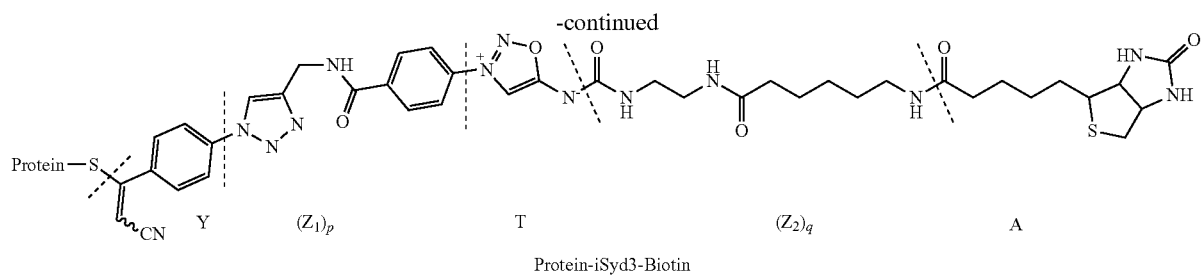

Protein-iSyd3-Biotin

According to an embodiment, the invention is such that it comprises conjugates where F is an antineoplasic agent or a cytotoxic drug and Protein is a monoclonal antibody targeting tumor cells, for use for treating cancer.

According to a further object, the present invention thus also concerns the mixture of protein conjugates as defined above typically, where F is an antineoplasic agent or a cytotoxic drug and Protein is a monoclonal antibody targeting tumor cells, for use for treating cancer.

FIGURES

FIG. 1 illustrates the process of the invention for preparing a mixture of conjugate of formula (D-n), where n is 1. In FIG. 1:
Step (i) represents the conjugation of a Protein with a compound of formula (I) at low conversion;
Step (ii) illustrates the loading of the formed conjugate of formula (E-1) on the affinity column;
Step (iii) is the recycling of the unreacted Protein into the step (i);
Step (iv) is the trans-tagging reaction of the conjugate (iv) with a compound (II) so as to form the conjugate (D'-n);
followed by optional post-functionalization into conjugate (D-n) if F' is different from F.

Figure 2:
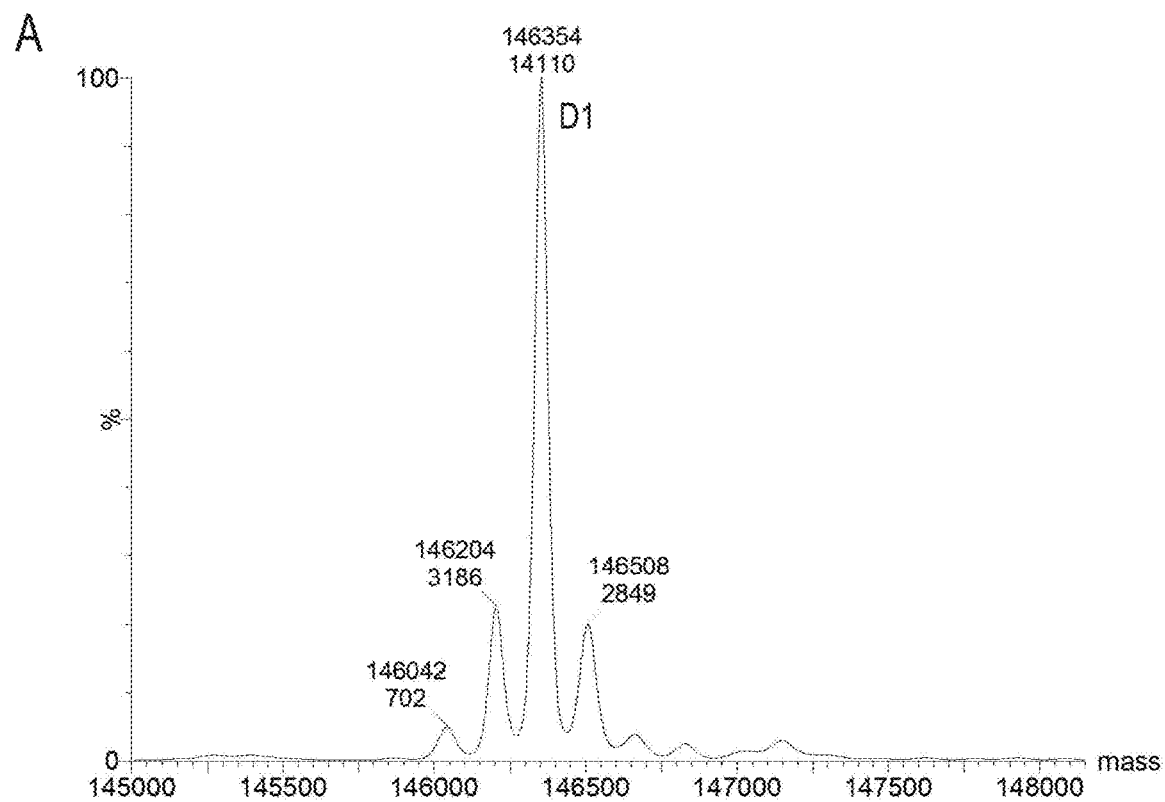
Figure 2:
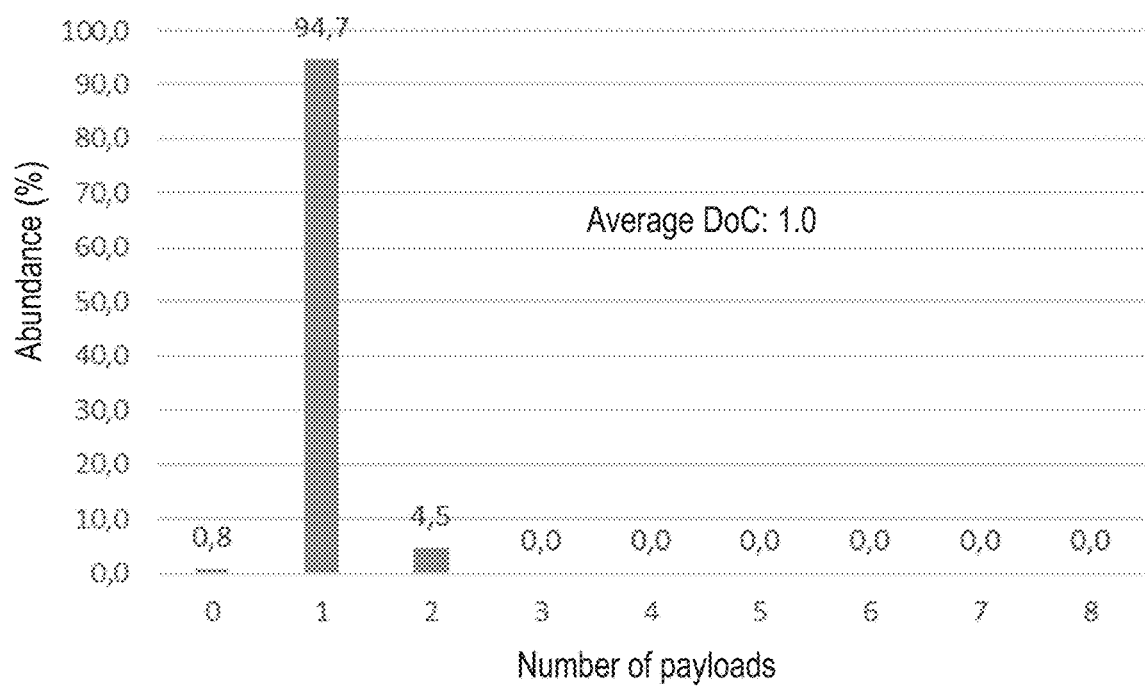
Figure 2:
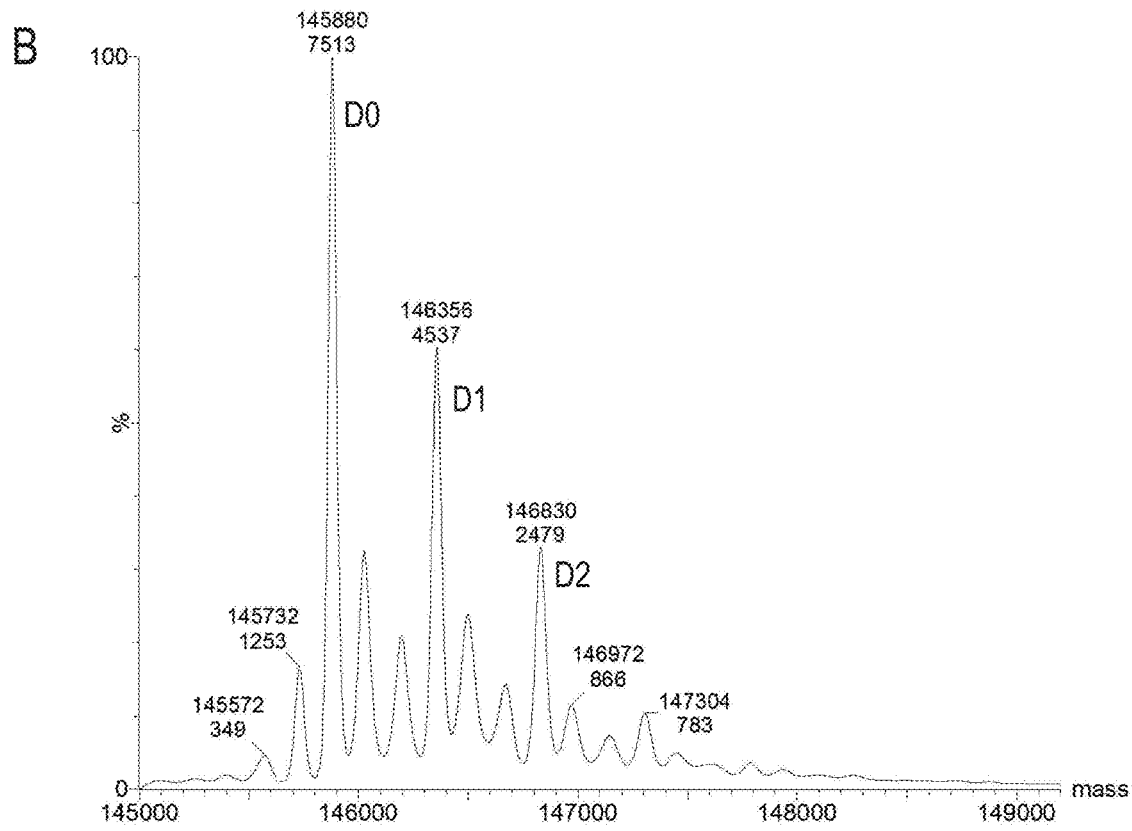
Figure 2:
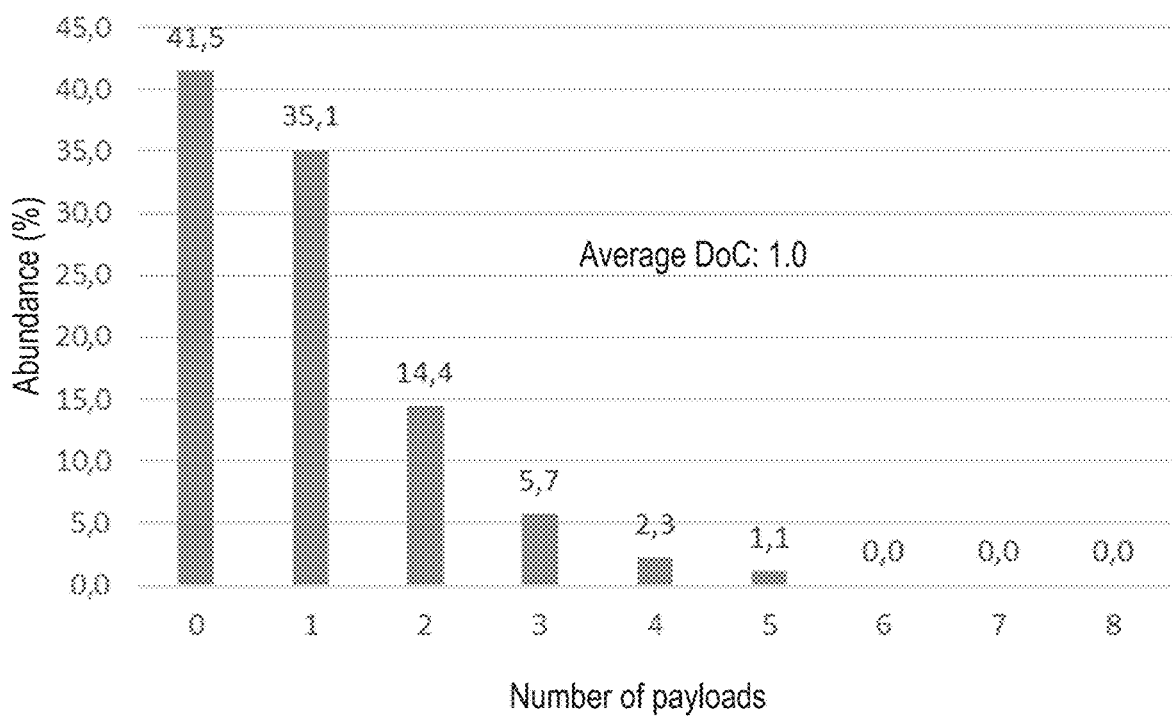

FIG. 2 illustrates the comparison of the process of the invention with the plug-and-play process disclosed by Dovgan et al (Bioconjugate Chemistry, 2017, vol. 28, pages 1452-1457): A) shows the representative mass spectrum of compound 8 obtained via the DARX process of the invention and B) shows the representative mass specturum of compound 8 obtained via the plug-and-play process.

EXAMPLES

All reagents were obtained from Sigma Aldrich (St. Louis, MO, USA), or prepared using procedures described in literature. Organic solvents were obtained from Sigma Aldrich (St. Louis, MO, USA) and used without further purification.

Method 1—ESI-MS

The ESI-MS was run on Waters 2695 separations module equipped with Waters 2487 UV detector, Waters Acquity QDa mass detector and CORTECS, 2.7 µm, C18, 50×4.6 mm column. The flow rate was 1 ml/min. Solvent A: 0.05% HCOOH in water. Solvent B: 0.05% HCOOH in acetonitrile. Gradient run: 0-5 min—5% to 95% B; 5-6 min—95% B; 6-7.8 min—5% B. Mass detector was operated in positive MS Scan mode with 600° C. probe temperature, 1.5 kV capillary voltage and 10 V cone voltage.

Example 1: Preparation of a Compound of Formula (I): Preparation of Biotin-iSyd-NHS

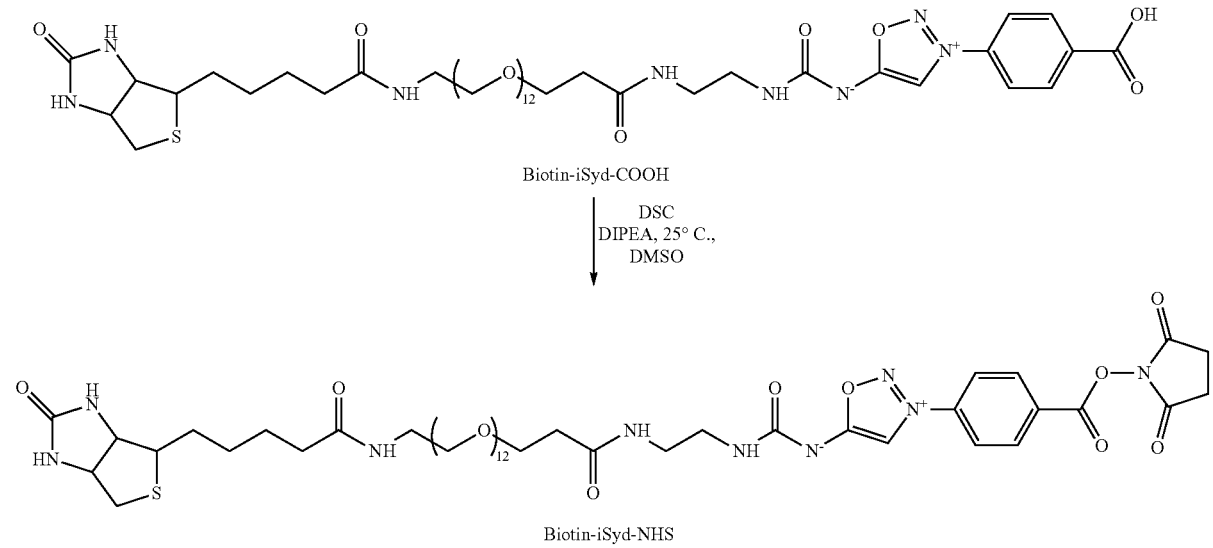

To a solution of Biotin-iSyd-COOH (1 eq., 80 µL, 10 mM in DMSO) was added DIPEA (10 eq., 1.39 µL) followed by disuccinimide carbonate (40 eq., 0.5 M in DMSO, 32×2 µL) at 25° C. The reaction mixture was maintained at 25° C. overnight. Aliquot of the reaction mixture was analyzed by le;2qLCMS confirming 50-80% of conversion. The organic solvent was then evaporated and 90 µL of ACN was added. The sample (90 µL injection) was purified by HPLC (15 min run, detection at 254 nm; buffer A: H₂O miliQ+0.05% of TFA; buffer B: ACN; 10 min—from 5% to 95% B, 2 min—95% B, 3 min—5% B). The collected fraction was promptly lyophilized and the resulting product, Biotin-iSyd-NHS, was dissolved in 80 µL of dry DMSO to afford 8.2 mM stock solution (concentration evaluated by LCMS using a calibration curve of Biotin-iSyd-COOH).

Example 2: Bioconjugation 2.1 General Procedure a for the Preparation of Protein Conjugates (D-n) with Defined Degree of Conjugation This comprises three parts:
Part I. Preparation of antibody conjugates (E-1) with affinity tag in low conversion
Part II. Loading of antibody conjugates (E-1) into the affinity column
Part III. Trans-tagging reaction 2.1.1 Part I. Preparation of Antibody-iSyd-Biotin Conjugates (E-1):

antibody were collected and concentrated on using Vivaspin 20 centrifugal filtration unit (MWCO 30 kD, Sartorius) for use in subsequent cycles.

2.1.3 Part III. Trans-Tagging Reaction

Trans-tagging reaction was performed in the streptavidin column using as compound of formula (II) bicyclononyne (BCN) derivatives bearing fluorophores (TAMRA, Cy5), oligonucleotide or BCN as secondary functionality. The column was equilibrated with the solution of a BCN derivative (10 µM, 5 mL in PBS 1×, pH 7.4 containing 5% of DMSO) at flow rate of 1 mL/min. The column was incubated at 25° C. for 24 h and then eluted with PBS 1× (pH 7.4, 10 mL) at flow rate of 0.5 mL/min using ÄKTA Pure chromatography system (GE Healthcare Life Sciences). The collected fraction of the functionalized antibody conjugate was concentrated using Vivaspin 500 centrifugal filtration unit (MWCO 50 kD, Sartorius) and then purified by gel filtration chromatography on Bio-Spin P-30 Columns (Bio-Rad, Hercules, USA) equilibrated with PBS 1× (pH 7.4). The general yield was 150-500 µg of antibody conjugates per trans-

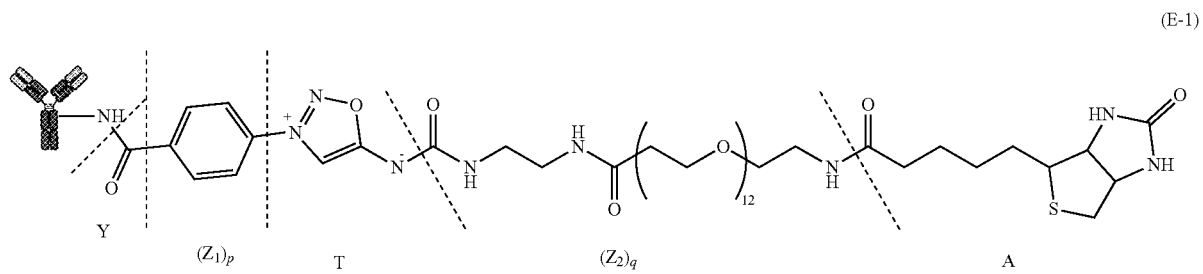

(E-1)

DMSO (15 µL) followed by Biotin-iSyd-NHS reagent (1 eq., 10×21 µL, 500 µM in DMSO) were added to a solution of trastuzumab (1 eq., 5 mg/mL, 3 mL in PBS 1×, pH 7.4) at 25° C. The reaction mixture was maintained at 25° C. for 2 h. The reaction mixture was washed 3 times with PBS 1× (pH 7.4) using Vivaspin 20 centrifugal filtration unit (MWCO 30 kD, Sartorius).

2.1.2 Part II. Loading of Antibody Conjugates (E-1) into the Affinity Column

Trastuzumab-iSyd-Biotin conjugate (3 mL in PBS 1×, pH 7.4) was loaded on HiTrap Streptavidin HP column (1 mL, GE Healthcare Life Sciences, Ref. 17-5112-01) equilibrated with PBS 1× (pH 7.4) using ÄKTA Pure chromatography system (GE Healthcare Life Sciences) at flow rate of 0.2 mL/min. The column was then washed with PBS 1× (pH 7.4, 0.2 mL/min, 20 CV) and the fractions of unconjugated tagging reaction. The resulting conjugates of formula (D'-1) (50 µg) were subjected to MS analysis according to General Procedure C.

2.2 General Procedure B for Post-Modification of Protein Conjugates

Protein conjugates (D'-1) (1 eq., 50 µL, 1 mg/mL in PBS 1×, pH 7.4) obtained following General Procedure A were reacted with post-modification reagent such as TAMRA-N₃ (2 eq., 1.36 µL, 0.5 mM) for 18 hours at 25° C. The conjugates (D-1) were purified by gel filtration chromatography on Bio-Spin P-30 Columns (Bio-Rad, Hercules, USA) equilibrated with PBS 1× (pH 7.4) and subjected to MS analysis according to General Procedure C.

General Procedure C for Characterization of Protein Conjugates Using Mass Spectrometry (MS)

Prior to MS experiments, antibody conjugates (ACs) were desalted against 150 mM ammonium acetate solution buffered at pH 7.4 by performing six cycles of concentration/ dilution on Vivaspin 500 centrifugal filtration units (MWCO 30 kD, Sartorius). Protein concentration was determined by UV absorbance using a NanoDrop spectrophotometer (Thermo Fisher Scientific, Illkirch, France). ADC deglycosylation was achieved by incubating (37° C.—2 h) 0.4 units of Remove-iT® Endo S (New England Biolabs, Ipswich, USA) per microgram of AC prior to buffer exchange desalting step.

MS experiments were performed on an electrospray time-of-flight mass spectrometer MS (LCT, Waters, Manchester) coupled to an automated chip-based nanoelectrospray device (Triversa Nanomate, Advion Biosciences, Ithaca, U.S.A.) operating in the positive ion mode. For native MS experiments, external calibration of the ESI-TOF instrument was performed using singly charged ions produced by a 2 mg/mL solution of cesium iodide in 2-propanol/water (1v/1v). Tuning parameters of the mass spectrometer were carefully optimized to improve desolvation and ion transfer as well as maintaining weak interactions. Particularly, the sample cone voltage Vc was set to 120 V and the backing pressure Pi was increased to 6 mbar to improve ion collisional cooling and maintain non-covalent interaction for averaging DAR calculation. Native MS data interpretation was performed using MassLynx 4.1 (Waters, Manchester, UK.).

Average degree of conjugation (DoC) values from native MS were calculated from the relative peak intensities measured from the raw mass spectrum (taking into account $21^+$ to $26^+$ charge states). Average DoC value was obtained by summing up the weighted peak percentage from all observed species and dividing the sum by 100, as follows: DoC=Σ (relative peak intensity×number of loaded molecule)/100.

Stability of Antibody-iSyd-Biotin Conjugates on Streptavidin Column

To test the stability of the antibody-iSyd-Biotin conjugates, a HiTrap Streptavidin HP column loaded with antibody-iSyd-Biotin conjugates (1.5 mg) was subjected to the trans-tagging reaction (Part III) with BCN-TAMRA after 1 day, 2 weeks and 1 month (FIG. 1A). Between the trans-tagging reactions the column was kept in dark at 4° C. The resulting T-TAMRA conjugates were analyzed by SDS PAGE. Gel stained with Coomassie Blue showed no sign of degradation of the immobilized antibody-iSyd-Biotin conjugates over the period of one month (FIG. 1B).

The following compounds (D'-1) and (D-1) were prepared:

Compound 1

Compound 1 was prepared following General procedure A with Trastuzumab as a Protein and BCN-OH as a Trans-tagging reagent. MS spectrum of compound 1 was obtained following General procedure C.

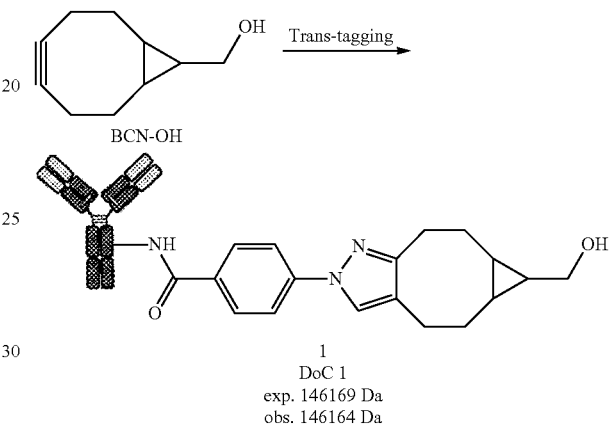

1
DoC 1
exp. 146169 Da
obs. 146164 Da

Compound 2

Compound 2 was prepared following General procedure A with Trastuzumab as a Protein and BCN-Cy5 as a Trans-tagging reagent. MS spectrum of compound 2 was obtained following General procedure C.

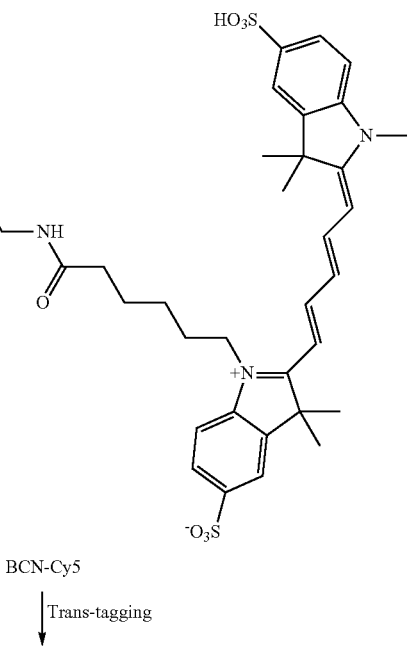

BCN-Cy5

Trans-tagging

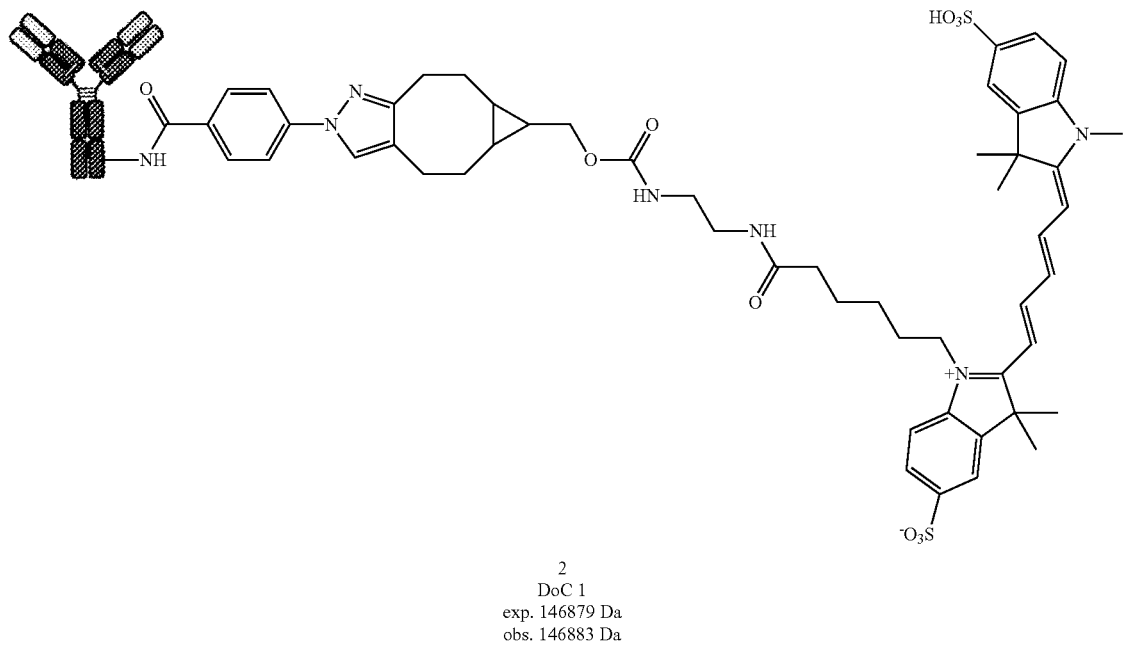
2
DoC 1
exp. 146879 Da
obs. 146883 Da
Compound 3 Compound 3 was prepared following General procedure A with Trastuzumab as a Protein and BCN-TAMRA as a Trans-tagging reagent. MS spectrum of compound 3 was obtained following General procedure C.
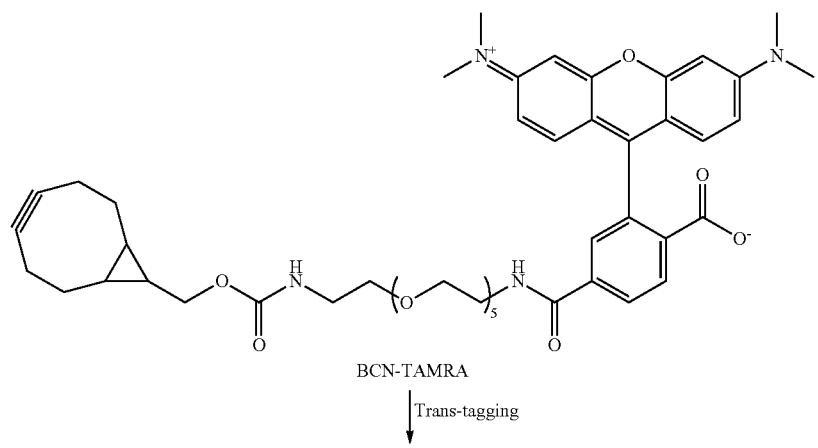
BCN-TAMRA
↓ Trans-tagging

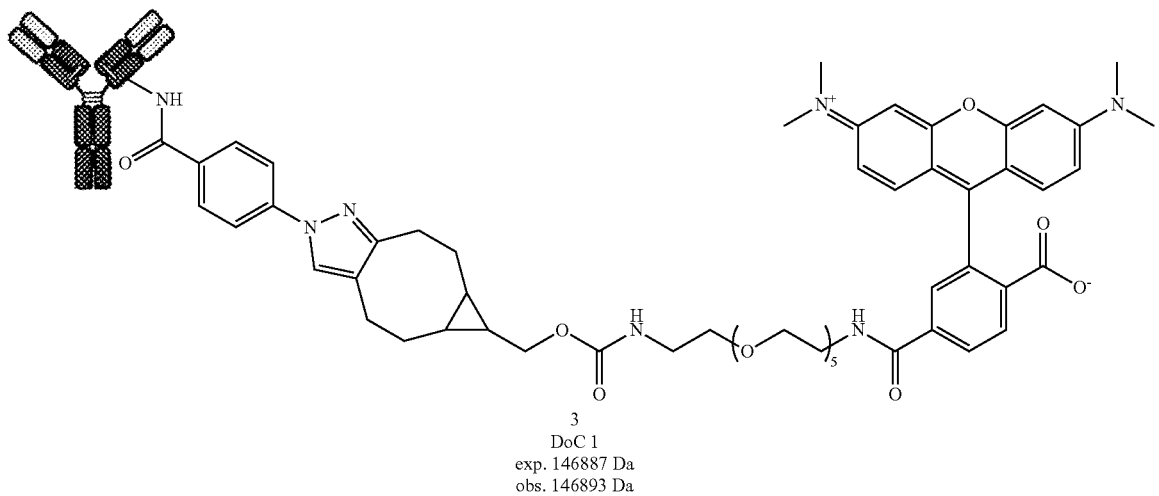
3
DoC 1
exp. 146887 Da
obs. 146893 Da
Compound 4 Compound 4 was prepared following General procedure A with Trastuzumab as a Protein and BCN-Oligo as a Trans-tagging reagent. MS spectrum of compound 4 was obtained following General procedure C.
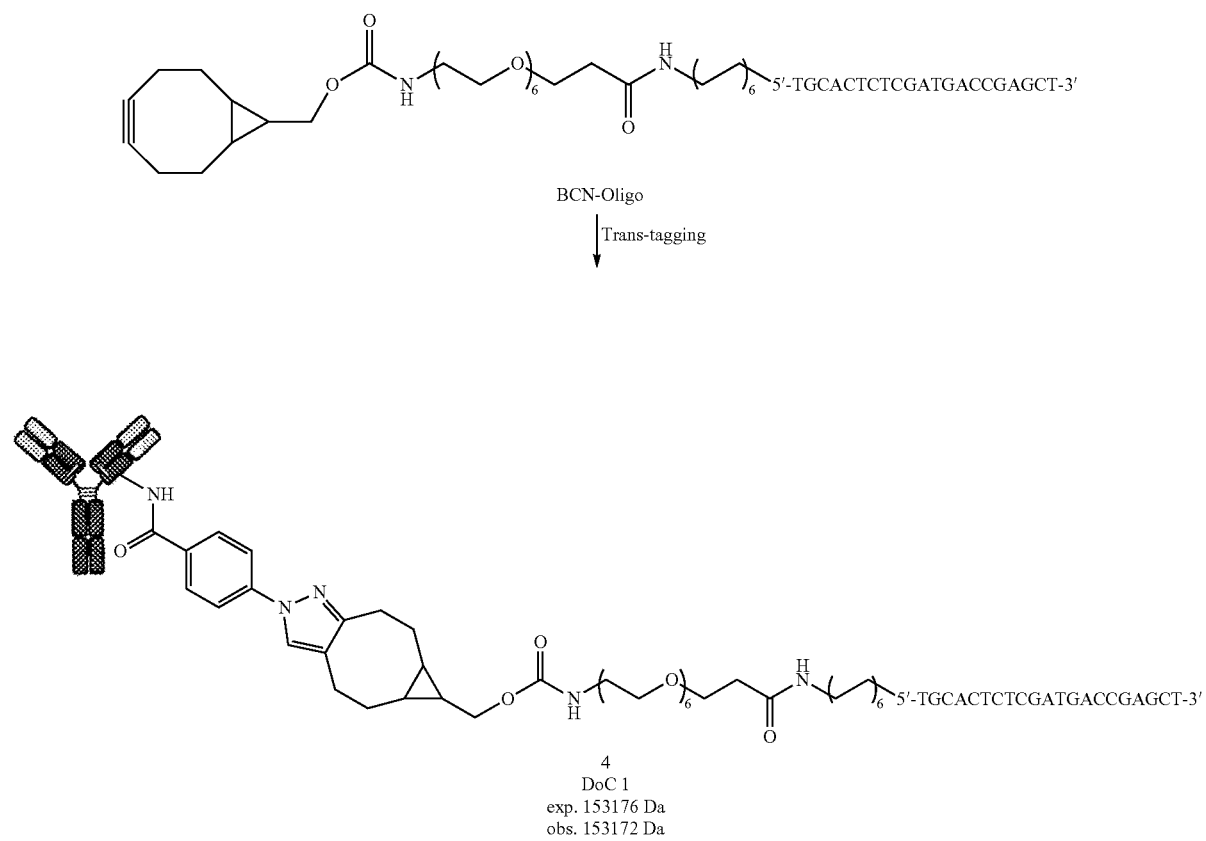
4
DoC 1
exp. 153176 Da
obs. 153172 Da Compound 5 Compound 5 was prepared following General procedure A with Trastuzumab as a Protein and BCN-BCN as a Trans-tagging reagent. MS spectrum of compound 5 was obtained following General procedure C.

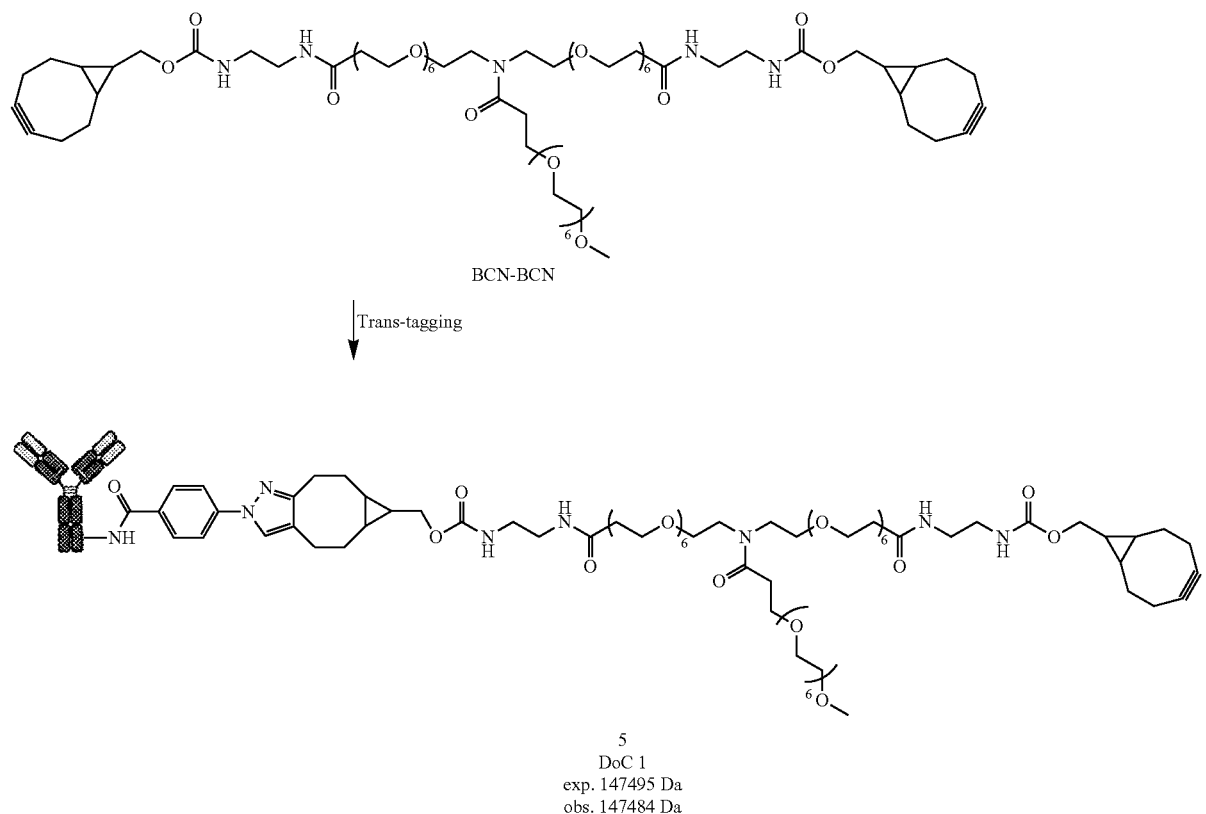

BCN-BCN

Trans-tagging

5
DoC 1
exp. 147495 Da
obs. 147484 Da

Compound 6 Compound 6 was prepared following General procedure B with compound 4 as a Protein derivative and Oligo2 as a post-modification reagent. MS spectrum of compound 6 was obtained following General procedure C.

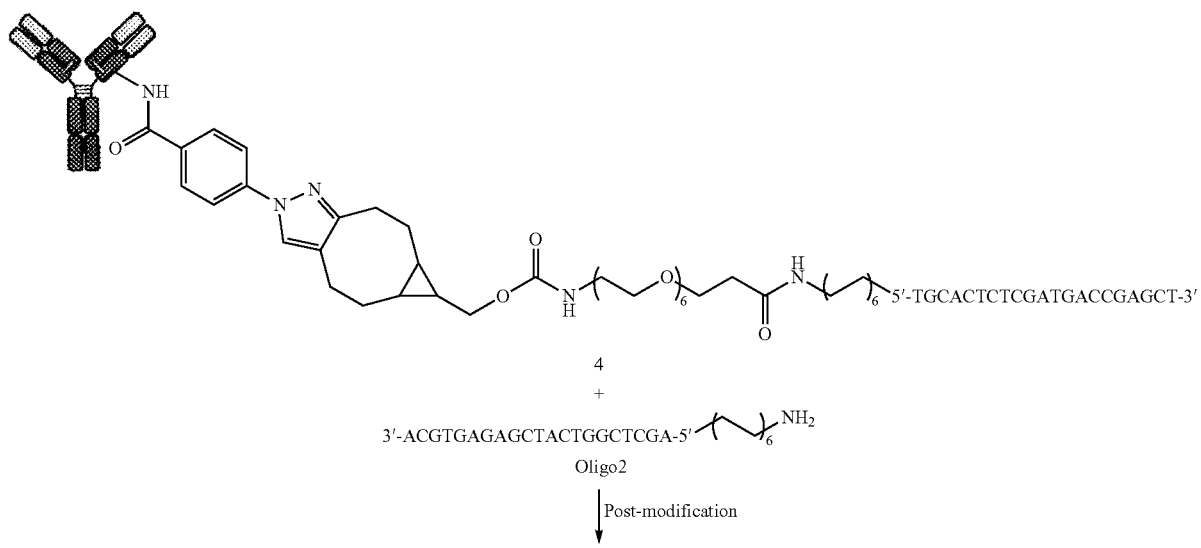

4
+
3'-ACGTGAGAGCTACTGGCTCGA-5'

Oligo2

Post-modification

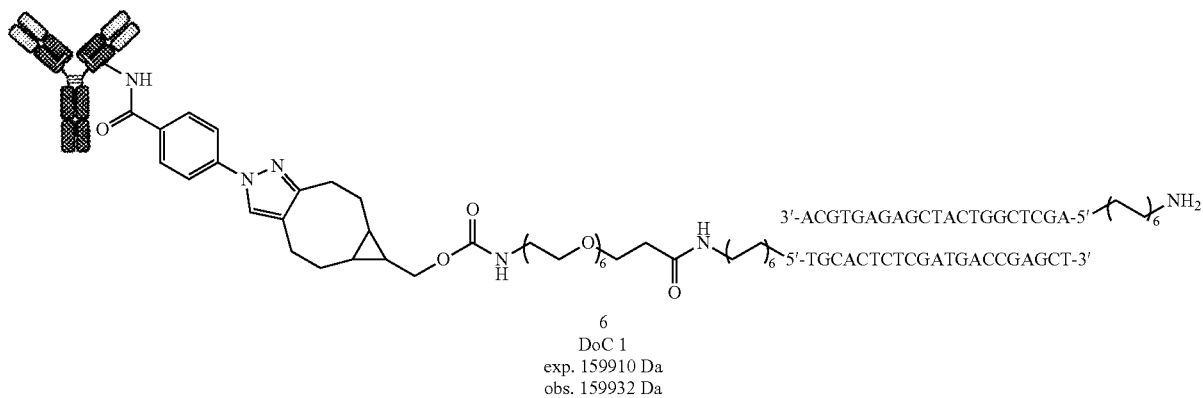
6
DoC 1
exp. 159910 Da
obs. 159932 Da
Compound 7 Compound 7 was prepared following General procedure B with compound 5 as a Protein derivative and TAMRA-N₃ as a post-modification reagent.
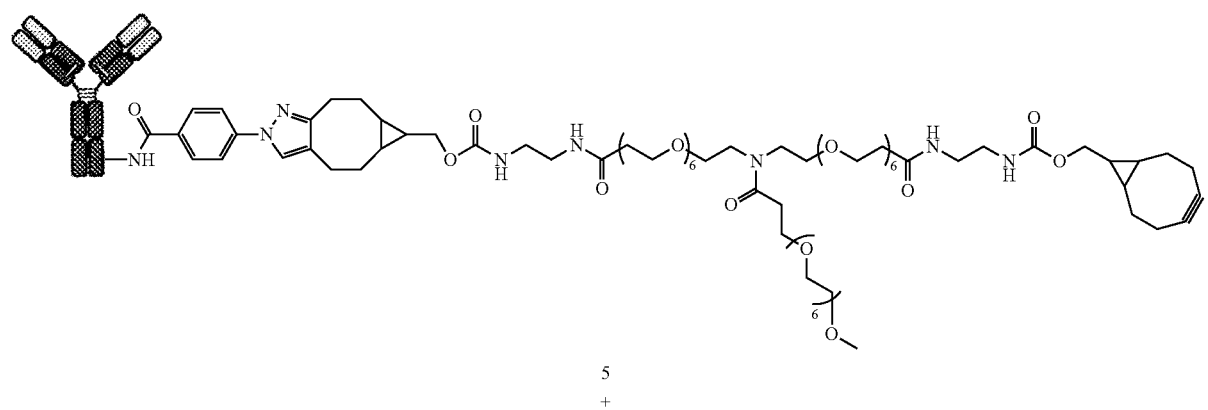
5
+
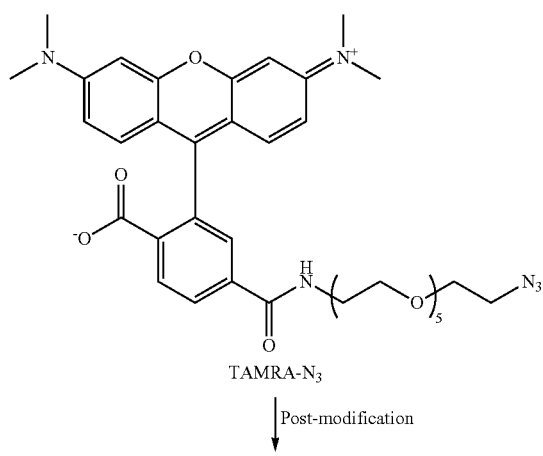
TAMRA-N₃
↓ Post-modification

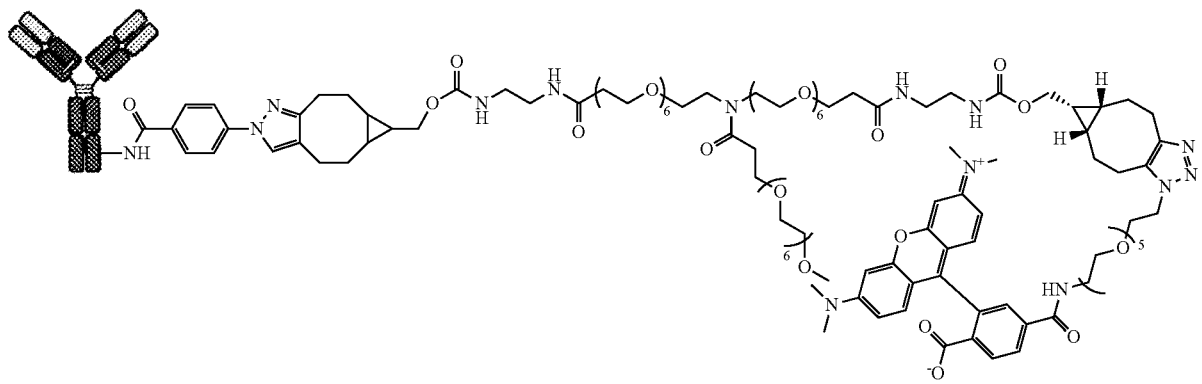

7

Compound 8 Compound 8 was prepared following General procedure A with Trastuzumab as a Protein and DBCO-COOH as a Trans-tagging reagent. MS spectrum of compound 8 was obtained following General procedure C.

Example 3: Preparation of a Compound of Formula (I): Preparation of Biotin-iSyd2-NHS Compound 9

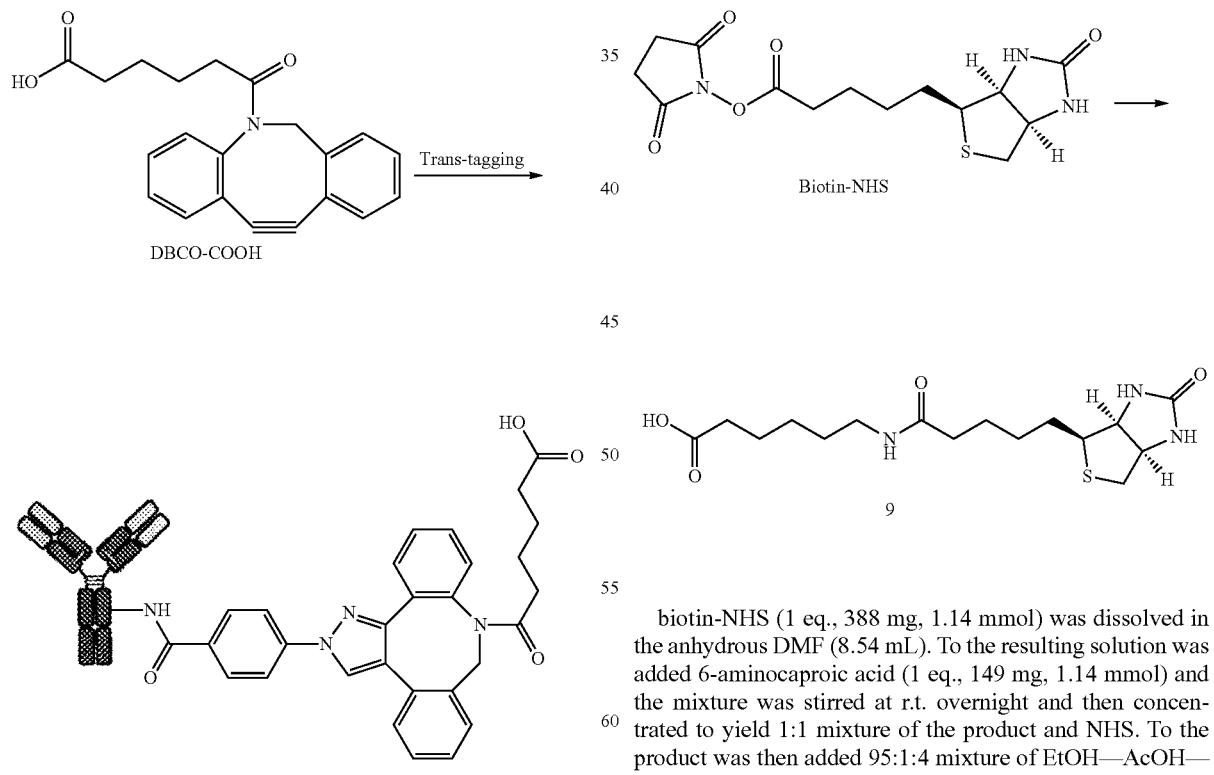

8
DoC 1
exp. 146345 Da
obs. 146343 Da

9 biotin-NHS (1 eq., 388 mg, 1.14 mmol) was dissolved in the anhydrous DMF (8.54 mL). To the resulting solution was added 6-aminocaproic acid (1 eq., 149 mg, 1.14 mmol) and the mixture was stirred at r.t. overnight and then concentrated to yield 1:1 mixture of the product and NHS. To the product was then added 95:1:4 mixture of EtOH—AcOH—H$_2$O. The resulting suspension was heated to boiling, filtered, and left to crystallize to yield compound 9 (305 mg, 0.854 mmol, 75%) as a white fluffy solid. The structure of 9 was confirmed by ESI-MS analysis (Method 1).

ESI-MS m/z: 358.3 [M+H]$^+$

Compound 10

9 ⟶

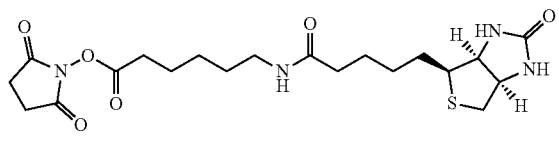

To a suspension of compound 9 (1 eq., 520 mg, 1.45 mmol) in DMF (25.5 mL) were subsequently added N,N'-disuccinimidyl carbonate (2.5 eq., 931 mg, 3.64 mmol) and TEA (2 eq., 294 mg, 0.404 mL, 2.91 mmol). After 15 minutes the precipitate solubilized, stirring continued for 2 h at room temperature. 10× volume of Et$_2$O was then added and the obtained precipitate was filtered to yield the crude product, which was recrystallized from a minimum amount of ACN to yield compound 10 as a white solid. The structure of 10 was confirmed by ESI-MS analysis (Method 1).

ESI-MS m/z: 455.5 [M+H]$^+$

Compound 11

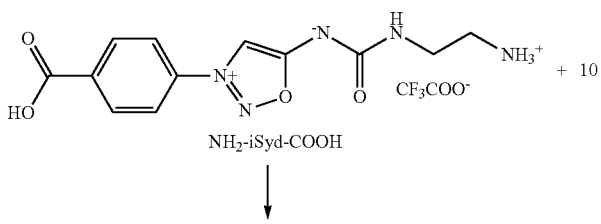

NH$_2$-iSyd-COOH

↓

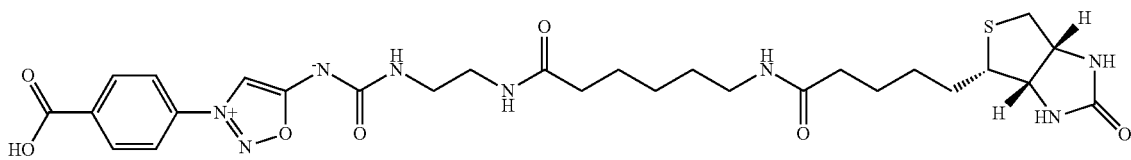

11

To the solution of NH$_2$-iSyd-COOH (1 eq., 333 mg, 0.822 mmol) in DMF (5 mL) was added TEA (4 eq., 0.457 mL, 3.287 mmol) followed by a solution of 10 (1 eq., 374 mg, 0.822 mmol) in DMF (10 mL). Stirring continued overnight until complete disappearance of the starting material. Et$_2$O (150 mL) was then added to precipitate TEA salt of the product. The precipitate was filtered suspended in EtOH (15 mL), then TFA was added (5 mL). Stirring continued until complete dissolution of the precipitate. The solution was concentrated on rotatory evaporator, dried under vacuum to eliminate the excess of TFA, resolubilized with slight heating in minimum amount of DMF (3 mL), precipitated with warm (30° C.) acetonitrile and filtered to yield compound 11 (440 mg, 0.698 mmol, 85%) as a yellow solid. The structure of 11 was confirmed by ESI-MS analysis (Method 1).

ESI-MS m/z: 631.3 [M+H]$^+$

Biotin-iSyd2-NHS

11 ⟶

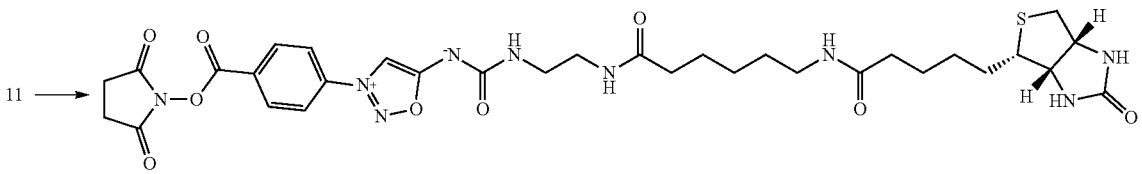

Biotin-iSyd2-NHS

A solution of 11 (1 eq., 78 mg, 0.124 mmol), NHS (5 eq., 71.2 mg, 0.618 mmol) and DCC (2 eq., 51 mg, 0.247 mmol) in DMSO (3 mL) was stirred overnight at room temperature. The resulting mixture was purified by preparative HPLC (40 min run, detection at 254 nm; buffer A: H₂O miliQ+0.05% of TFA; buffer B: ACN; 40 min—from 5% to 95% B). The collected fraction was promptly lyophilized to yield Biotin-iSyd2-NHS (82.8 mg, 0.114 mmol, 92%) as a yellow solid. The structure of Biotin-iSyd2-NHS was confirmed by ESI-MS analysis (Method 1).

ESI-MS m/z: 728.4 [M+H]⁺

Example 4: Bioconjugation Using Biotin-iSyd2-NHS 4.1 General Procedure D for the Preparation of Protein Conjugates (D-n) with Defined Degree of Conjugation This comprises three parts:
Part I. Preparation of protein conjugates (E-1) with affinity tag in low conversion
Part II. Loading of protein conjugates (E-1) into the affinity column
Part III. Trans-tagging reaction 4.1.1 Part I. Preparation of Protein-iSyd2-Biotin Conjugates (E-1):

A solution of Biotin-iSyd2-NHS reagent (0.16 eq., 54 µL, 500 µM in DMSO) were added to a solution of protein (1 eq., 5 mg/mL, 5 mL in potassium phosphate buffer, pH 8.5) at 25° C. The reaction mixture was maintained at 25° C. for 15 min and used in the next step without purification.

4.1.2 Part II. Loading of Protein Conjugates (E-1) into the Affinity Column

Protein-iSyd2-Biotin conjugate (5 mL in potassium phosphate buffer, pH 8.5) was injected into HiTrap Streptavidin HP column (1 mL, GE Healthcare Life Sciences, Ref. 17-5112-01) equilibrated with potassium phosphate buffer (pH 8.5) using syringe pump at flow rate of 0.5 mL/min. The eluate containing unconjugated protein was collected and used in subsequent subsequent conjugation/loading cycles.

Parts I and II were repeated 20 times while keeping the amount of added Biotin-iSyd2-NHS at 0.16 eq. comparing to the amount of protein engaged in each cycle.

4.1.3 Part III. Trans-Tagging Reaction

Streptavidin column containing immobilized protein, obtained after repeating Part I and II 20 times, was washed with 10 mL of PBS 1× (pH 7.4) and then with 10 mL of PBS/DMSO (9/1, pH 7.4) at 1 mL/min flow rate.

Trans-tagging reaction was performed in the streptavidin column using as compound of formula (II) derivatives of bicyclononyne (BCN), derivatives of dibenzocyclooctyne (DBCO) or 3,3,6,6-tetramethylthiacycloheptyne (TMTH). A solution of compound of formula (II) (20 µM, 1 mL in PBS 1×, pH 7.4 containing 10% of DMSO) was injected into the column. The column was incubated at 25° C. for 16 h, then connected to the inlet of Superdex 200 Increase column (GE Healthcare Life Sciences), equilibrated with PBS 1× (pH 7.4), and eluted with PBS 1× (pH 7.4, 48 mL) at flow rate of 0.15 mL/min using ÄKTA Pure chromatography system (GE Healthcare Life Sciences). The collected fraction of the functionalized protein conjugate was concentrated using Vivaspin 500 centrifugal filtration unit (MWCO 10 kD, Sartorius). The resulting conjugates of formula (D'-1) were subjected to MS analysis according to General Procedure C.

Compound 12

Compound 12 was prepared following General procedure D with Trastuzumab as a Protein and TMTH as a Trans-tagging reagent. MS spectrum of compound 12 was obtained following General procedure C.

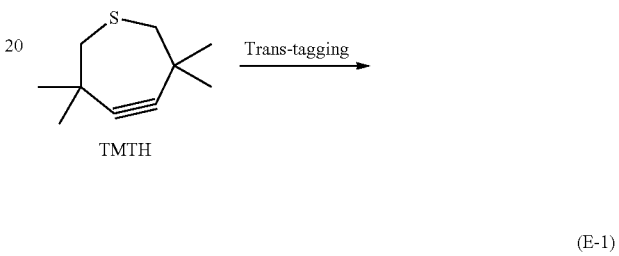

TMTH → Trans-tagging

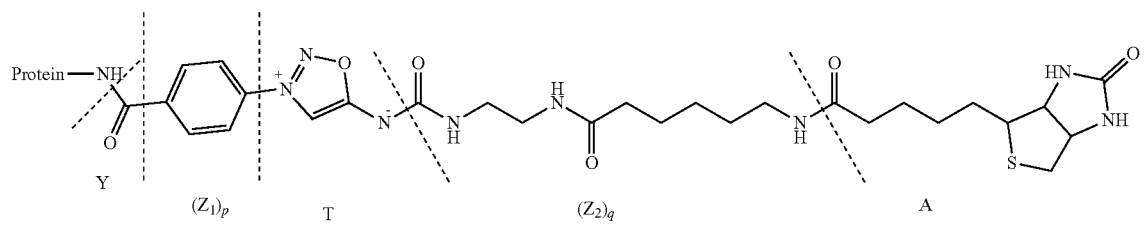

(E-1)

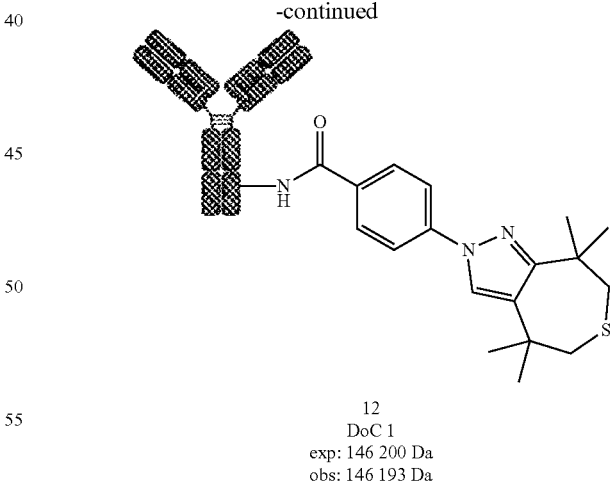

12
DoC 1
exp: 146 200 Da
obs: 146 193 Da

Compound 13

Compound 13 was prepared following General procedure D with Trastuzumab as a Protein and DBCO-MMAF as a Trans-tagging reagent. MS spectrum of compound 13 was obtained following General procedure C.

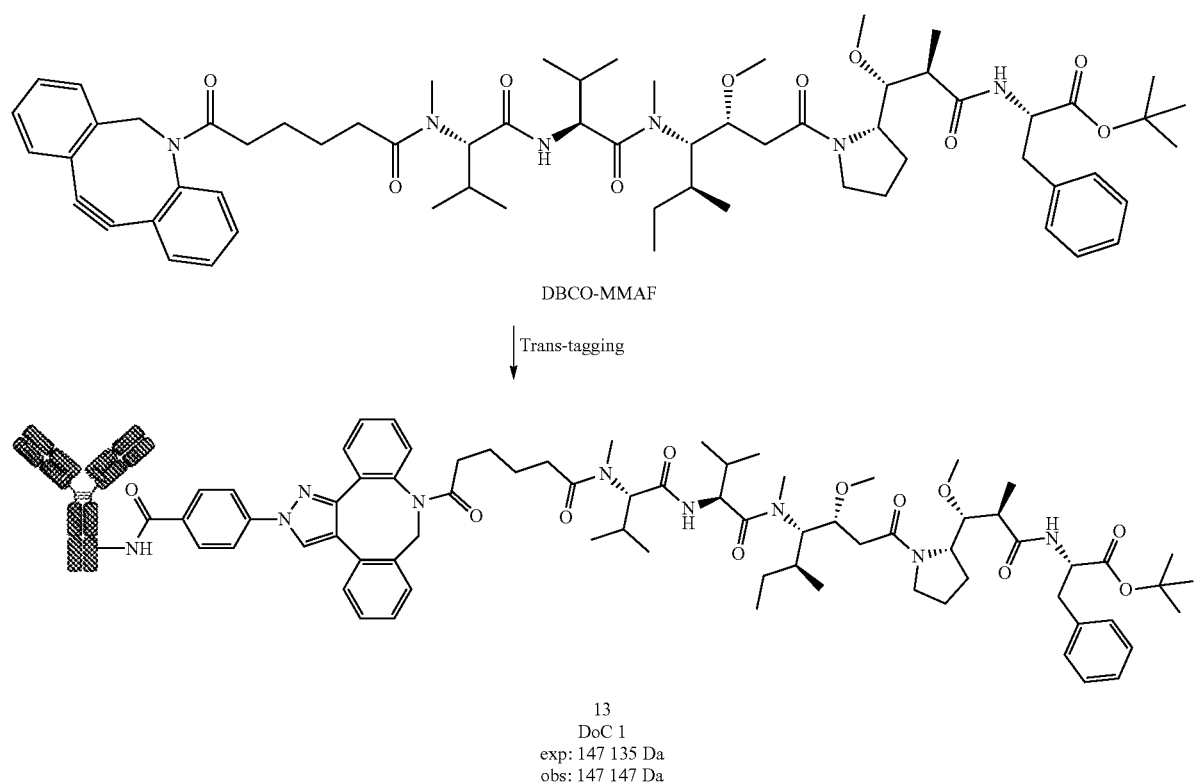

13
DoC 1
exp: 147 135 Da
obs: 147 147 Da

Compound 14

Compound 14 was prepared following General procedure D with Bevacizumab as a Protein and BCN-Cy5 as a Trans-tagging reagent. MS spectrum of compound 14 was obtained following General procedure C.

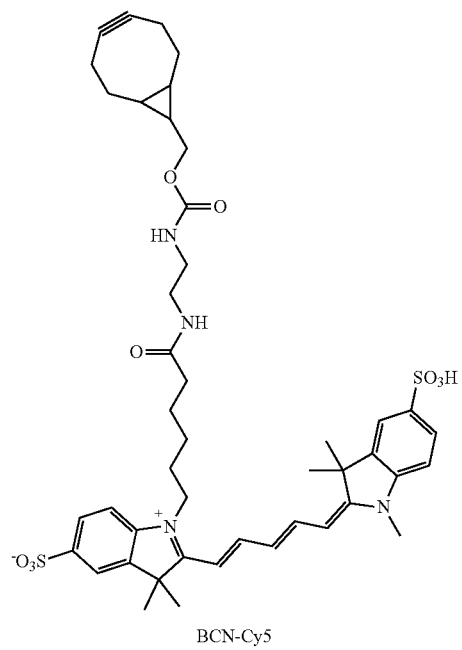

BCN-Cy5

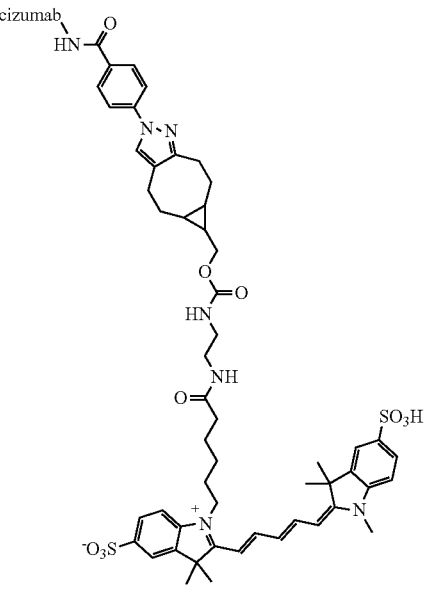

14
DoC 1 exp: 150 204 Da obs: 150 208 Da

Compound 15

Compound 15 was prepared following General procedure D with recombinant human serum albumin (HSA) as a Protein and BCN-Cy5 as a Trans-tagging reagent. MS spectrum of compound 15 was obtained following General procedure C.

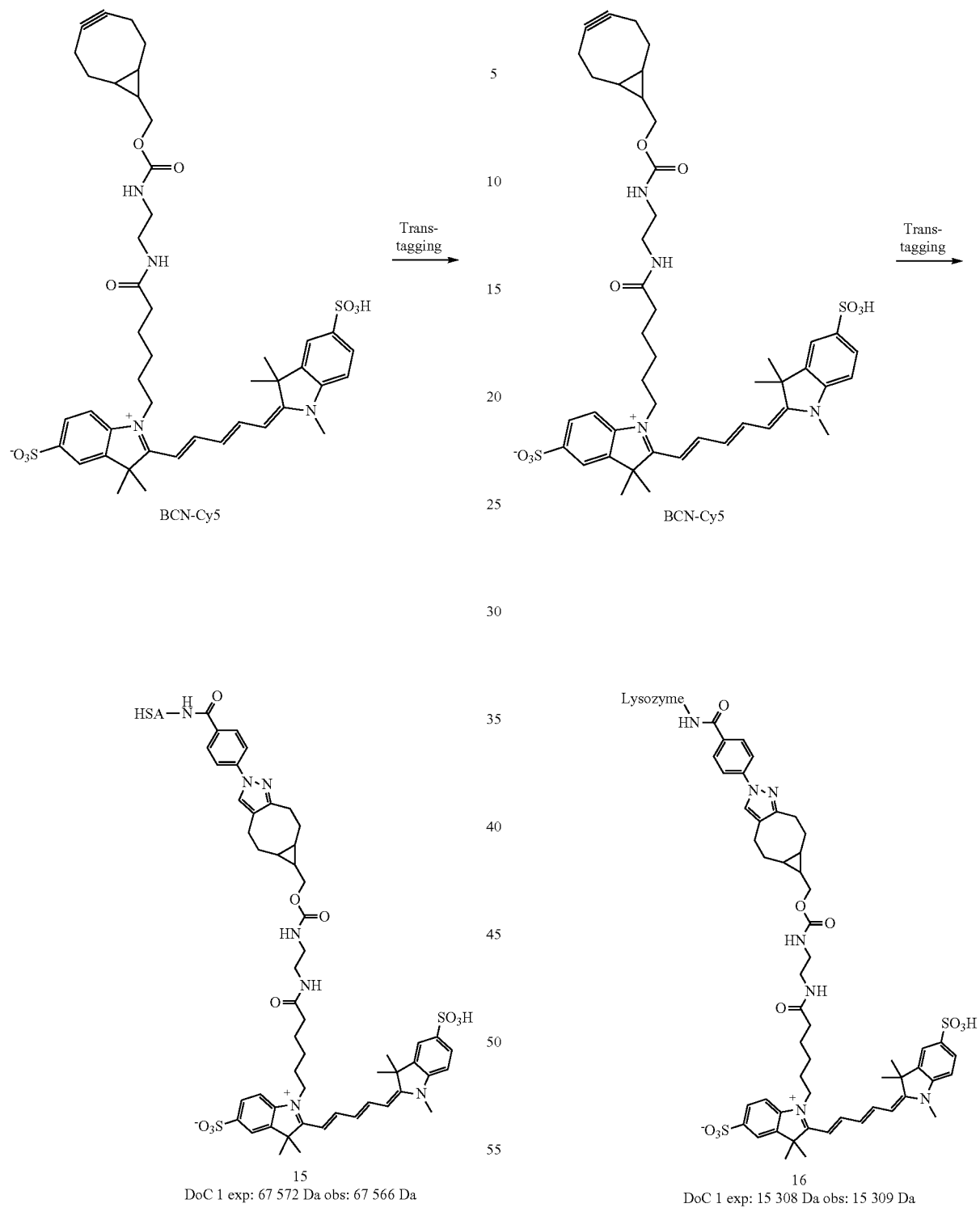

Compound 16

Compound 16 was prepared following General procedure D with Lysozyme as a Protein and BCN-Cy5 as a Trans-tagging reagent. MS spectrum of compound 16 was obtained following General procedure C.

Compound 17 Compound 17 was prepared following General procedure D with Trastuzumab as a Protein and diBCN as a Trans-tagging reagent. MS spectrum of compound 17 was obtained following General procedure C.

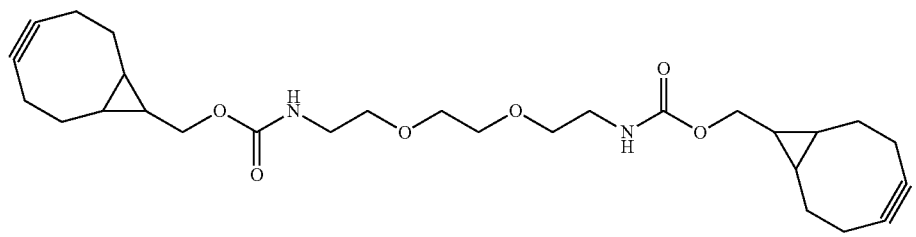
diBCN
↓ Trans-tagging
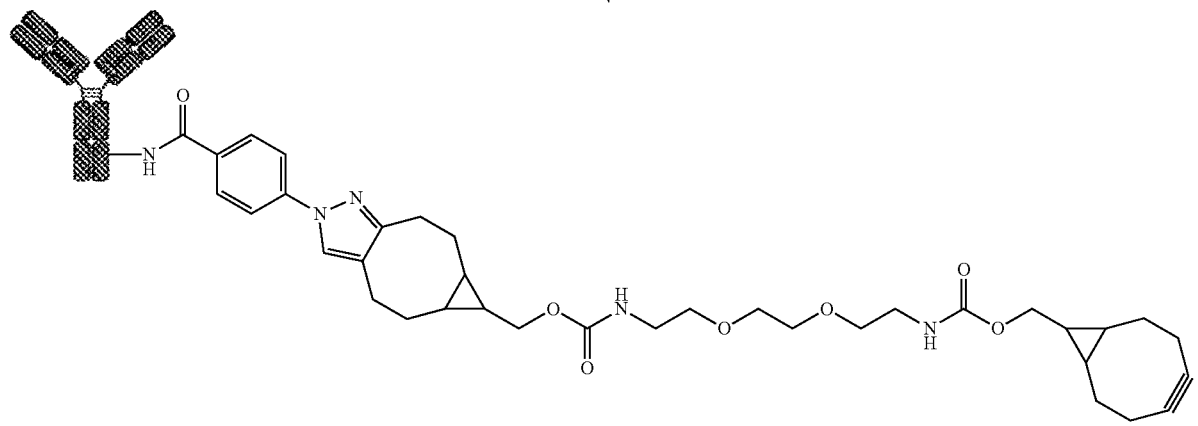
17
DoC 1
exp: 146 519 Da
obs: 146 522 Da
Compound 18
Compound 18 was prepared following General procedure D with Trastuzumab as a Protein and BCN-MMAE as a Trans-tagging reagent. MS spectrum of compound 18 was obtained following General procedure C.

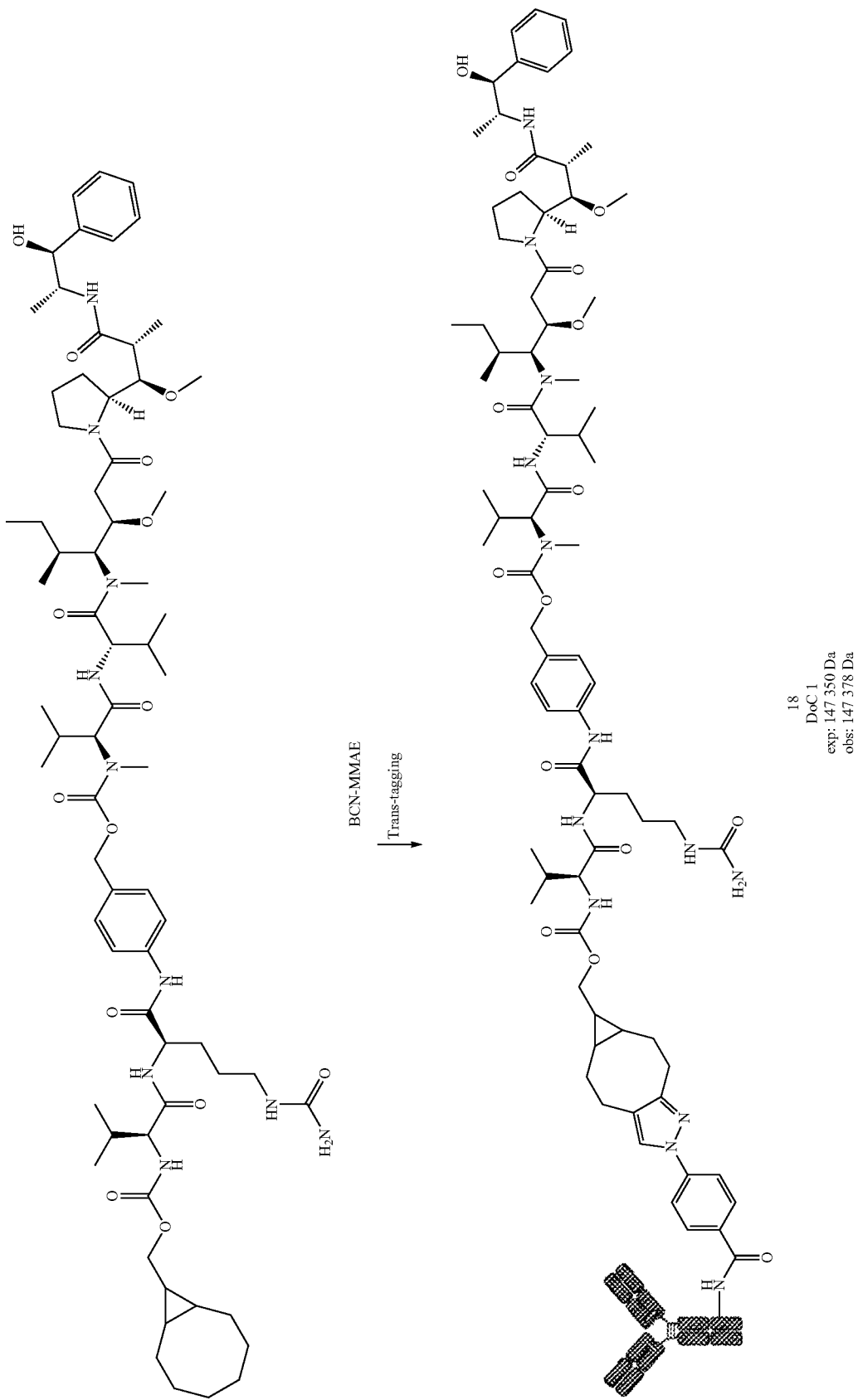

Compound 19 Compound 19 was prepared following General procedure D with compound 8 as a Protein and DBCO-COOH as a Trans-tagging reagent. MS spectrum of compound 19 was obtained following General procedure C.

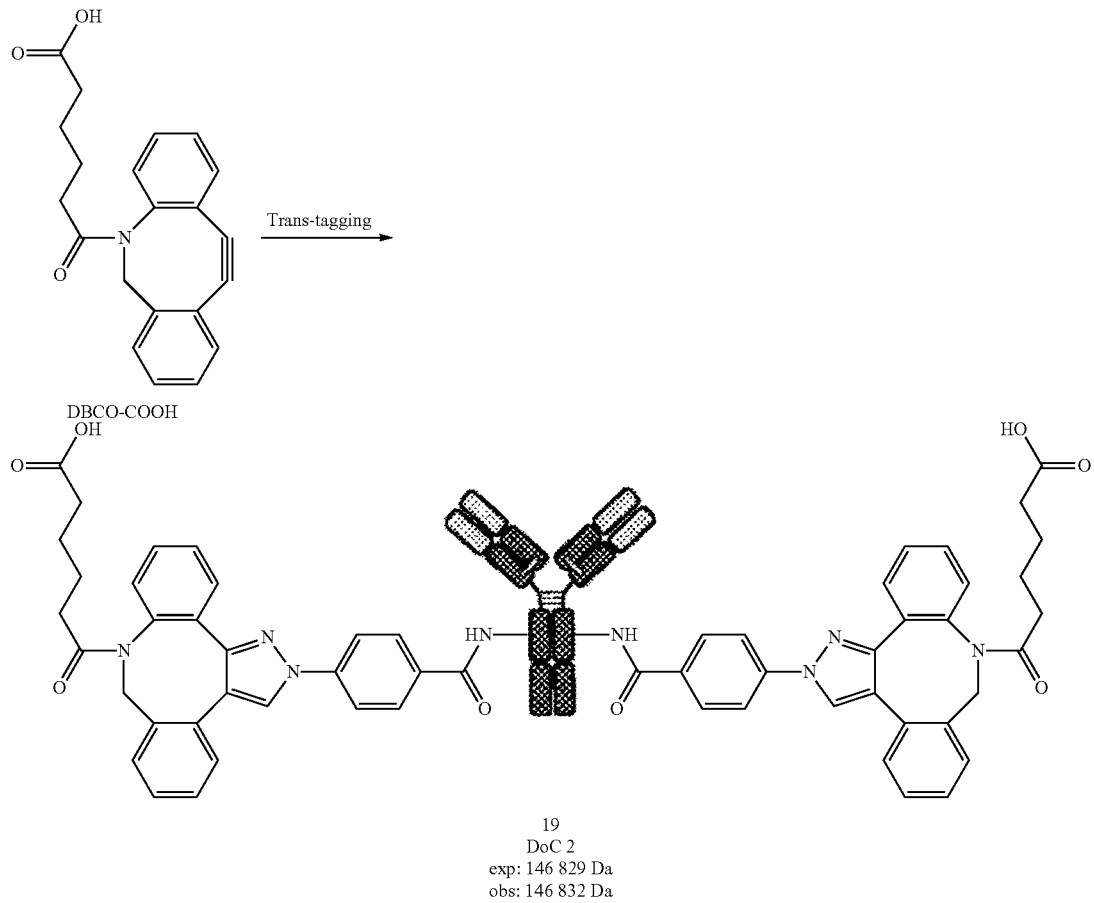

19
DoC 2
exp: 146 829 Da
obs: 146 832 Da

Compound 20

Compound 20 was prepared following General procedure D with compound 8 as a Protein and BCN-TAMRA as a Trans-tagging reagent. MS spectrum of compound 20 was obtained following General procedure C.

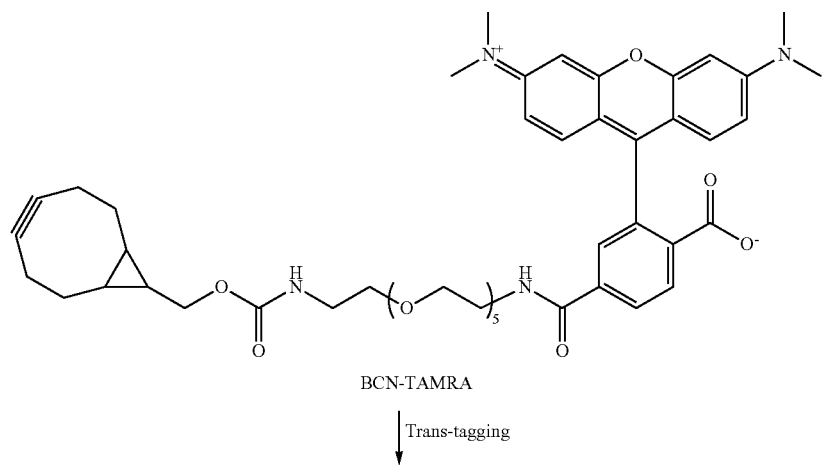

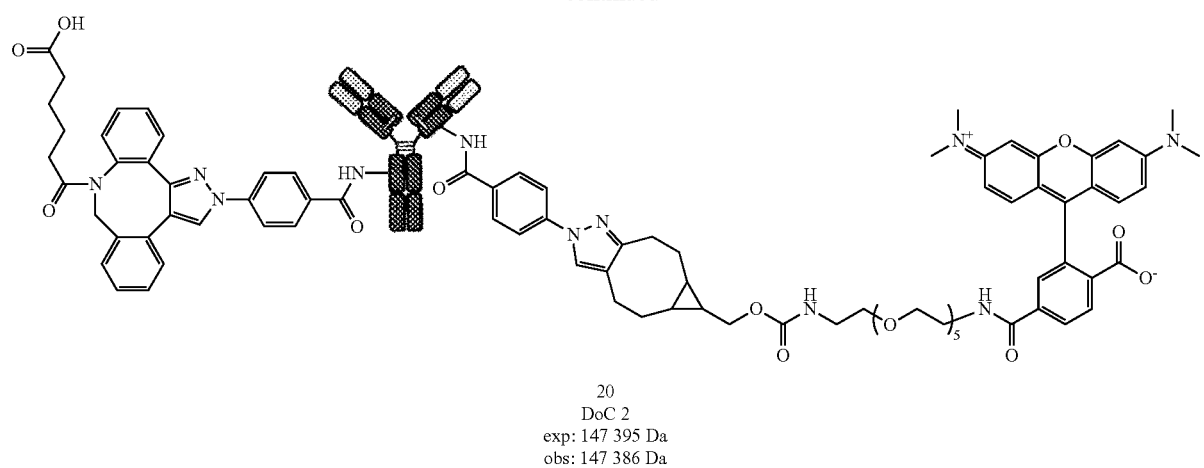
20
DoC 2
exp: 147 395 Da
obs: 147 386 Da
Compound 21
Compound 21 was prepared following General procedure D with compound 8 as a Protein and DBCO-PEG as a Trans-tagging reagent. MS spectrum of compound 21 was obtained obtained following General procedure C.
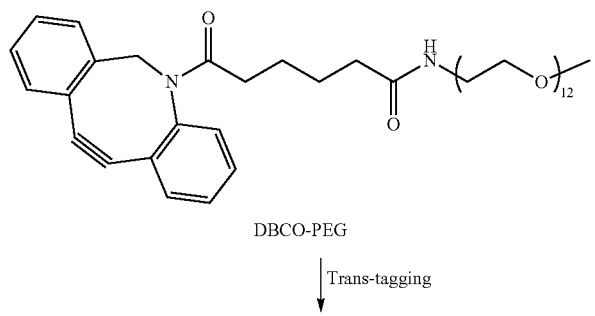
DBCO-PEG
↓ Trans-tagging
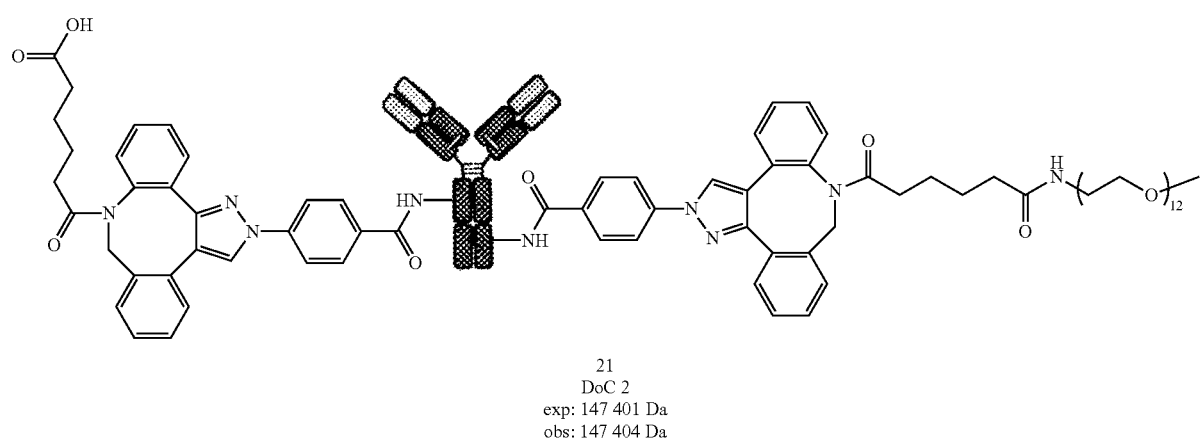
21
DoC 2
exp: 147 401 Da
obs: 147 404 Da Compound 22
Compound 22 was prepared following General procedure D with Trastuzumab as a Protein and DBCO-PEG as a Trans-tagging reagent. MS spectrum of compound 22 was obtained following General procedure C.
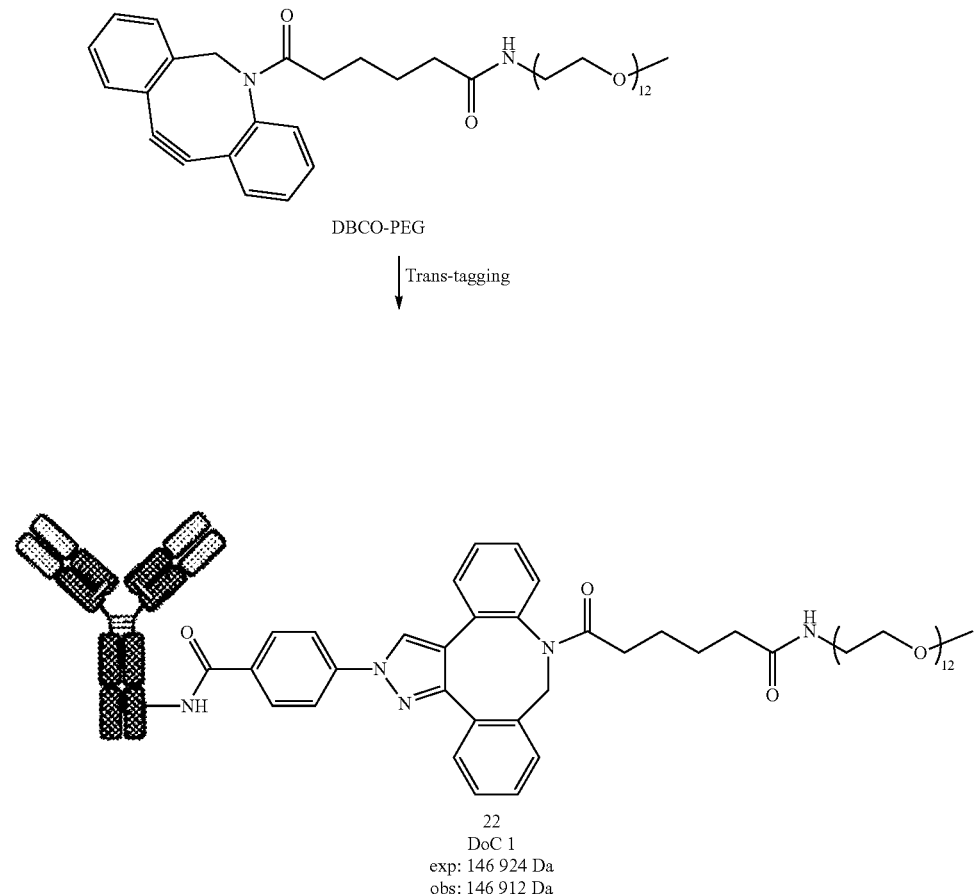
Compound 23
Compound 23 was prepared following General procedure B with compound 17 as a Protein derivative and TAMRA-Pr—N$_3$ as a post-modification reagent.
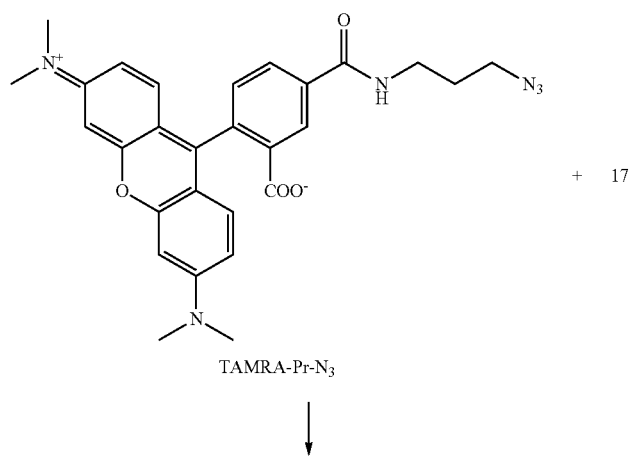

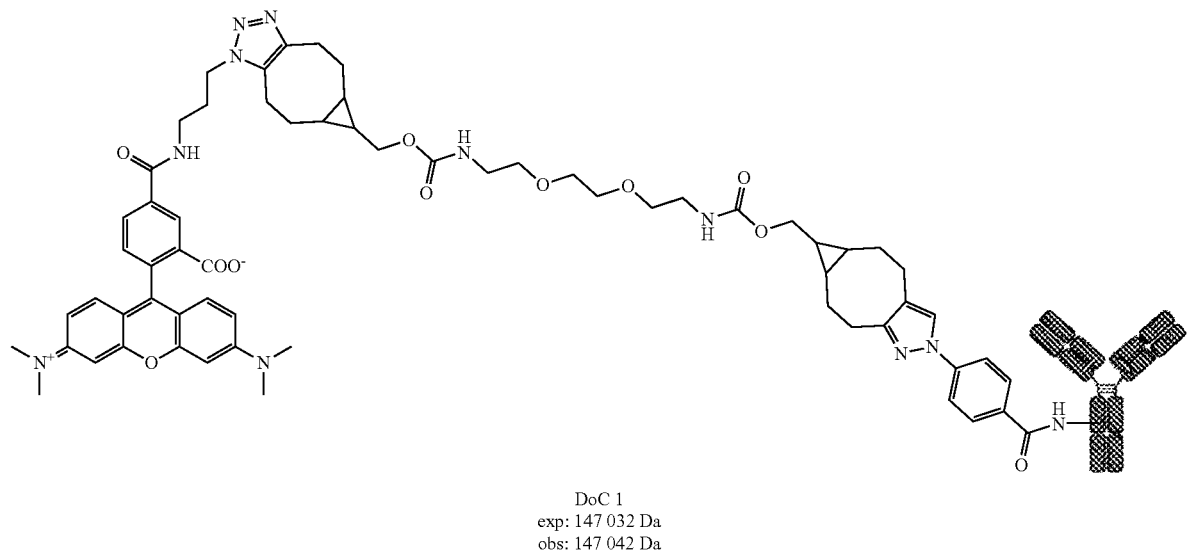
DoC 1
exp: 147 032 Da
obs: 147 042 Da
Compound 24
Compound 24 was prepared following General procedure D with Trastuzumab as a Protein and BCN-MMAF as a Trans-tagging reagent. MS spectrum of compound 24 was obtained following General procedure C.
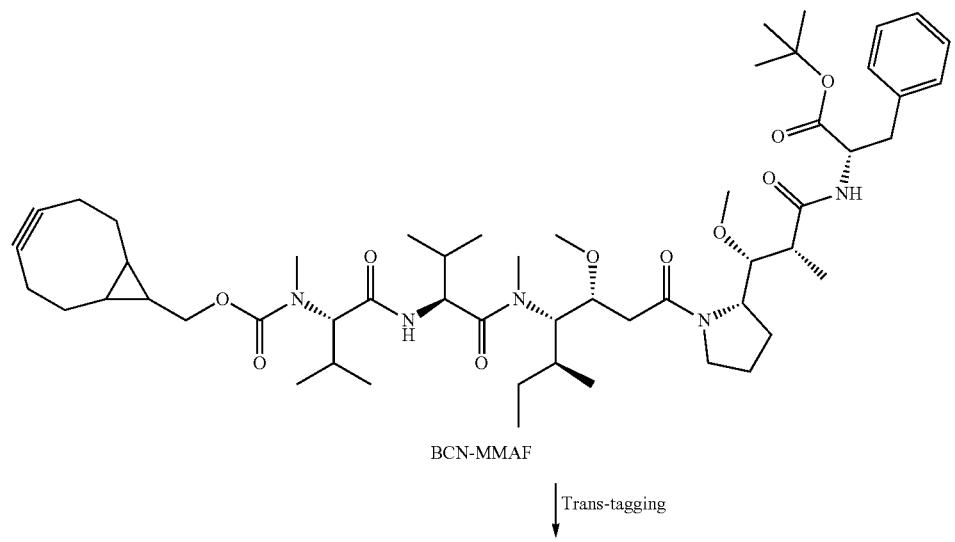
BCN-MMAF
↓ Trans-tagging

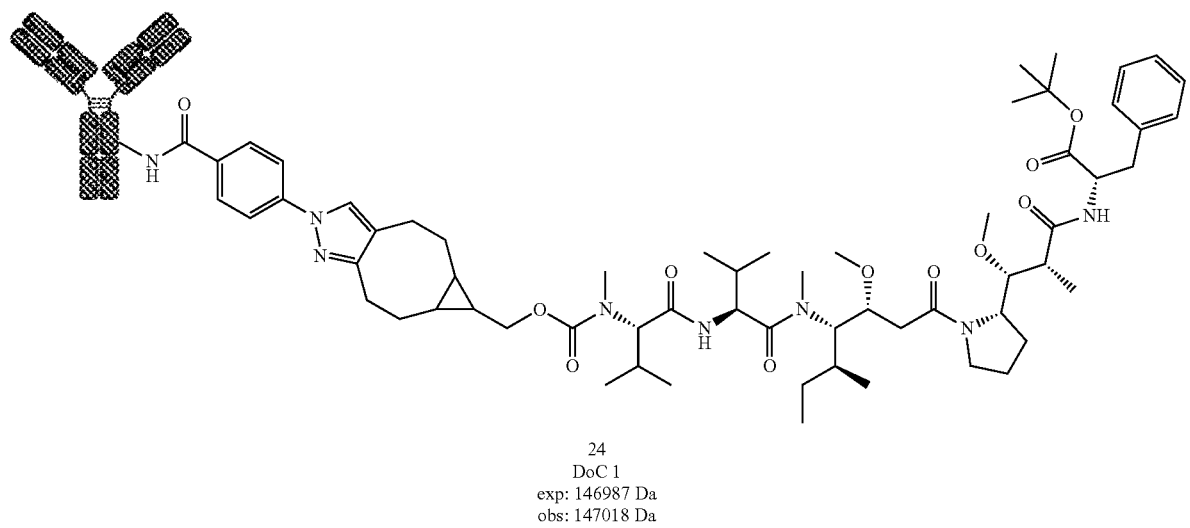
24
DoC 1
exp: 146987 Da
obs: 147018 Da
Compound 25 Compound 25 was prepared following General procedure D with Trastuzumab as a Protein and DBCO-MMAE as a Trans-tagging reagent. MS spectrum of compound 25 was obtained following General procedure C.
35
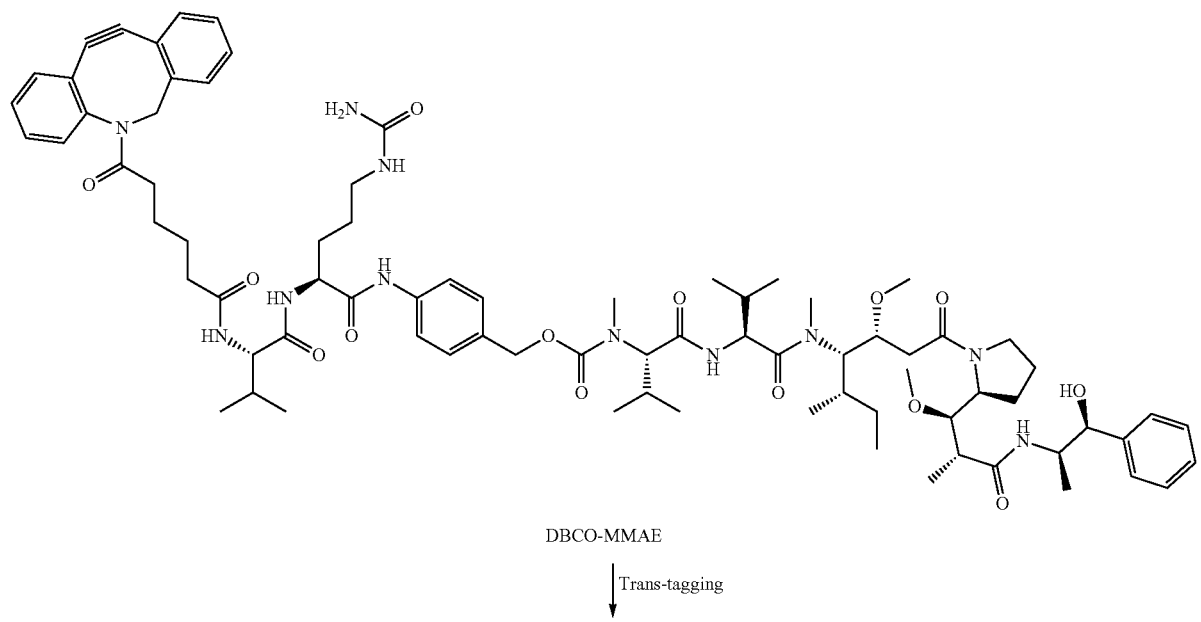
DBCO-MMAE
Trans-tagging

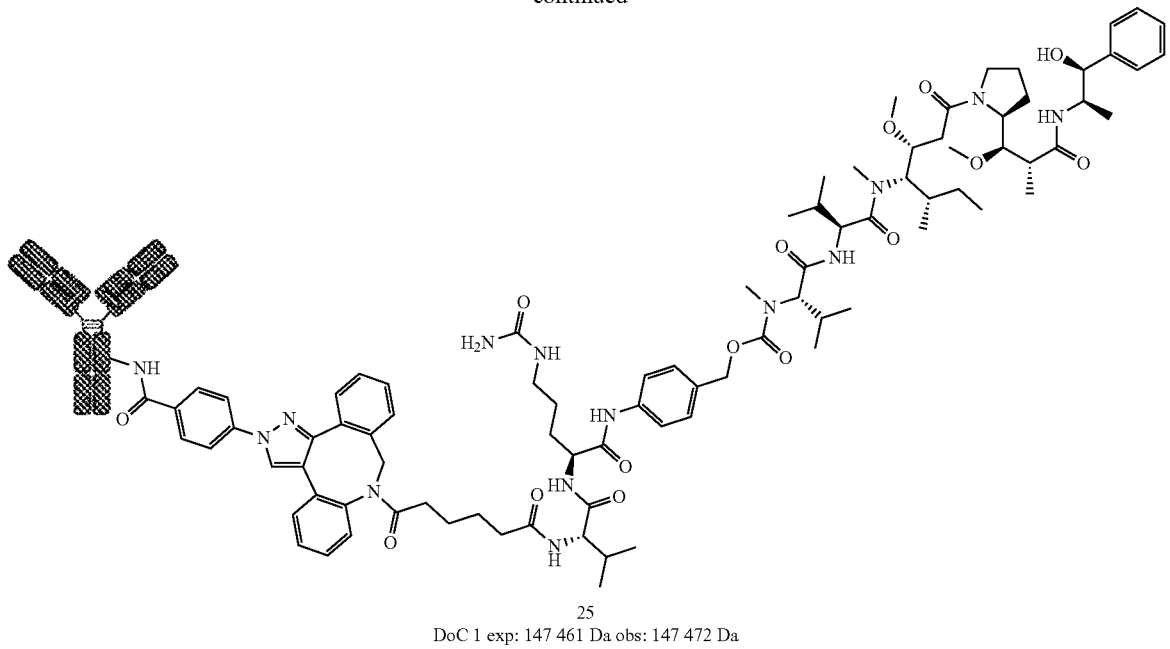
25
DoC 1 exp: 147 461 Da obs: 147 472 Da
Compound 26 Compound 26 was prepared following General procedure D with recombinant human serum albumin (HSA) as a Protein and BCN-TAMRA as a Trans-tagging reagent. MS spectrum of compound 26 was obtained following General procedure C.
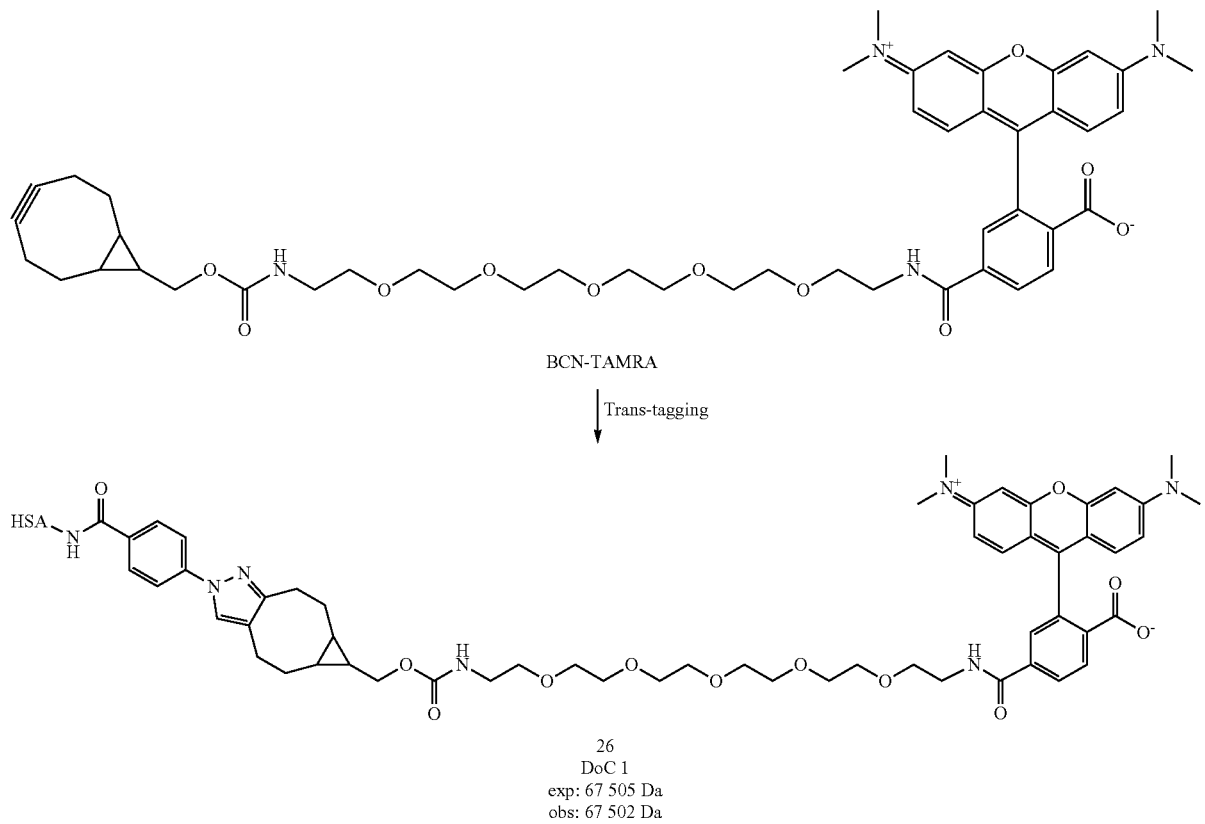
26
DoC 1
exp: 67 505 Da
obs: 67 502 Da Compound 27

Compound 27 was prepared following General procedure D with recombinant human serum albumin (HSA) as a Protein and DBCO-COOH as a Trans-tagging reagent. MS spectrum of compound 27 was obtained following General procedure C.

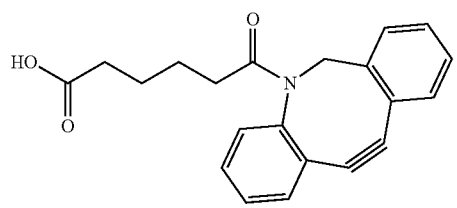

DBCO-COOH

| Trans-tagging

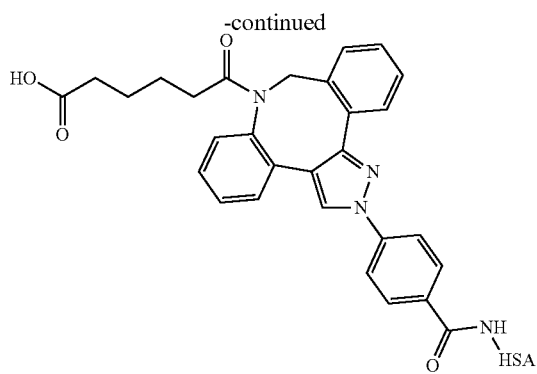

27
DoC 1
exp: 67 043 Da
obs: 67 040 Da

Compound 28

Compound 28 was prepared following General procedure D with recombinant human serum albumin (HSA) as a Protein and DBCO-MMAE as a Trans-tagging reagent. MS spectrum of compound 28 was obtained following General procedure C.

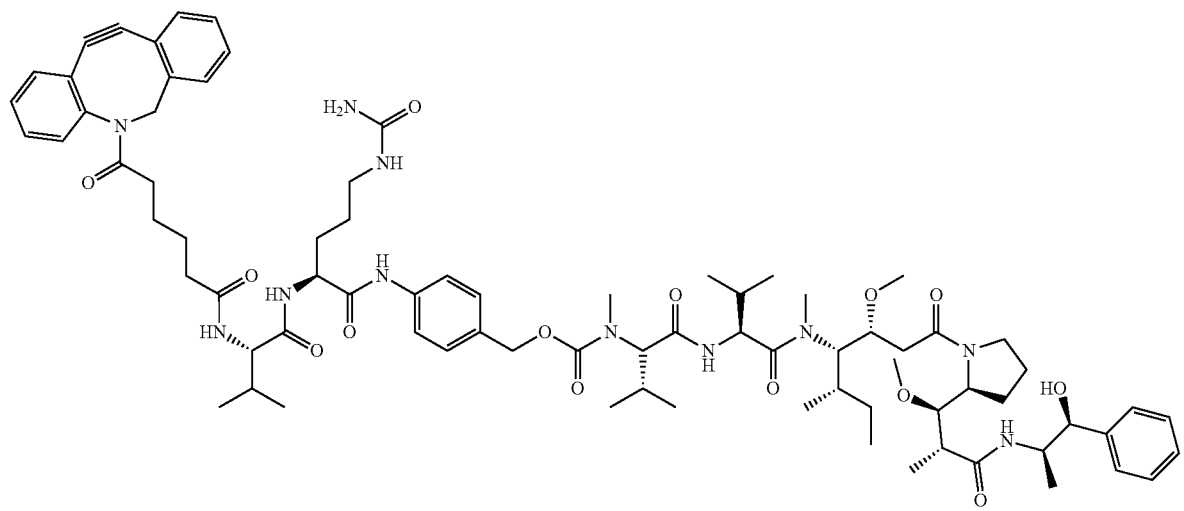

DBCO-MMAE

| Trans-tagging

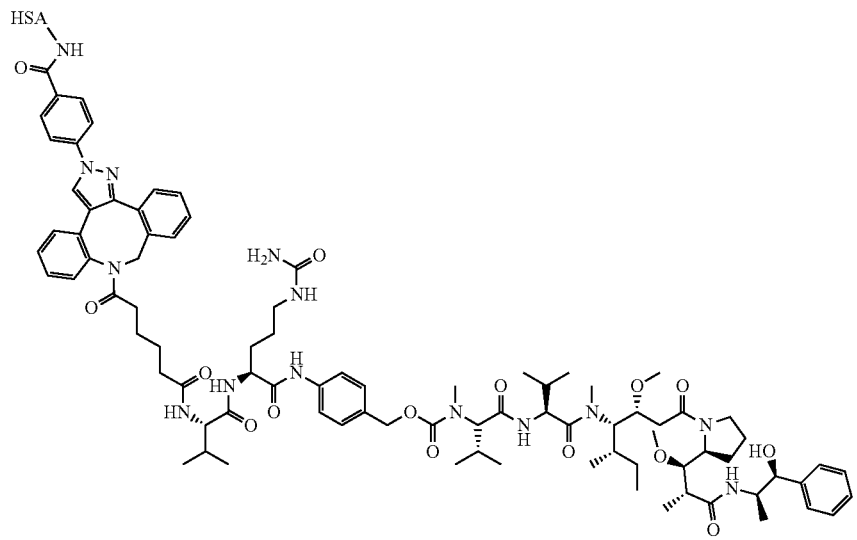
28
DoC 1
exp: 68 148 Da
obs: 68 165 Da
Compound 29
Compound 29 was prepared following General procedure D with Lysozyme as a Protein and BCN-MMAE as a Trans-tagging reagent. MS spectrum of compound 29 was obtained following General procedure C.
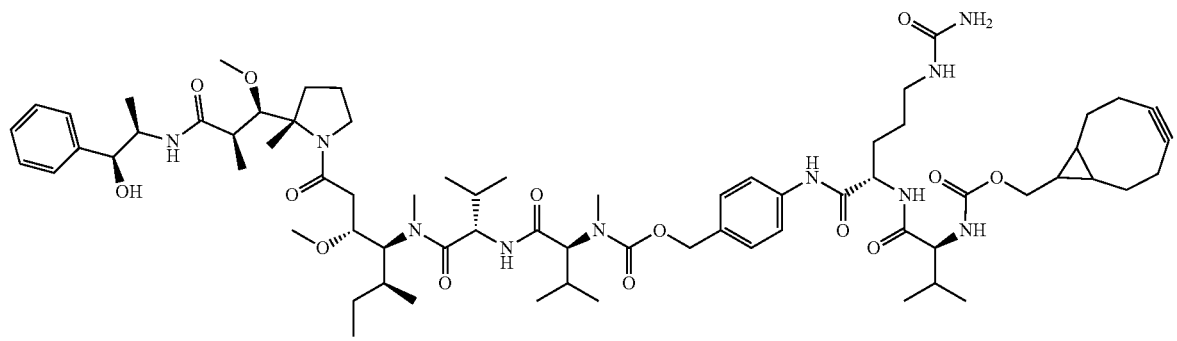
BCN-MMAE
↓ Trans-tagging

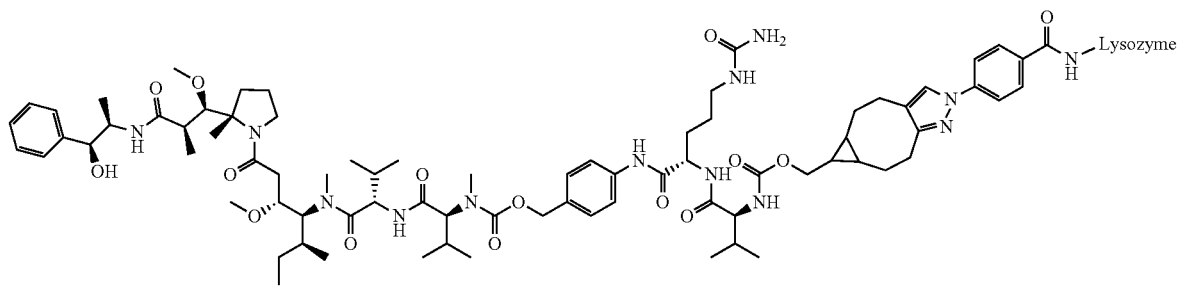
29
DoC 1
exp: 15 746 Da
obs: 15 752 Da
Compound 30
Compound 30 was prepared following General procedure D with Lysozyme as a Protein and DBCO-MMAE as a Trans-tagging reagent. MS spectrum of compound 30 was obtained following General procedure C.
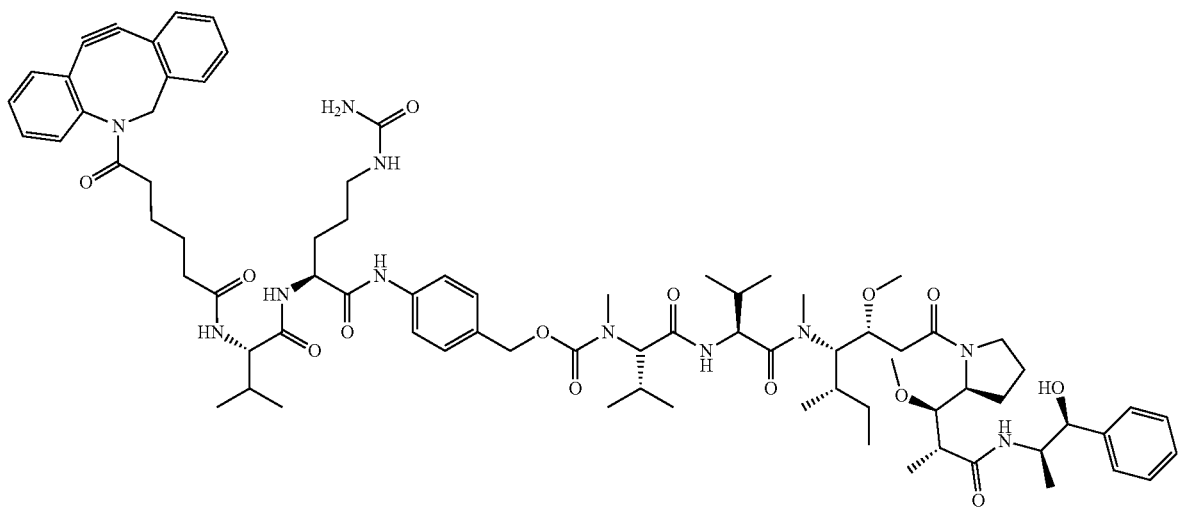
DBCO-MMAE
Trans-tagging

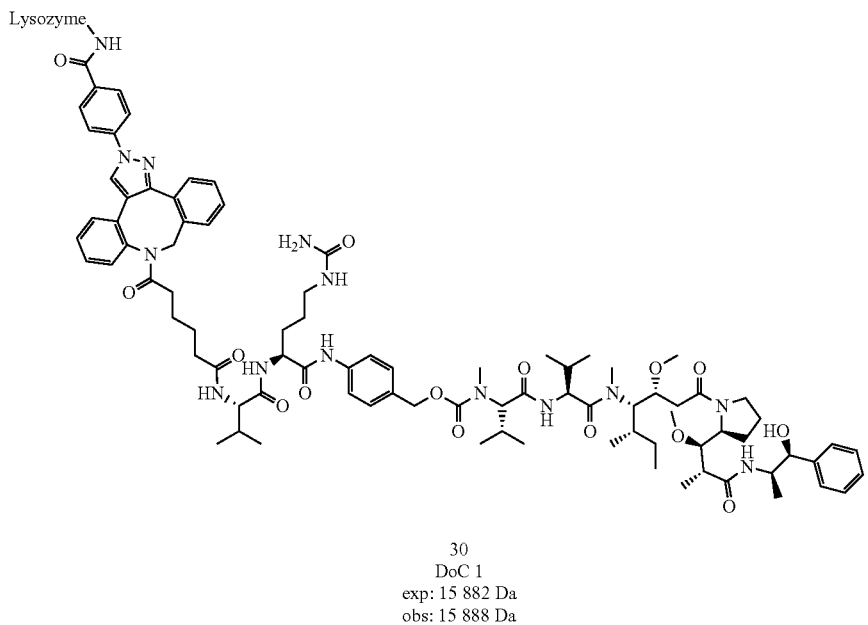

30
DoC 1
exp: 15 882 Da
obs: 15 888 Da

Compound 31

Trastuzumab-VC-MMAE was obtained from Trastuzumab and APN-VC-MMAE, following a standard reduction-alkylation protocol for cysteine conjugation of antibodies. As anticipated, Trastuzumab-VC-MMAE conjugate consisted of the mixture of species having DoC 0, 2, 4, 6 and 8. Each species was transformed into corresponding n+1 species upon preparation of compound 31 following General procedure D with Trastuzumab-VC-MMAE conjugate as a Protein and BCN-TAMRA as a Trans-tagging reagent. MS spectrum of compound 31 was obtained following General procedure C

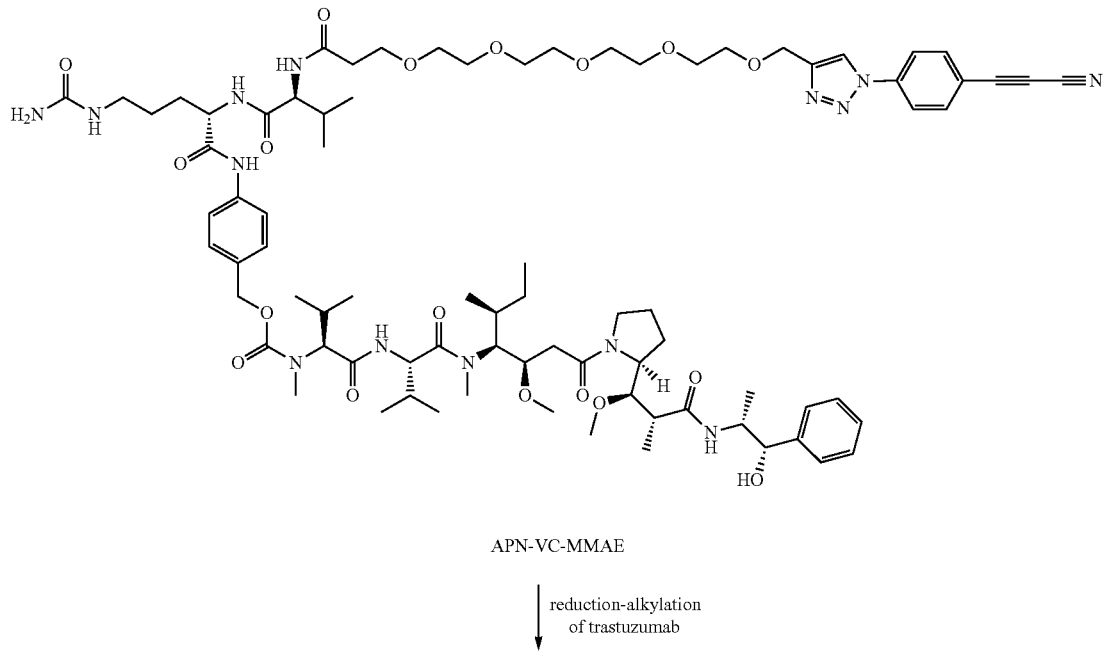

APN-VC-MMAE

↓ reduction-alkylation of trastuzumab

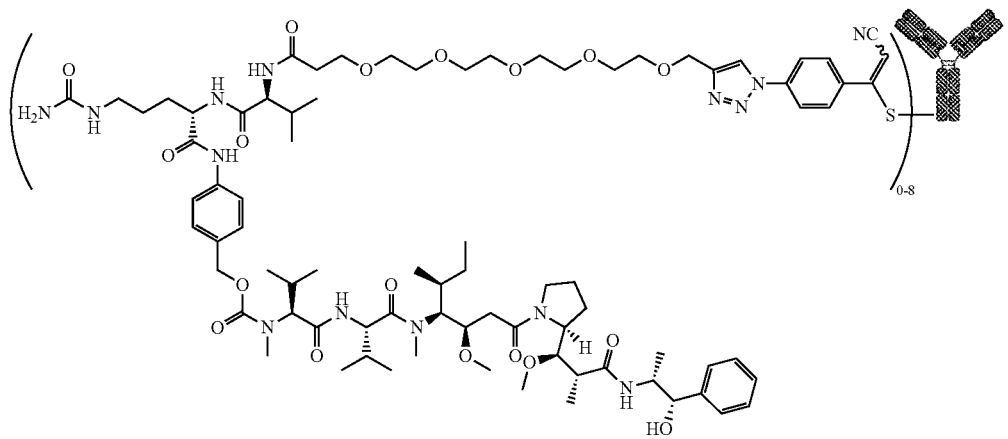
Trastuzumab-VC-MMAE
| Species: | exp: | obs: |
|---|---|---|
| DoC 0 | 145870 | 145870 |
| DoC 2 | 149024 | 149038 |
| DoC 4 | 152178 | 152198 |
| DoC 6 | 155332 | 155358 |
| DoC 8 | 158486 | 158516 |
BCN-TAMRA
Trans-tagging
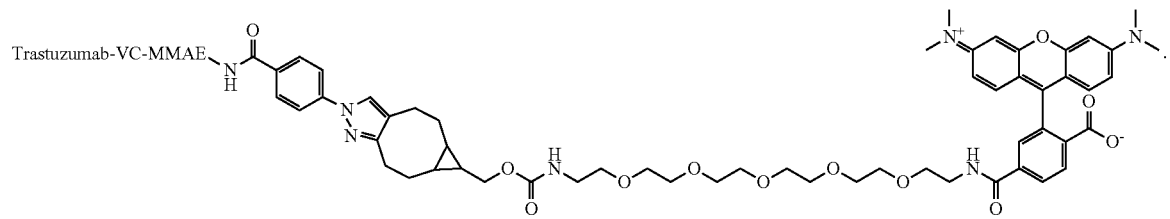
31
| Species: | exp: | obs: |
|---|---|---|
| DoC 0+1 | 146882 | 146920 |
| DoC 2+1 | 150036 | 150074 |
| DoC 4+1 | 153190 | 153228 |
| DoC 6+1 | 156344 | 156388 |
| DoC 8+1 | 159498 | 159552 |
Example 5: Preparation of a Compound of Formula (I): Preparation of Biotin-iSyd-APN
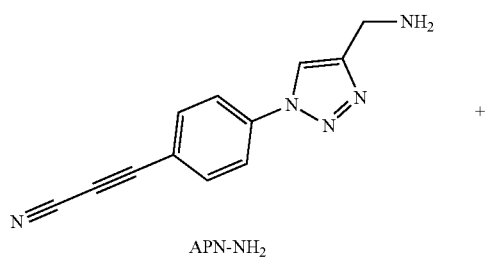
APN-NH$_2$
+

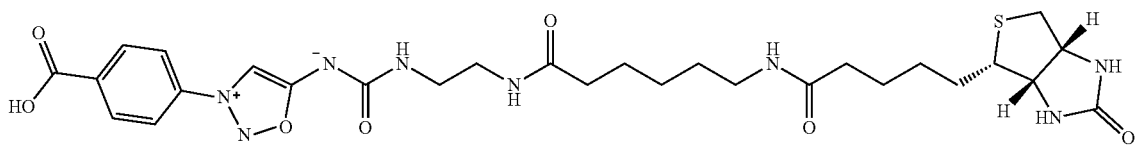

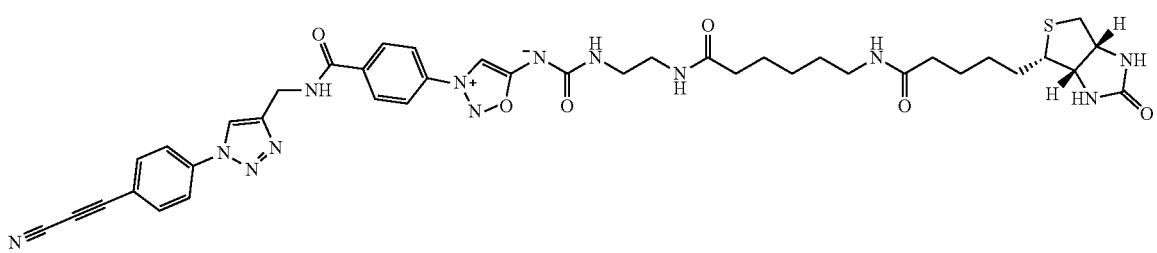

Biotin-iSyd-APN

To the solution of 11 (1 eq., 0.5 mL, 25 mM in DMSO) was added a solution of 2-bromo-1-ethyl-pyridinium tetrafluoroborate (1 eq., 125 μL, 0.1 M in DMF) followed by the solution of DIEA (1 eq., 25 μL, 0.1 M in DMF). The mixture was incubated at room temperature for 5 min and then the solution of APN-NH$_2$ (1.1 eq., 138 μL, 0.1 M in DMSO) was added, followed by the solution of DIEA (5 eq., 125 μL, 0.1 M in DMF). The resulting mixture was incubated at room temperature for 2 h and then purified by preparative HPLC to yield Biotin-iSyd-APN (6.17 mg, 59%) as a yellow solid. The structure of Biotin-iSyd-APN was confirmed by ESI-MS analysis (Method 1).

ESI-MS m/z: 836.6 [M+H]$^+$

Example 6: Bioconjugation Using Biotin-iSyd-APN 6.1 General Procedure E for the Preparation of Protein Conjugates (D-n) with Defined Degree of Conjugation, Applicable to Biomolecules Containing Free Cysteine Residues.

This comprises three parts:
Part I. Preparation of protein conjugates (E-1) with affinity tag in low conversion
Part II. Loading of protein conjugates (E-1) into the affinity column
Part III. Trans-tagging reaction 6.1.1 Part I. Preparation of Protein-iSyd3-Biotin Conjugates (E-1):

(E-1)

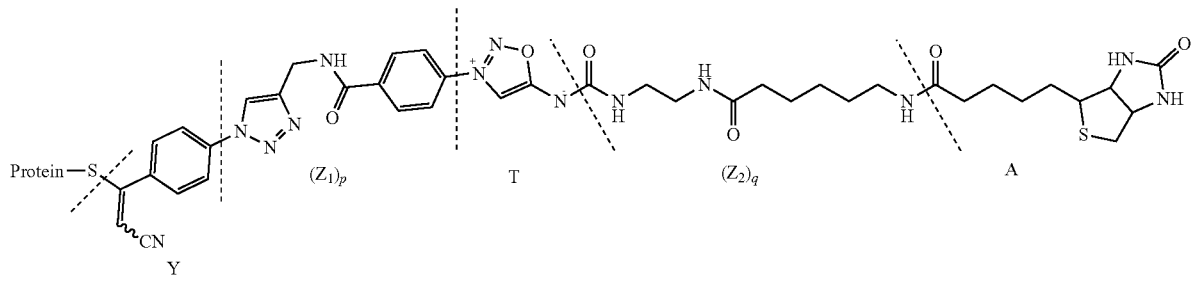

Protein-iSyd3-Biotin

A solution of Biotin-iSyd-APN reagent (0.1 eq., 34 μL, 500 μM in DMSO) were added to a solution of protein (1 eq., 5 mg/mL, 5 mL in PBS 1×, pH 7.4) at 25° C. The reaction mixture was maintained at 25° C. for 12 h and used in the next step without purification.

6.1.2 Part II. Loading of Protein Conjugates (E-1) into the Affinity Column Protein-iSyd3-Biotin conjugate (5 mL in PBS 1×, pH 7.4) was injected into HiTrap Streptavidin HP column (1 mL, GE Healthcare Life Sciences, Ref. 17-5112-01) equilibrated with PBS 1× (pH 7.4) using syringe pump at flow rate of 0.5 mL/min. The eluate containing unconjugated protein was collected and used in subsequent subsequent conjugation/loading cycles.

6.1.3 Part III. Trans-Tagging Reaction

Streptavidin column containing immobilized protein, was washed with 10 mL of PBS 1× (pH 7.4) and then with 10 mL of PBS/DMSO (9/1, pH 7.4) at 1 mL/min flow rate. Trans-tagging reaction was performed in the streptavidin column using as compound of formula (II) derivatives of dibenzocyclooctyne (DBCO). A solution of compound of formula (II) (1 mM, 1 mL in PBS 1×, pH 7.4 containing 10% of DMSO) was injected into the column. The column was incubated at 25° C. for 16 h, then connected to the inlet of Superdex 200 Increase column (GE Healthcare Life Sciences), equilibrated with PBS 1× (pH 7.4), and eluted with PBS 1× (pH 7.4, 48 mL) at flow rate of 0.15 mL/min using ÄKTA Pure chromatography system (GE Healthcare Life Sciences). The collected fraction of the functionalized protein conjugate was concentrated using Vivaspin 500 centrifugal filtration unit (MWCO 10 kD, Sartorius). The resulting conjugates of formula (D'-1) were subjected to MS analysis according to General Procedure C.

Compound 32

Compound 32 was prepared following General procedure E with Trastuzumab as a Protein and DBCO-COOH as a Trans-tagging reagent. MS spectrum of compound 32 was obtained following General procedure C.

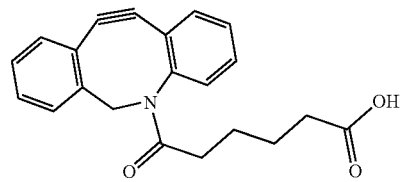

DBCO-COOH

Trans-tagging

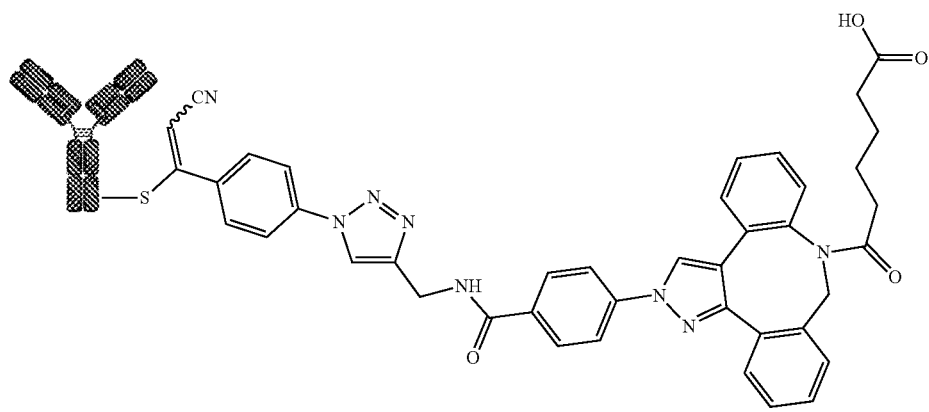

32
DoC 1
exp: 146 590 Da
obs: 146 618 Da

Example 7: Preparation of a Compound of Formula (I): Preparation of NHS-TCO-Biotin

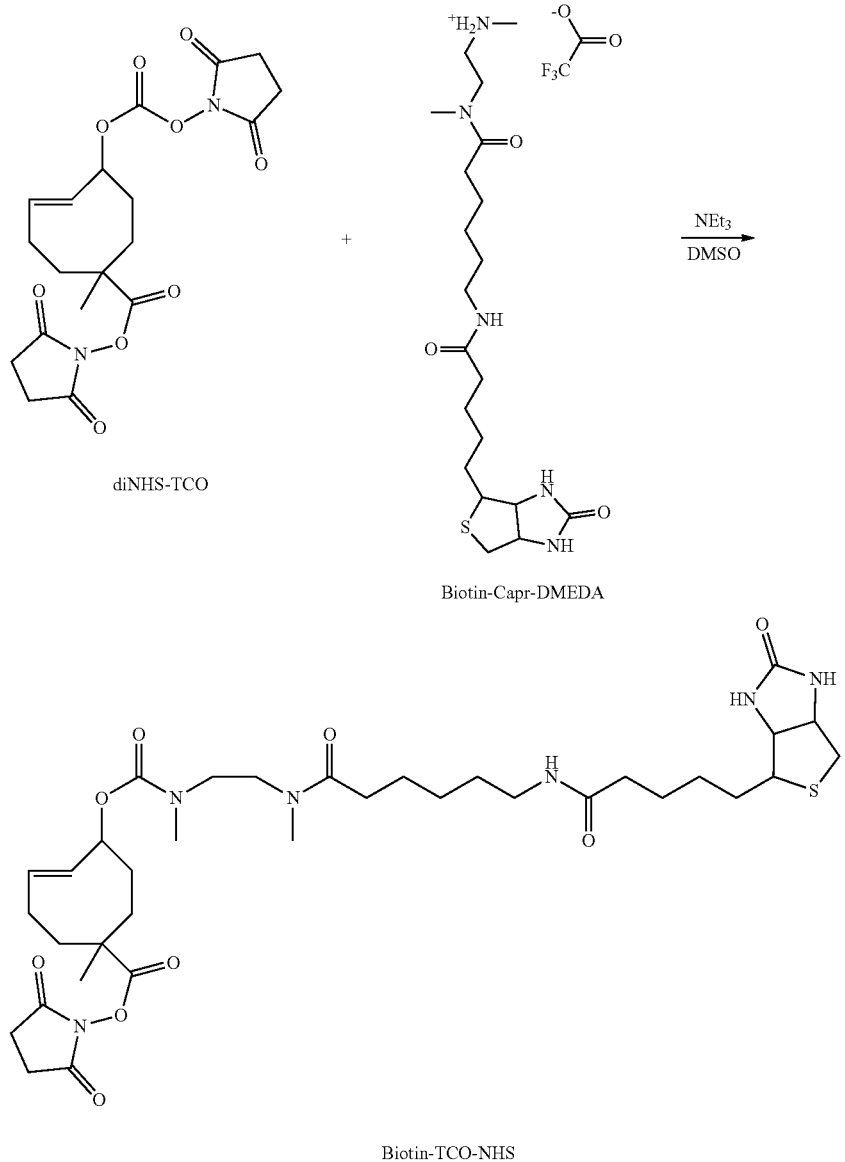

diNHS-TCO

Biotin-Capr-DMEDA

Biotin-TCO-NHS

To a solution of diNHS-TCO (1 eq., 0.1 M in DMSO, 100 μl) was added NEt₃ (2.5 eq., 0.25 M in DMSO, 100 μl) and Biotin-Capr-DMEDA (1 eq., 0.1 M, 100 μl). The resulting mixture was stirred in the dark at RT during 30 min. An aliquot of the reaction was analysed by LCMS confirming 88% conversion. The reaction mixture was then purified by preparative HPLC (40 min run, detection at 210 nm; buffer A: H₂O miliQ+0.05% of TFA; buffer B: ACN; 40 min— from 5% to 95% B). The fraction containing the expected product was collected directly after the UV detector in a flask maintained in a liquid nitrogen bath. The collected fraction was promptly lyophilized and the resulting product, Biotin-TCO-NHS, was dissolved in DMSO to afford a 0.1 M solution. The structure of Biotin-TCO-NHS was confirmed by ESI-MS analysis (Method 1).

ESI-MS m/z: 335.5 [M+H]$^+$

Example 8: Bioconjugation Using Biotin-TCO-NHS 8.1 General Procedure F for the Preparation of Protein Conjugates (D-n) with Defined Degree of Conjugation This comprises three parts:
Part I. Preparation of protein conjugates (E-1) with affinity tag in low conversion
Part II. Loading of protein conjugates (E-1) into the affinity column
Part III. Trans-tagging reaction 8.1.1 Part I. Preparation of Protein-TCO-Biotin Conjugates (E-1):

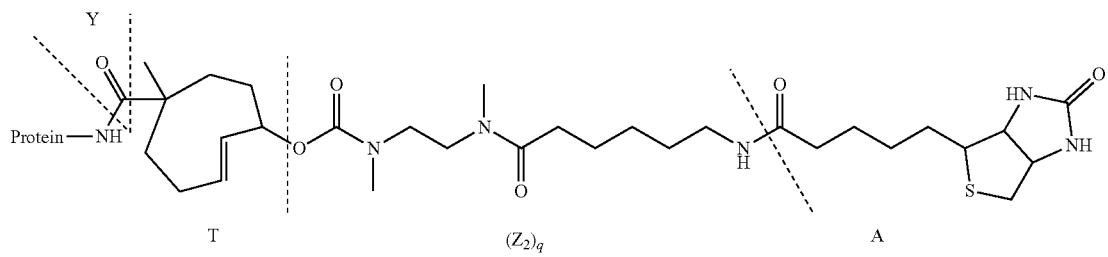

(E-1)

Biotin-TCO-NHS reagent (2 eq., 4.0 mM, 77 μl) was added to a solution of trastuzumab (1 eq., 5.607 mg/ml, 4 ml in potassium phosphate buffer 50 mM, pH 8.5). The reaction mixture was maintained at 25° C. in the darkness for 2 h.

8.1.2 Part II. Loading of Antibody Conjugates (E-1) into the Affinity Column

DoC 1 Trastuzumab-TCO-Biotin conjugate (4 mL in Phosphate Buffer 50 mM, pH 8.5) was loaded on HiTrap Streptavidin HP column (1 mL, GE Healthcare Life Sciences, Ref. 17-5112-01) equilibrated with a 9/1 mixture of PBS 1× (pH 7.4) and DMSO using a syringe pump at flow rate of 0.2 mL/min. The column was then washed with a 9/1 mixture of PBS 1× and DMSO (pH 7.4, 1.0 mL/min, 10 CV) and the fractions of unconjugated antibody were collected and concentrated on using Vivaspin 20 centrifugal filtration unit (MWCO 10 kDa, Sartorius) for use in subsequent cycles. The column was then washed with PBS 1× (pH 7.4).

8.1.3 Part III. Trans-Tagging Reaction

Trans-tagging reaction was performed in the streptavidin column using as compound of formula (I) tetrazine (Tz) derivatives bearing fluorophore Cy5 as secondary functionality. The column was equilibrated with the solution of a Tz derivative (600 μM, 1 mL in PBS 1×, pH 7.4 containing 10% of DMSO) at flow rate of 0.2 mL/min. The column was incubated at 25° C. for 24 h and then eluted with a 9/1 mixture of PBS 1× (pH 7.4, 3 mL) and DMSO at flow rate of 0.2 mL/min using a syringe pump. The collected fraction of the functionalized antibody conjugate was concentrated using Vivaspin 20 centrifugal filtration unit (MWCO 50 kD, Sartorius) and then purified by gel filtration chromatography on Bio-Spin P-30 Columns (Bio-Rad, Hercules, USA) equilibrated with PBS 1× (pH 7.4). The general yield was 150-500 μg of antibody conjugates per trans-tagging reaction. The resulting conjugates of formula (D'-1) (50 μg) were subjected to MS analysis according to General Procedure C.

Compound 33 Compound 33 was prepared following General Procedure F with Trastuzumab as a Protein and Me-Tz-Cy5 as a Trans-tagging reagent. MS spectrum of compound 33 was obtained following General Procedure C.

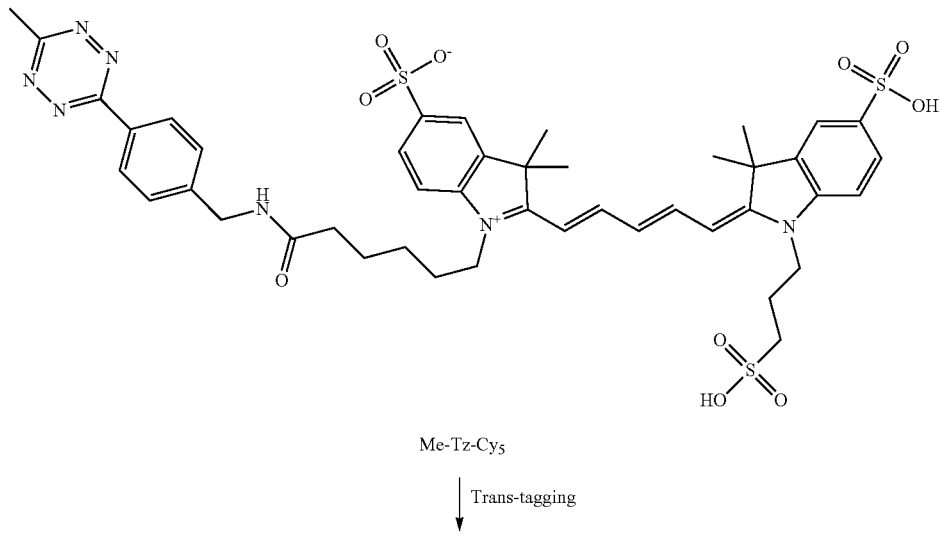

Me-Tz-Cy5

↓ Trans-tagging

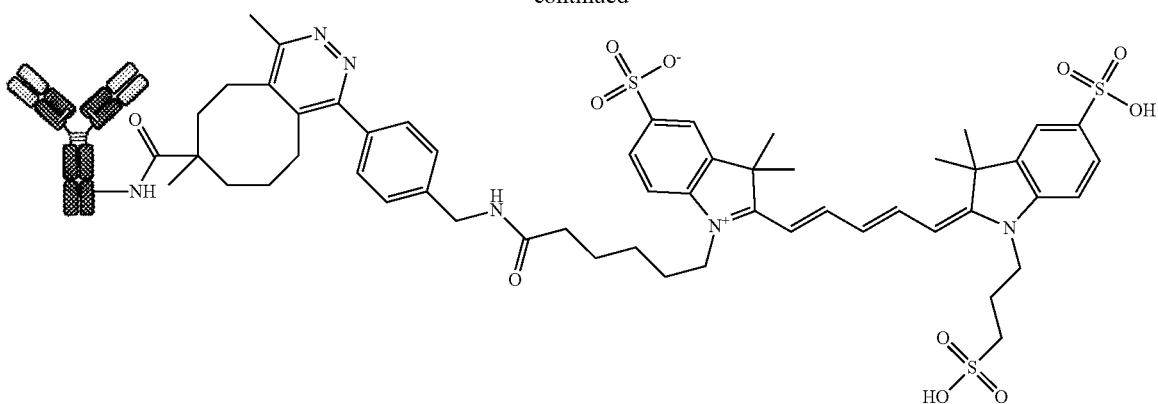
33
DoC 1
exp: 146 953 Da
obs: 146 958 Da
Compound 34 Compound 34 was prepared following General procedure D with Trastuzumab as a Protein and 17 as a Trans-tagging reagent. MS spectrum of compound 34 was obtained following General procedure C.
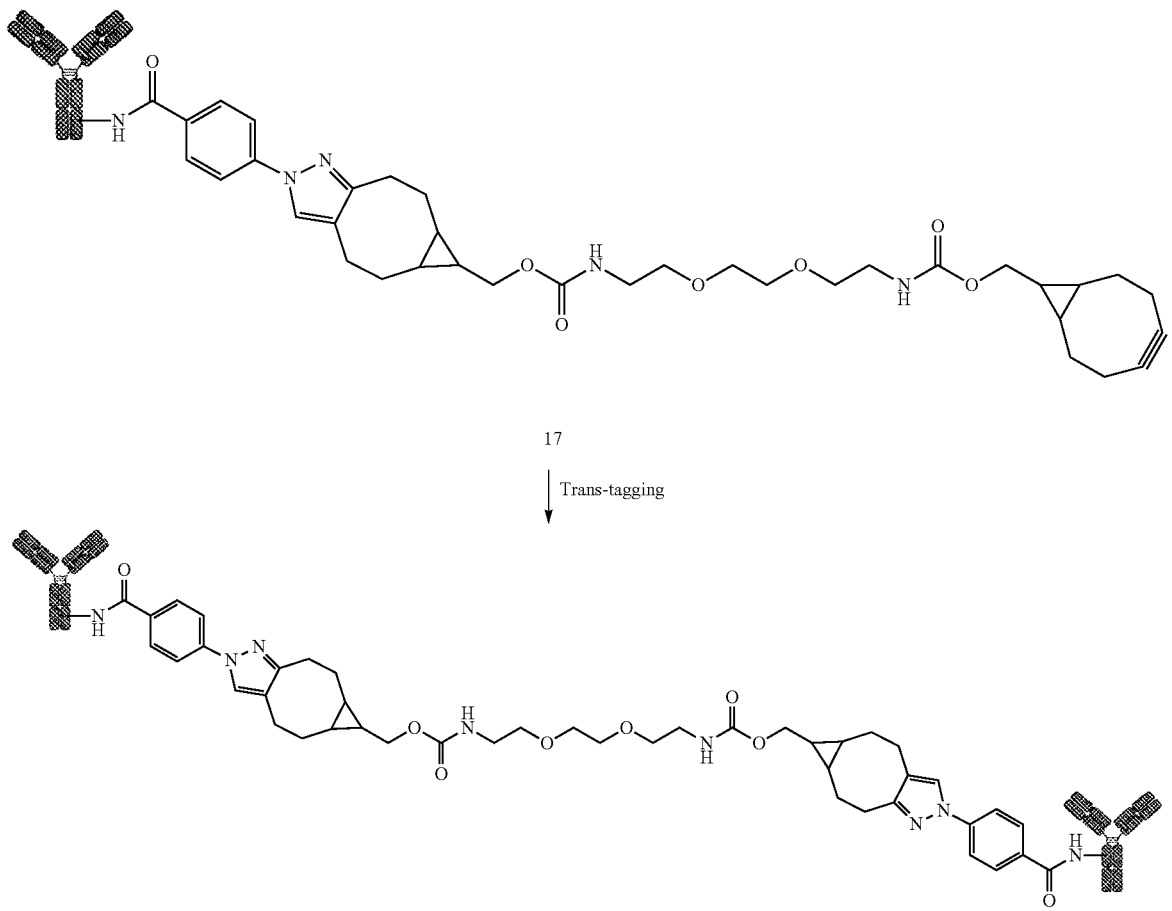
34
DoC 1
exp: 292 538 Da
obs: 292 574 Da Compound 35
Compound 35 was prepared following General procedure D with Trastuzumab as a Protein and BCN-Doxorubicin as a Trans-tagging reagent. MS spectrum of compound 35 was obtained following General procedure C.
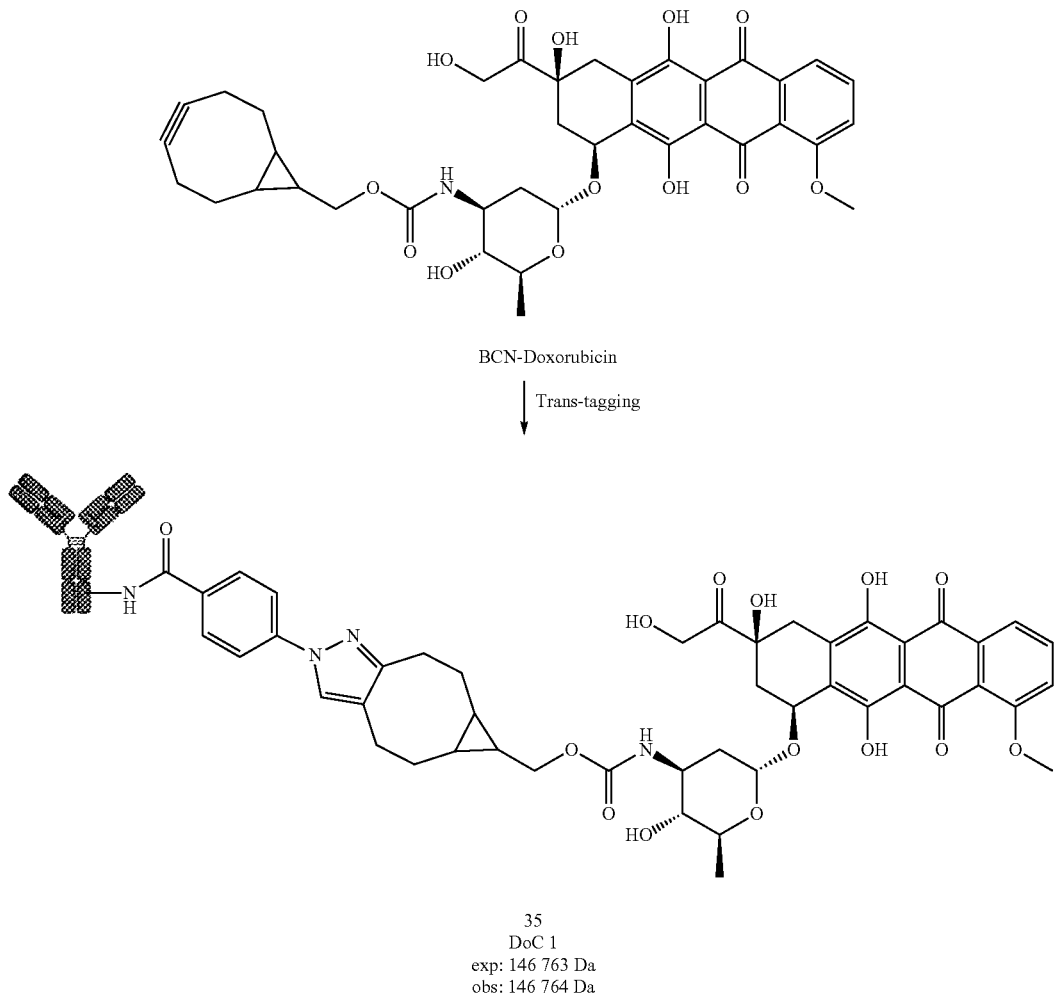
35
DoC 1
exp: 146 763 Da
obs: 146 764 Da
Example 9: Preparation of a Compound of Formula (I): Preparation of DTB-iSyd-NHS
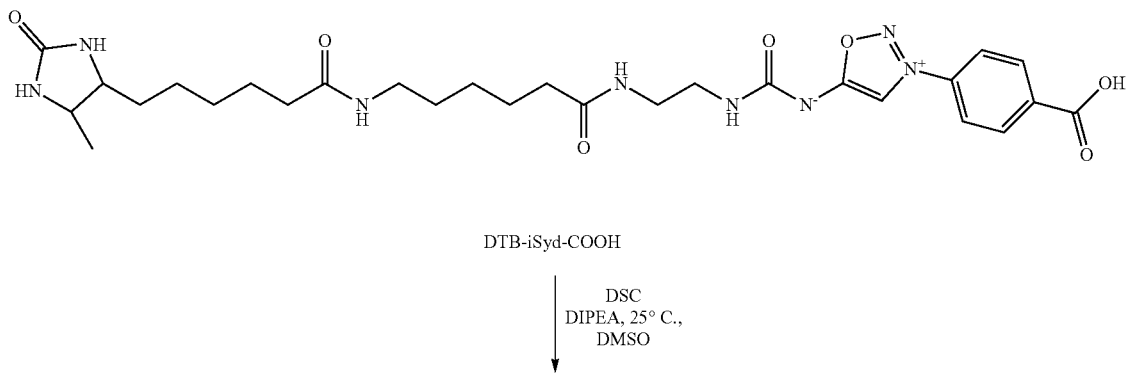
DTB-iSyd-COOH
DSC
DIPEA, 25° C.,
DMSO -continued

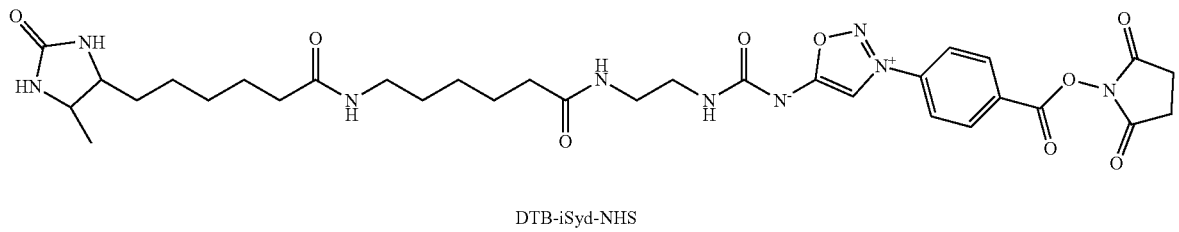

DTB-iSyd-NHS

To a solution of DTB-iSyd-COOH (1 eq., 3 mg, 0.005 mmol) were added NHS (0.025 mmol, 5 eq., 250 µL, 0.1M in DMSO) and DCC (0.01 mmol, 2 eq., 100 µL, 0.1M in DMSO) and the mixture was stirred overnight at room temperature. The resulting mixture was purified by preparative HPLC (40 min run, detection at 254 nm; buffer A: H$_2$O miliQ 0.05% of TFA; buffer B: ACN; 40 min—from 5% to 95% B). The collected fraction was promptly lyophilized to yield DTB-iSyd-NHS (2.24 mg, 0.003 mmol, 64%) as a yellow solid. The structure of DTB-iSyd-NHS was confirmed by ESI-MS analysis (Method 1).

ESI-MS m/z: 698.5 [M+H]$^+$

Example 10: Bioconjugation 2.1 General Procedure F for the Preparation of Protein Conjugates (D-n) with Defined Degree of Conjugation
This comprises three parts:
Part I. Preparation of protein conjugates (E-1) with affinity tag in low conversion
Part II. Loading of protein conjugates (E-1) into the affinity column
Part III. Trans-tagging reaction 2.1.1 Part I. Preparation of Protein-iSyd-DTB Conjugates (E-1):

A solution of DTB-iSyd-NHS reagent (0.16 eq., 500 µM in DMSO) was added to a solution of the protein (1 eq., 5 mg/mL, 5 mL in potassium phosphate buffer, pH 8.5) at 25° C. The reaction mixture was maintained at 25° C. for 15 min and used in the next step without purification.

4.1.2 Part II. Loading of Protein Conjugates (E-1) into the Affinity Column

Protein-iSyd-DTB conjugate (5 mL in potassium phosphate buffer, pH 8.5) was injected into HiTrap Streptavidin HP column (1 mL, GE Healthcare Life Sciences, Ref. 17-5112-01) equilibrated with potassium phosphate buffer (pH 8.5) using syringe pump at flow rate of 0.5 mL/min. The eluate containing unconjugated protein was collected and used in subsequent subsequent conjugation/loading cycles.

Parts I and II were repeated 20 times while keeping the amount of added DTB-iSyd-NHS at 0.16 eq. comparing to the amount of protein engaged in each cycle.

4.1.3 Part III. Trans-Tagging Reaction

Streptavidin column containing immobilized protein, obtained after repeating Part I and II 20 times, was washed with 10 mL of PBS 1× (pH 7.4) and then with 10 mL of PBS/DMSO (9/1, pH 7.4) at 1 mL/min flow rate.

Trans-tagging reaction was performed in the streptavidin column using as compound of formula (II), such as derivatives of bicyclononyne (BCN). A solution of compound of formula (II) (20 µM, 1 mL in PBS 1×, pH 7.4 containing 10% of DMSO) was injected into the column. The column was incubated at 25° C. for 16 h, then connected to the inlet of Superdex 200 Increase column (GE Healthcare Life Sciences), equilibrated with PBS 1× (pH 7.4), and eluted with PBS 1× (pH 7.4, 48 mL) at flow rate of 0.15 mL/min using ÄKTA Pure chromatography system (GE Healthcare Life Sciences). The collected fraction of the functionalized (E-1)

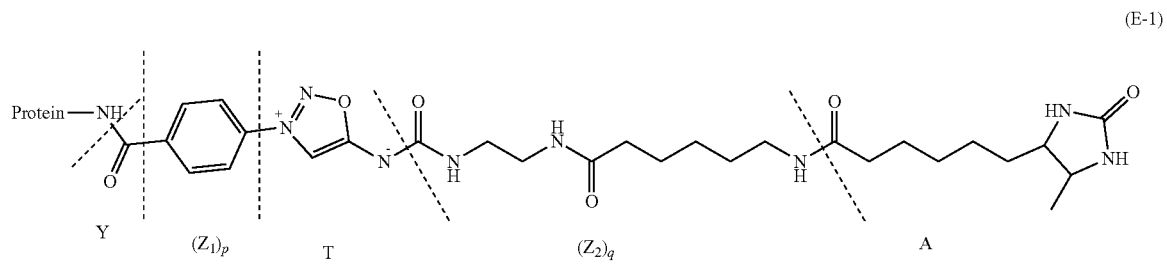

protein conjugate was concentrated using Vivaspin 500 centrifugal filtration unit (MWCO 10 kD, Sartorius). The resulting conjugates of formula (D'-1) were subjected to MS analysis according to General Procedure C.

The following compound (D-1) were prepared:

Compound 36

Compound 36 was prepared following General procedure F with trastuzumab as Protein and BCN-TAMRA as a Trans-tagging reagent. MS spectrum of compound 36 was obtained following General procedure C.

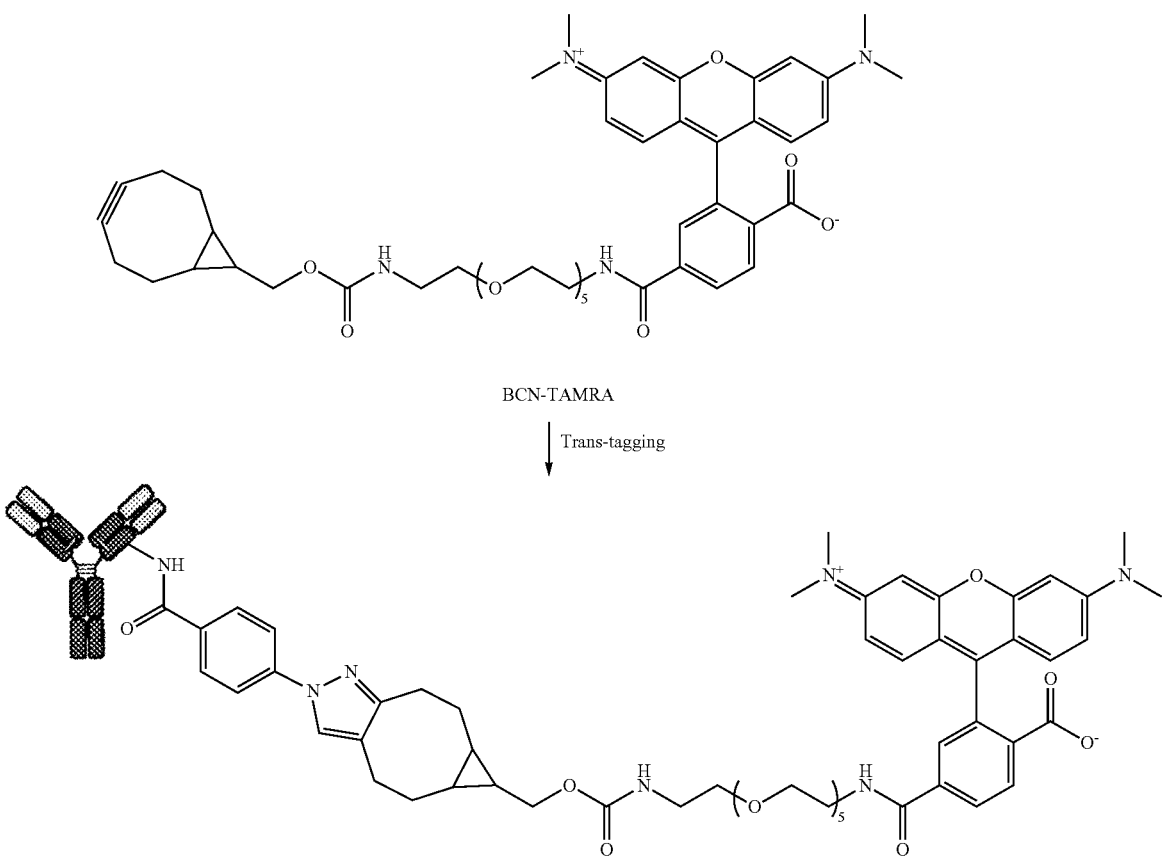

BCN-TAMRA

36
DoC 1
exp: 146 887 Da
obs: 146 891 Da

Comparative Example

The DARX process of the present invention and the plug-and-play process disclosed by Dovgan et al (Bioconjugate Chemistry, 2017, vol. 28, pages 1452-1457) have been conducted to prepare the compound 8. The mass spectrometry analysis of each compound 8 obtained has been carried out. The results are illustrated in FIG. 2. The representative mass spectrum of compound 8 obtained via the DARX process (2A) shows that the compound contains 95% of the desired DoC 1 species. The representative mass spectrum of compound 8 obtained via the plug-and-play process (2B) shows that the compound contains only 35% of the desired DoC 1 species along with 42% of unconjugated antibody and 23% of higher DoC species.

The DARX process of the invention therefore leads to higher specificity and efficiency of conjugation, with a more controlled degree of conjugation.

The invention claimed is:

1. A mixture of regioisomeric DAR-specific protein conjugates of formula (D-n):

Protein-(G)$_n$     (D-n)

wherein n represents the total degree of conjugation (DoC) and is an integer consisting of between 1 and 8;

Protein is a naturally occurring or synthetic protein, or a fragment thereof;

(G) refers to conjugate fragment(s), identical or different that is/are grafted to Protein at the same or different sites of attachment, provided that each fragment (G) has a respective degree of conjugation I consisting of between 1 and 8, where $\Sigma(i)=n$;

and where each fragment (G) is of the following formula:

—Y—(Z$_1$)$_p$—P—(Z$_3$)$_s$—F     (G)

provided that each of Y, Z$_1$, P, Z$_3$, F, n, p and s are the same or different for each (G) and in case n is higher than 1, (G) fragments in (D-n) can be same or different;

wherein for a given conjugate fragment (G):

there is a defined respective Degree of Conjugation (DoC) i; and the mixture comprises conjugate(s) having said fragment (G), such that at least 90% of said conjugate(s) have the defined respective DoC i;

p and s are independently 0 or 1;

Z$_1$ and Z$_3$ are optional spacer units independently selected from the group consisting of a C6-C12 arylene; a linear or branched, saturated or unsaturated, C$_1$-C$_{60}$ alkylene group optionally interrupted and/or terminated by one or more chemical groups selected from —O—, —S—, —S(O)—, —SO2-, —O—P(O)(OH)—O—, —C(O)—, —NH—, —C(O)NH—, —NHC(O)—, —C(O)NR$_4$—, —NR$_4$C(O)—, heteroarylene, arylene, mono or bicyclic (C3-C10)cycloalkylene, glycosyl, an —O—(CH$_2$—CH$_2$—O—)$_r$—, —NH—(CH$_2$—CH$_2$—O—)$_r$—, —(—O—CH$_2$—CH$_2$—)$_r$ or —(CH$_2$—CH$_2$—O—)$_r$— groups; and an amino acid or peptide residue, where the rings may be optionally fused;

in which r is an integer ranging from 1 to 24, and where R$_4$ is a solubility unit selected from the group consisting of C1-C6 alkylene, where one or more H is/are substituted by any of the following fragments:

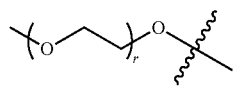

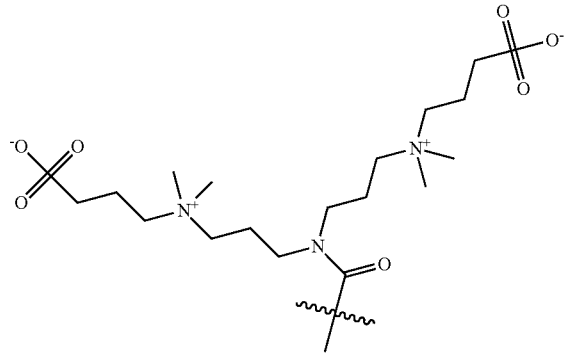

P is a trans-tagged unit resulting from the reaction of two complementary trans-tagging functions T and C, P being selected from:

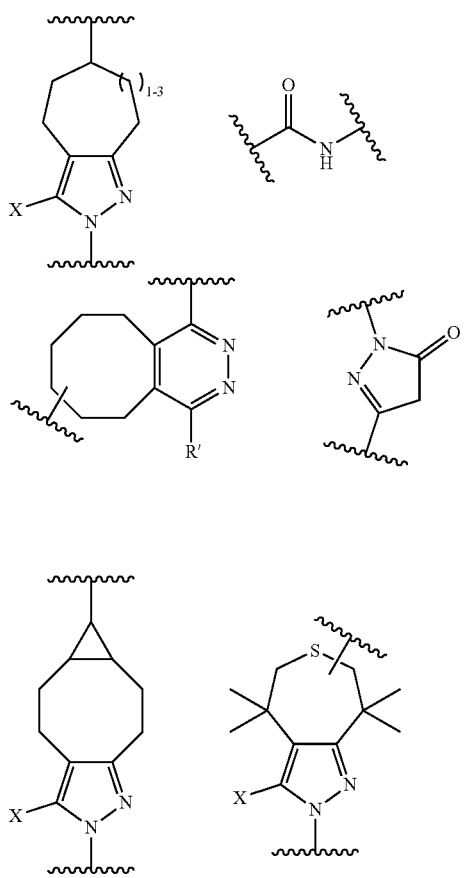

-continued

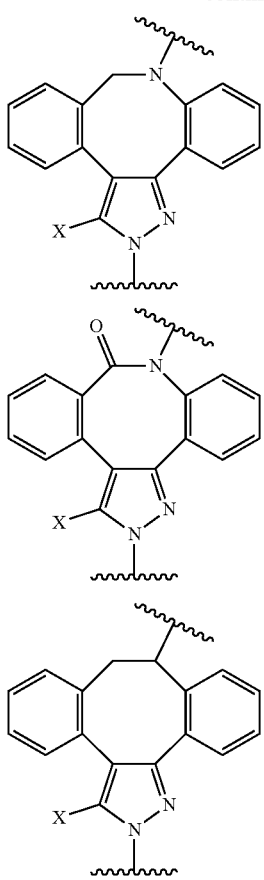

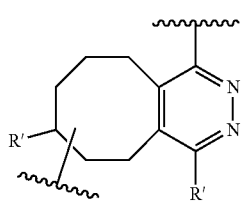

F is a functional agent, selected from cytotoxic drugs; antineoplastic agents;

oligonucleotides; and detection agents;

X is H or a halogen atom selected from F, Cl, Br and I;

Y is a chemical residue resulting from the reaction of R with amino acid residues present in Protein under aqueous conditions, selected from the group consisting of:

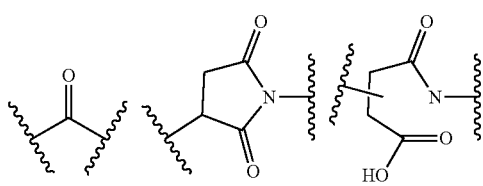

-continued

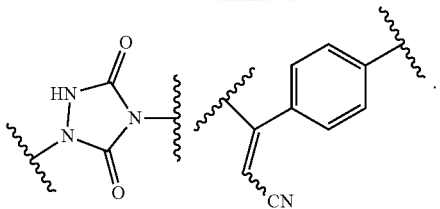

2. The mixture of protein conjugates (D-n) of claim 1, comprising a protein conjugate having a DoC of 1 having the formula (D-1):

$$\text{Protein-Y}—(Z_1)_p—P—(Z_3)_s—F \qquad (D\text{-}1)$$

wherein Protein, Y, $Z_1$, P, $Z_3$, F, p and s are defined as in claim 1, and wherein said conjugates having the conjugate fragment of formula (G):

$$—Y—(Z_1)_p—P—(Z_3)_s—F \qquad (G)$$

comprise at least 90% of conjugate (D-1), said fragments being grafted on the same or different sites of attachment of the Protein.

3. The mixture of protein conjugates (D-n) of claim 1 wherein F is selected from cytotoxic drugs and antineoplastic agents.

4. The mixture of protein conjugates of formula (D-n) according to claim 1 where Protein is a monoclonal antibody.

5. The process of preparation of the mixture of protein conjugates (D-n):

$$\text{Protein-}(Y—(Z_1)_p—P—(Z_3)_s—F)_n \qquad (D\text{-}n)$$

according to claim 1, comprising the steps of:
  i) reacting Protein with a reagent of formula (I):

$$R—(Z_1)_p\text{-}T\text{-}(Z_2)_q\text{-}A \qquad (I)$$

wherein:
Protein is defined as above;
R is a chemical function reactive towards amino acid residues present in Protein under aqueous conditions, wherein R is chosen from the group consisting of:

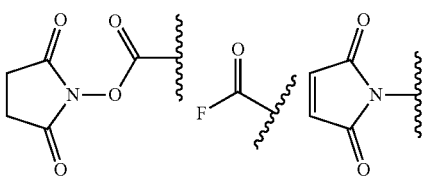

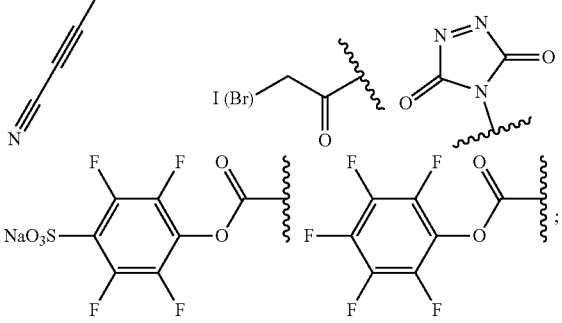

$Z_1$ and $Z_2$ are optional spacer units independently selected from the group consisting of a C6-C12 arylene; a linear or branched, saturated or unsaturated, $C_1$-$C_{60}$ alkylene group optionally interrupted and/or terminated by one or more chemical groups selected from —O—, —S—, —S(O)—, —SO2-, —O—P(O)(OH)—O—, —C(O)—, —NH—, —C(O)NH—, —NHC(O)—, —C(O)NR$_4$—, —NR$_4$C(O)—, heteroarylene, arylene, glycosyl, an —O—(CH$_2$—CH$_2$—O—)$_r$—, —NH—(CH$_2$—CH$_2$—O—)$_r$—, —(—O—CH$_2$—CH$_2$)$_r$— or —(CH$_2$—CH$_2$—O—)$_r$— groups, and an amino acid or peptide residue;

in which r is an integer ranging from 1 to 24, and
where $R_4$ is a solubility unit selected from the group consisting of C1-C6 alkylene, where one or more H is/are substituted by any of the following fragments:

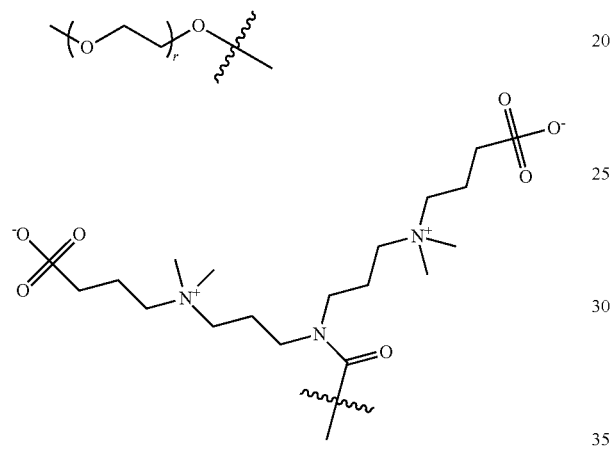

p and q are independently 0 or 1;
A is an affinity unit appropriate for immobilization of the compound of formula (I) on an affinity solid phase, which is a biotin or a DTB (D-desthiobiotin);
T is a trans-tagging unit selected from the group consisting of:

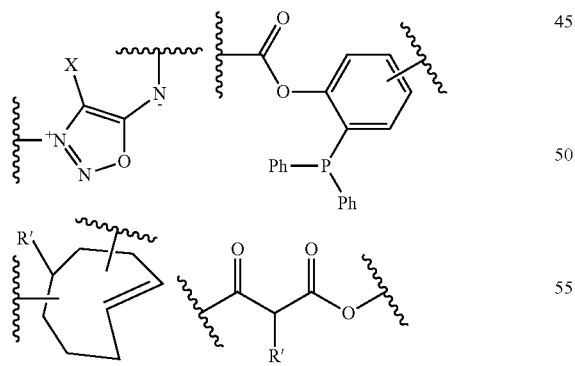

wherein X is selected from H, F, Cl, Br, I, and R' is selected from —H, saturated or unsaturated, $C_1$-$C_{60}$ alkyl group optionally interrupted by one or more chemical groups selected from —O—, —S—, —S(O)—, —SO2-, —O—P(O)(OH)—O—, —C(O)—, —NH—, —C(O)NH—, —NHC(O)—, —C(O)NR$_4$—, —NR$_4$C(O)—, heteroarylene, arylene, glycosyl, an —O—(CH$_2$—CH$_2$—O—)$_r$ or —NH—(CH$_2$—CH$_2$—O—)$_r$ groups in which r is an integer ranging from 1 to 24; and an amino acid or peptide residue, at low conversion to yield a conjugate of formula (E-1):

$$\text{Protein-Y—}(Z_1)_p\text{-T-}(Z_2)_q\text{-A} \qquad (E\text{-}1)$$

where Protein, Y, $Z_1$, T, $Z_2$, A, p and q are defined as above;
ii) loading the conjugates of formula (E-1) on an affinity column (B) comprising said affinity solid phase;
iii) optionally recycling Protein which has not reacted in step i) into step i);
iv) subjecting the affinity column (B) loaded with the conjugates of formula (E-1) to a trans-tagging reaction with a trans-tagging reagent of formula (II):

$$C\text{—}(Z_3)_s\text{—}F' \qquad (II)$$

wherein
C is a bio-orthogonal chemical function exclusively reactive towards the T function in the reactional mixture, wherein C is selected from the group consisting of:

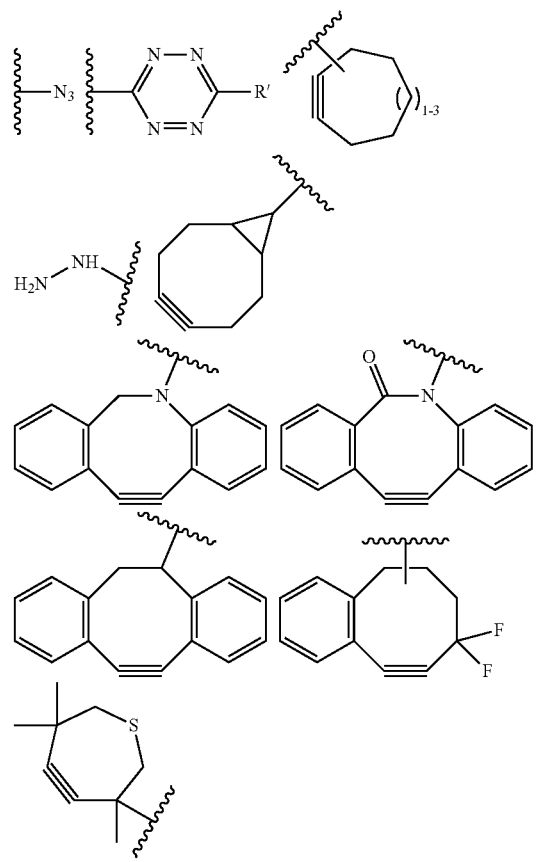

where R' is selected from —H, saturated or unsaturated, $C_1$-$C_{60}$ alkyl group optionally interrupted by one or more chemical groups selected from —O—, —S—, —S(O)—, —SO2-, —O—P(O)(OH)—O—, —C(O)—, —NH—, —C(O)NH—, —NHC(O)—, —C(O)NR$_4$—, —NR$_4$C(O)—, heteroarylene, arylene, glycosyl, an —O—(CH$_2$—CH$_2$—O—)$_r$ or —NH—(CH$_2$—CH$_2$—O—)$_r$ groups in which r is an integer ranging from 1 to 24; and an amino acid or peptide residue, s and $Z_3$ are defined as above; and F' is H or the F group or any bio-orthogonal function selected from the group consisting of an azide group;

an optionally substituted 1,2,4,5-tetrazine;

an optionally substituted trans-cyclooctene a C7-C9 cycloalkynyl derivative optionally interrupted by one or more chemical groups selected from —O—, —S—, —S(O)—, —SO2-, —O—P(O)(OH)—O—, —C(O)—, —NH—, —C(O)NH—; and/or optionally fused with a C3 to C6 cycloalkyl, or phenyl;

a hydrazine group;

an aldehyde group;

an —O—NH$_2$ group;

a OH group;

a COOH group;

a thiol group;

an arylpropiolonitrile group;

a benzocyclooctynyl or dibenzocyclooctynyl derivative, optionally interrupted by one or more chemical groups selected from —O—, —S—, —S(O)—, —SO2-, —O—P(O)(OH)—O—, —C(O)—, —N—, —NH—, —C(O)NH—, and/or optionally substituted by one or more halogen atoms, or =O; and a group selected from:

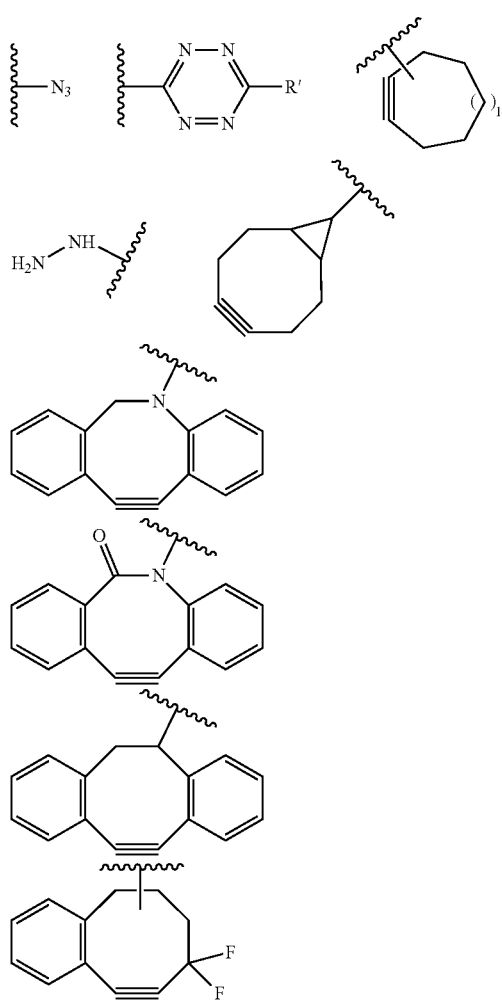

where R' is selected from —H, saturated or unsaturated, $C_1$-$C_{60}$ alkyl group optionally interrupted by one or more chemical groups selected from —O—, —S—, —S(O)—, —SO2-, —O—P(O)(OH)—O—, —C(O)—, —NH—, —C(O)NH—, —NHC(O)—, —C(O)NR$_4$—, —NR$_4$C(O)—, heteroarylene, arylene, glycosyl, an —O—(CH$_2$—CH$_2$—O—)$_r$ or —NH—(CH$_2$—CH$_2$—O—)$_r$ groups in which r is an integer ranging from 1 to 24; and an amino acid or peptide residue, where R$_4$ is a solubility unit selected from the group consisting of C1-C6 alkylene, where one or more H is/are substituted by any of the following fragments:

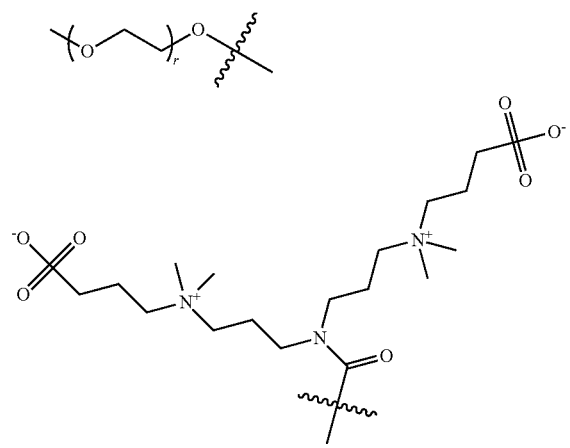

p and q are independently 0 or 1; so as to simultaneously form and release from the affinity column the conjugate of formula (D'-1):

Protein-Y—$(Z_1)_p$—P—$(Z_3)_s$—F'     (D'-1)

wherein Protein, Y, $Z_1$, p, s, F' and $Z_3$ are defined as above;

v) optionally repeating steps i) to iv) above with same or different compounds (I) and/or (II) so as to achieve a mixture comprising protein conjugates (D'-n) having a DoC of n:

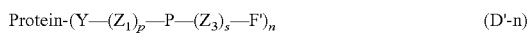
Protein-(Y—$(Z_1)_p$—P—$(Z_3)_s$—F')$_n$     (D'-n)

wherein Y, $Z_1$, P, $Z_3$, F' p, s may be the same or different for each grafted conjugate chain;

vi) optionally conducting where F' is different from the desired F group, a post-functionalization of the compound of formula (D'-n) by substituting in compound (D'-n) the group F' with the desired F group of formula (D-n).

6. The process according to claim 5 wherein steps i), ii) and/or iii) are repeated from 5 to 50 times.

7. The process according to claim 5 where A is biotin and the affinity solid phase of the column comprises streptavidin functions.

8. A tri-functional reagent having the following formula (I):

R—$(Z_1)_p$-T-$(Z_2)_q$-A     (I)

wherein:

$Z_1$, $Z_2$, T, A, R, p and q are defined as in claim 5.

9. A kit comprising a compound of formula (I) as defined in claim 5 and a compound of formula (II) as defined in claim 5.

10. The compound of formula (E-1):

Protein-Y—(Z$_1$)$_p$-T-(Z$_2$)$_q$-A (E-1)

where Protein, Y, Z$_1$, T, Z$_2$, p and q are defined as in claim 1 and A is a biotin or a DTB (D-desthiobiotin).

11. A method for treating cancer, comprising administering the mixture of conjugates of formula (D-n) as defined in claim 1 and where in formula (D-n) F is an antineoplastic agent or a cytotoxic drug and Protein is a monoclonal antibody targeting tumor cells, to a patient in the need thereof.

12. A therapeutic or imaging agent comprising the mixture of conjugates of formula (D-n) as defined in claim 1 and where in formula (D-n) F is an oligonucleotide and Protein is a polypeptide targeting tumor cells.

13. The therapeutic or imaging agent as defined in claim 12 where Protein is a monoclonal antibody targeting tumor cells.

14. The process according to claim 5, wherein the compound of formula (II) is chosen from the following compounds: 3,3,6,6-tetramethylthiacycloheptyne (TMTH),

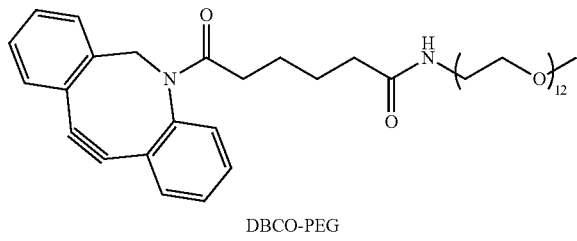
DBCO-PEG

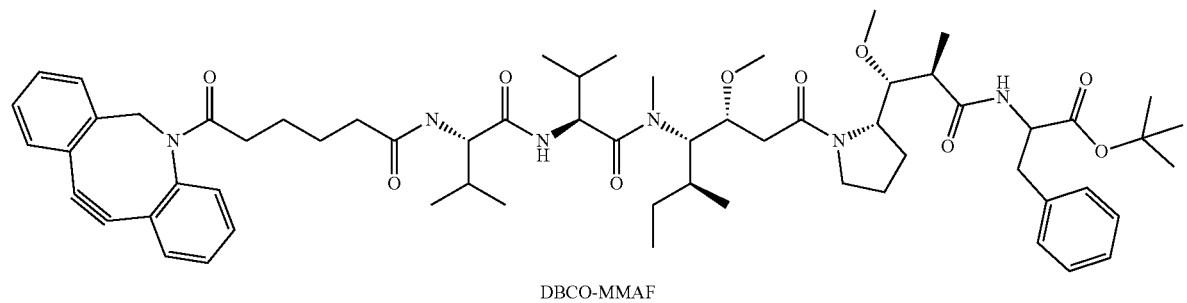
DBCO-MMAF

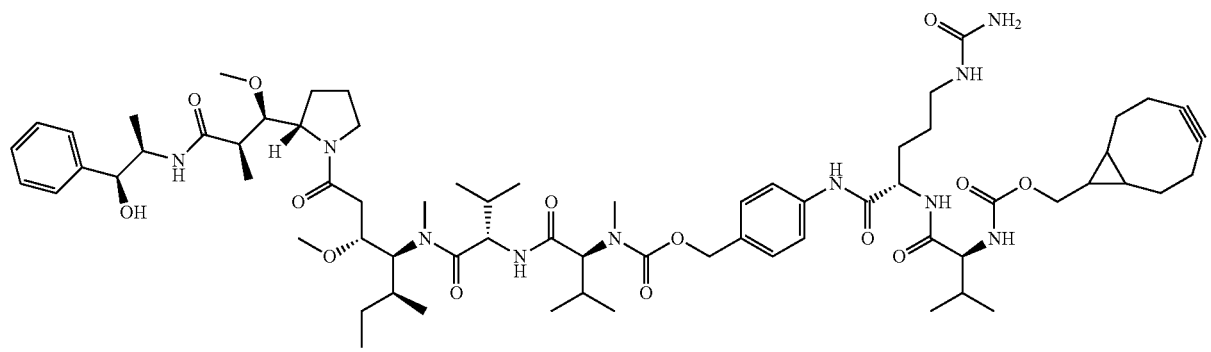
BCN-MMAE

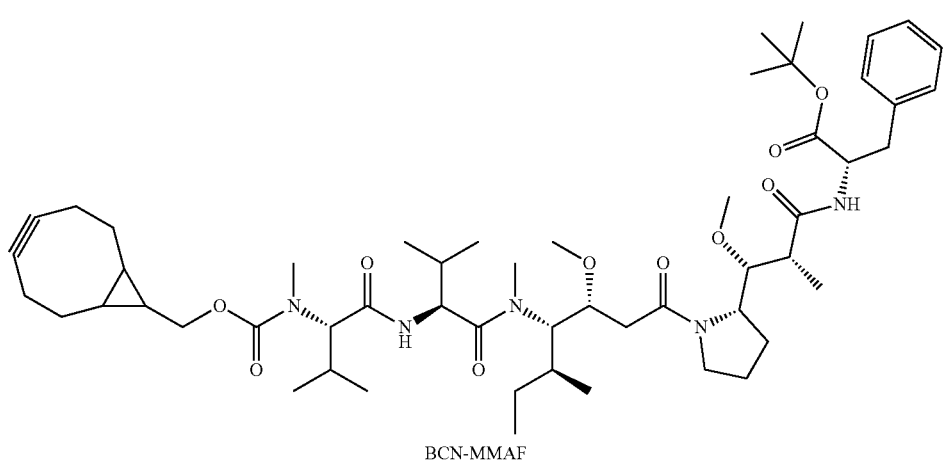
BCN-MMAF

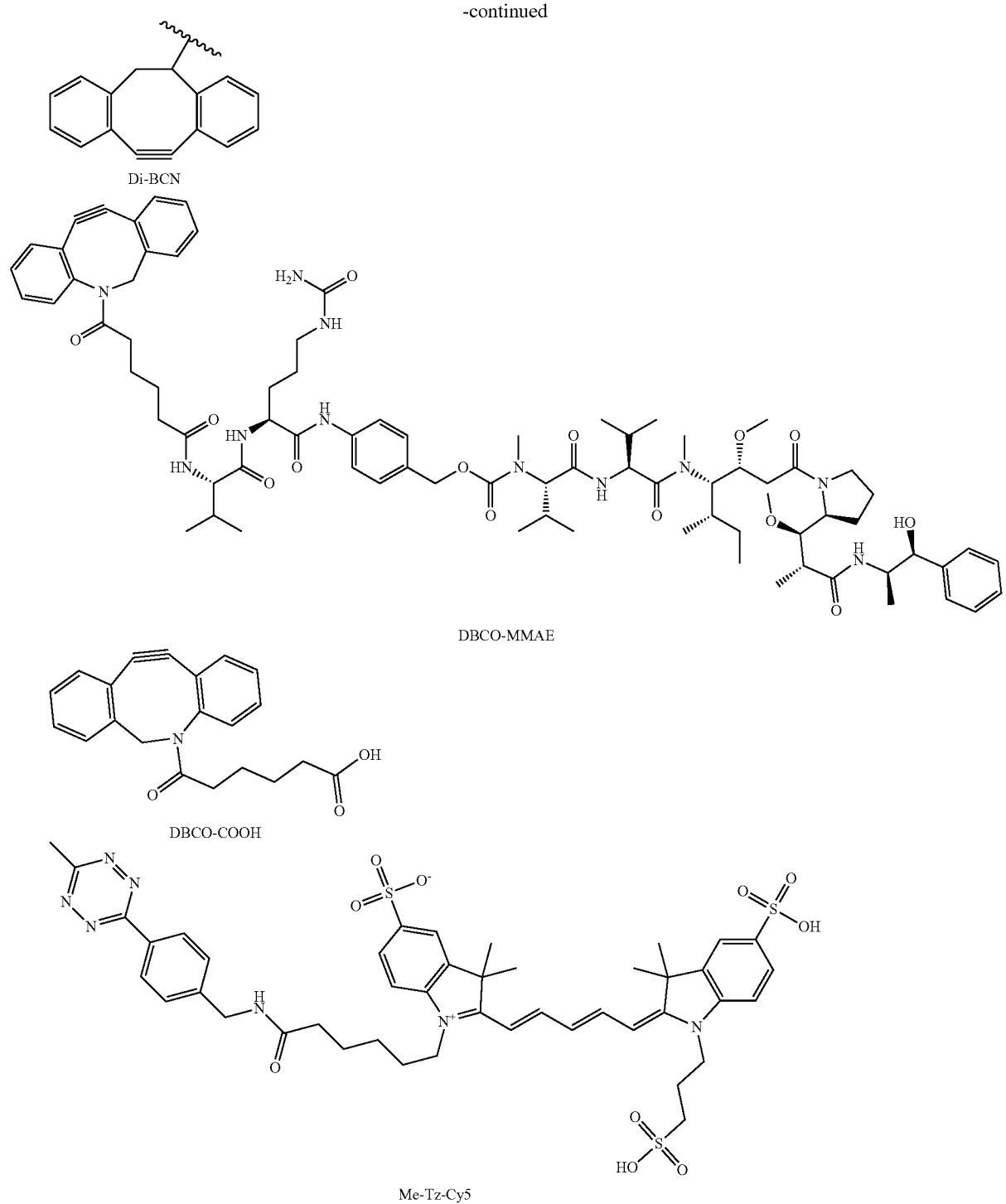
15. The mixture of protein conjugates (D-n) of claim 2 wherein F is selected from cytotoxic drugs and antineoplastic agents.
16. The mixture of protein conjugates of formula (D-n) according to claim 2 where Protein is a monoclonal antibody.
* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: oligonucleotide

<400> SEQUENCE: 1
tgcactctcg atgaccgagc t                                          21

<210> SEQ ID NO 2

```
<211> LENGTH: 21
<212> TYPE: DNA
<213> ORGANISM: Artificial Sequence
<220> FEATURE:
<223> OTHER INFORMATION: oligonucleotide

<400> SEQUENCE: 2
agctcggtca tcgagagtgc a                                               21
```